US012559541B2

(12) United States Patent
Hawkins et al.

(10) Patent No.: US 12,559,541 B2
(45) **Date of Patent: *Feb. 24, 2026**

(54) CD8A-BINDING FIBRONECTIN TYPE III DOMAINS

(71) Applicant: Janssen Biotech, Inc., Horsham, PA (US)

(72) Inventors: Rebecca Hawkins, Harleysville, PA (US); Steven Jacobs, North Wales, PA (US); Manuel Sepulveda, Princeton Junction, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/436,312

(22) Filed: Feb. 8, 2024

(65) Prior Publication Data

US 2024/0301033 A1 Sep. 12, 2024

Related U.S. Application Data

(63) Continuation of application No. 17/689,869, filed on Mar. 8, 2022, now Pat. No. 11,932,680, which is a continuation of application No. 16/821,064, filed on Mar. 17, 2020, now Pat. No. 11,299,534, which is a continuation of application No. 15/839,915, filed on Dec. 13, 2017, now Pat. No. 10,626,165.

(60) Provisional application No. 62/434,017, filed on Dec. 14, 2016.

(51) Int. Cl.

| | |
|---|---|
| ***C07K 14/00*** | (2006.01) |
| ***A61K 49/00*** | (2006.01) |
| ***A61K 51/08*** | (2006.01) |
| ***C07K 14/52*** | (2006.01) |
| ***C07K 14/78*** | (2006.01) |
| ***G01N 33/53*** | (2006.01) |
| ***G01N 33/566*** | (2006.01) |
| ***G01N 33/569*** | (2006.01) |
| ***G01N 33/574*** | (2006.01) |
| ***G01N 33/68*** | (2006.01) |

(52) U.S. Cl.

CPC .......... *C07K 14/78* (2013.01); *A61K 49/0002* (2013.01); *A61K 51/088* (2013.01); *G01N 33/53* (2013.01); *G01N 33/566* (2013.01); *G01N 33/569* (2013.01); *G01N 33/56966* (2013.01); *G01N 33/574* (2013.01); *G01N 33/57492* (2013.01); *G01N 33/68* (2013.01); *G01N 33/6887* (2013.01); *G01N 2333/70517* (2013.01); *G01N 2333/78* (2013.01)

(58) Field of Classification Search

None

See application file for complete search history.

(56) References Cited

U.S. PATENT DOCUMENTS

| | | | |
|---|---|---|---|
| 4,281,061 | A | 7/1981 | Zuk |
| 5,223,409 | A | 6/1993 | Ladner |
| 5,643,763 | A | 7/1997 | Dunn |
| 5,643,768 | A | 7/1997 | Kawasaki |
| 5,658,727 | A | 8/1997 | Barbas |
| 5,691,157 | A | 11/1997 | Gong |
| 5,846,456 | A | 12/1998 | Liu |
| 5,856,456 | A | 1/1999 | Whitlow |
| 6,018,030 | A | 1/2000 | Ferrari |
| 6,162,903 | A | 12/2000 | Trowern |
| 6,172,197 | B1 | 1/2001 | McCafferty |
| 6,355,776 | B1 | 3/2002 | Ferrari |
| 6,462,189 | B1 | 10/2002 | Koide |
| 6,472,147 | B1 | 10/2002 | Janda |
| 6,521,427 | B1 | 2/2003 | Evans |
| 6,582,915 | B1 | 6/2003 | Griffiths |
| 6,670,127 | B2 | 12/2003 | Evans |
| 6,673,901 | B2 | 1/2004 | Koide |
| 6,703,199 | B1 | 3/2004 | Koide |
| 6,818,418 | B1 | 11/2004 | Lipovsek |
| 6,846,655 | B1 | 1/2005 | Wagner |
| 6,969,108 | B2 | 11/2005 | Fukumoto |
| 7,078,490 | B2 | 7/2006 | Koide |
| 7,115,396 | B2 | 10/2006 | Lipovsek |
| 7,119,171 | B2 | 10/2006 | Koide |
| 7,153,661 | B2 | 12/2006 | Koide |
| 7,288,638 | B2 | 10/2007 | Jure-Kunkel |
| 7,427,672 | B2 | 9/2008 | Imanishi |
| 7,709,214 | B2 | 5/2010 | Freeman |
| 7,794,710 | B2 | 9/2010 | Chen |

(Continued)

FOREIGN PATENT DOCUMENTS

| | | | |
|---|---|---|---|
| CN | 102076713 | A | 5/2011 |
| CN | 103827361 | A | 5/2014 |

(Continued)

OTHER PUBLICATIONS

Hanes et al, "In vitro selection and evolution of functional proteins by using ribosome display," Proceedings of the National Academy of Sciences USA, vol. 94, pp. 4937-4942 (1997).

Helms, et al., "Destabilizing loop swaps in the CDRs of an immunoglobulin VL domain," Protein Science, 4: 2073-2081 (1995).

Hirsch et al., "Combination of EGFR gene copy number and protein expression predicts outcome for advanced non-, mall-cell lung cancer patients treated with gefitnib," Annals of Oncology, vol. 18, pp. 752-760 (2007).

Hoogenboom et al., "Natural and designer binding sites made by phage display technology" Immunology Today (2000) 7ol. 21, No. 8, pp. 371-378.

(Continued)

*Primary Examiner* — Maher M Haddad

(74) *Attorney, Agent, or Firm* — Ice Miller LLP

(57) ABSTRACT

Fibronectin type III domains (FN3) that specifically bind to CD8A, related polynucleotides capable of encoding CD8A-specific FN3 domains, cells expressing the FN3 domains, as well as associated vectors, and detectably labeled FN3 domains are useful in therapeutic and diagnostic applications.

19 Claims, 12 Drawing Sheets

Specification includes a Sequence Listing.

(56) References Cited

U.S. PATENT DOCUMENTS

| | | | | |
|---|---|---|---|---|
| 7,842,476 | B2 | 11/2010 | McGregor | |
| 7,943,743 | B2 | 5/2011 | Korman | |
| 8,217,149 | B2 | 7/2012 | Irving | |
| 8,278,419 | B2 | 10/2012 | Jacobs | |
| 8,293,482 | B2 | 10/2012 | Jacobs | |
| 8,552,154 | B2 | 10/2013 | Freeman | |
| 8,569,227 | B2 | 10/2013 | Jacobs | |
| 8,741,295 | B2 | 6/2014 | Olive | |
| 8,779,108 | B2 | 7/2014 | Queva | |
| 8,981,063 | B2 | 3/2015 | Chen | |
| 9,156,887 | B2 | 10/2015 | Jacobs | |
| 9,175,082 | B2 | 11/2015 | Zhou | |
| 9,200,273 | B2 | 12/2015 | Diem | |
| 9,212,224 | B2 | 12/2015 | Cogswell | |
| 9,326,941 | B2 | 5/2016 | Chae | |
| 9,546,368 | B2 | 1/2017 | Bennett | |
| 9,644,023 | B2 | 5/2017 | Torres | |
| 9,695,228 | B2 | 7/2017 | Mark | |
| 9,897,612 | B2 | 2/2018 | Diem | |
| 10,196,446 | B2 | 2/2019 | Goldberg | |
| 10,233,448 | B2 | 3/2019 | Maier | |
| 10,597,438 | B2 | 3/2020 | Diem | |
| 10,611,823 | B2 | 4/2020 | Diem | |
| 10,626,165 | B2 * | 4/2020 | Hawkins | G01N 33/569 |
| 11,299,534 | B2 * | 4/2022 | Hawkins | G01N 33/53 |
| 11,932,680 | B2 * | 3/2024 | Hawkins | G01N 33/574 |
| 2004/0197332 | A1 | 10/2004 | Ullrich | |
| 2004/0259781 | A1 | 12/2004 | Chiquet-Ehrismann | |
| 2005/0004029 | A1 | 1/2005 | Garcia | |
| 2005/0038229 | A1 | 2/2005 | Lipovsek | |
| 2005/0255548 | A1 | 11/2005 | Lipovsek | |
| 2005/0272083 | A1 | 12/2005 | Seshagiri | |
| 2006/0040278 | A1 | 2/2006 | Cojocaru | |
| 2006/0246059 | A1 | 11/2006 | Lipovsek | |
| 2006/0270604 | A1 | 11/2006 | Lipovsek | |
| 2007/0148126 | A1 | 6/2007 | Chen | |
| 2007/0160533 | A1 | 7/2007 | Chen | |
| 2007/0184476 | A1 | 8/2007 | Hsieh | |
| 2008/0015339 | A1 | 1/2008 | Lipovsek | |
| 2008/0220049 | A1 | 9/2008 | Chen | |
| 2008/0241159 | A1 | 10/2008 | Gerritsen | |
| 2009/0042906 | A1 | 2/2009 | Huang | |
| 2009/0176654 | A1 | 7/2009 | Cappuccilli | |
| 2009/0274693 | A1 | 11/2009 | Gilmer | |
| 2009/0299040 | A1 | 12/2009 | Camphausen | |
| 2009/0311803 | A1 | 12/2009 | Way | |
| 2010/0093662 | A1 | 4/2010 | Defaye | |
| 2010/0136129 | A1 | 6/2010 | Maite | |
| 2010/0144601 | A1 | 6/2010 | Jacobs | |
| 2010/0179094 | A1 | 7/2010 | Emanuel | |
| 2010/0203142 | A1 | 8/2010 | Zhang | |
| 2010/0216708 | A1 | 8/2010 | Jacobs | |
| 2010/0221248 | A1 | 9/2010 | Wittrup | |
| 2010/0254989 | A1 | 10/2010 | Bossenmaier | |
| 2010/0255056 | A1 | 10/2010 | Jacobs | |
| 2011/0021746 | A1 | 1/2011 | Cappuccilli | |
| 2011/0038866 | A1 | 2/2011 | Hastewell | |
| 2011/0053842 | A1 | 3/2011 | Camphausen | |
| 2011/0081345 | A1 | 4/2011 | Moore | |
| 2011/0118144 | A1 | 5/2011 | Hyun | |
| 2011/0124527 | A1 | 5/2011 | Cappuccilli | |
| 2011/0274623 | A1 | 11/2011 | Jacobs | |
| 2011/0287009 | A1 | 11/2011 | Scheer | |
| 2012/0225870 | A1 | 9/2012 | Janne | |
| 2012/0244164 | A1 | 9/2012 | Beste | |
| 2012/0263723 | A1 | 10/2012 | Davies | |
| 2012/0270797 | A1 | 10/2012 | Wittrup | |
| 2012/0315639 | A1 | 12/2012 | Deng | |
| 2012/0321666 | A1 | 12/2012 | Cooper | |
| 2013/0012435 | A1 | 1/2013 | Camphausen | |
| 2013/0039927 | A1 | 2/2013 | Dewhurst | |
| 2013/0079243 | A1 | 3/2013 | Diem | |
| 2013/0130377 | A1 | 5/2013 | Lee | |
| 2013/0184212 | A1 | 7/2013 | Camphausen | |
| 2013/0226834 | A1 | 8/2013 | Gannalo, II | |
| 2013/0273561 | A1 | 10/2013 | Walker | |
| 2014/0141000 | A1 | 5/2014 | Chiu | |
| 2014/0155325 | A1 | 6/2014 | Mark | |
| 2014/0155326 | A1 | 6/2014 | Mark | |
| 2014/0255408 | A1 | 9/2014 | Chiu | |
| 2014/0271467 | A1 | 9/2014 | Hackel | |
| 2014/0341917 | A1 | 11/2014 | Nastri | |
| 2014/0349929 | A1 | 11/2014 | Camphausen | |
| 2014/0371296 | A1 | 12/2014 | Bennett | |
| 2015/0005364 | A1 | 1/2015 | Chae | |
| 2015/0104808 | A1 | 4/2015 | Goldberg | |
| 2015/0118288 | A1 | 4/2015 | Lee | |
| 2015/0191543 | A1 | 7/2015 | Wu | |
| 2015/0197571 | A1 | 7/2015 | Freeman | |
| 2015/0203580 | A1 | 7/2015 | Papadopoulos | |
| 2015/0210756 | A1 | 7/2015 | Torres | |
| 2015/0252097 | A1 | 9/2015 | Camphausen | |
| 2015/0274835 | A1 | 10/2015 | Marasco | |
| 2015/0346208 | A1 | 12/2015 | Couto | |
| 2015/0355184 | A1 | 12/2015 | Pierce | |
| 2016/0041182 | A1 | 2/2016 | Diem | |
| 2016/0303256 | A1 | 10/2016 | Liu | |
| 2016/0326232 | A1 | 11/2016 | Rosa | |
| 2016/0347840 | A1 | 12/2016 | Anderson | |
| 2016/0355599 | A1 | 12/2016 | Sagert | |
| 2017/0174748 | A1 | 6/2017 | Mitchell | |
| 2017/0258948 | A1 | 9/2017 | Morin | |
| 2017/0348397 | A1 | 12/2017 | Diem | |
| 2017/0362301 | A1 | 12/2017 | Anderson | |
| 2018/0162927 | A1 | 6/2018 | Hawkins | |
| 2019/0127444 | A1 | 5/2019 | Brezski | |
| 2019/0175651 | A1 | 6/2019 | Lee | |
| 2019/0184018 | A1 | 6/2019 | Manoharan | |
| 2019/0184028 | A1 | 6/2019 | Dudkin | |
| 2019/0202927 | A1 | 7/2019 | Sagert | |
| 2019/0256575 | A1 | 8/2019 | Chen | |
| 2019/0263915 | A1 | 8/2019 | Goldberg | |
| 2019/0330361 | A1 | 10/2019 | Chin | |
| 2021/0032312 | A1 | 2/2021 | Hawkins | |
| 2023/0143550 | A1 | 5/2023 | Hawkins | |

FOREIGN PATENT DOCUMENTS

| | | | |
|---|---|---|---|
| CN | 105907719 | A | 8/2016 |
| EP | 0985039 | A2 | 3/2000 |
| EP | 1137941 | A1 | 10/2001 |
| EP | 1210428 | A1 | 6/2002 |
| EP | 1266025 | A1 | 12/2002 |
| EP | 2935329 | A1 | 10/2015 |
| JP | 2011507543 | A | 3/2011 |
| JP | 2011517314 | A | 6/2011 |
| JP | 2011520961 | A | 7/2011 |
| JP | 2011522517 | A | 8/2011 |
| JP | 2012507295 | A | 3/2012 |
| JP | 2014530014 | A | 11/2014 |
| JP | 2016504291 | A | 2/2016 |
| KR | 20160067966 | A | 4/2016 |
| RU | 2012151366 | | 6/2014 |
| WO | 9638557 | A1 | 12/1996 |
| WO | 2001014557 | A1 | 3/2001 |
| WO | 0164942 | A1 | 9/2001 |
| WO | 0232925 | A2 | 4/2002 |
| WO | 03104418 | A2 | 12/2003 |
| WO | 2004029224 | A2 | 4/2004 |
| WO | 2004058821 | A2 | 7/2004 |
| WO | 2005018534 | A2 | 3/2005 |
| WO | 2005042708 | A2 | 5/2005 |
| WO | 2007000671 | A2 | 1/2007 |
| WO | 2007085815 | A2 | 8/2007 |
| WO | 2008066752 | A2 | 6/2008 |
| WO | 2008079973 | A2 | 7/2008 |
| WO | 2008127710 | A2 | 10/2008 |
| WO | 2008156642 | A1 | 12/2008 |
| WO | 2009023184 | A2 | 2/2009 |
| WO | 2009058379 | A2 | 5/2009 |
| WO | 2009083804 | A2 | 7/2009 |
| WO | 2009085462 | A1 | 7/2009 |
| WO | 2009086116 | A2 | 7/2009 |
| WO | 2009102421 | A2 | 8/2009 |

(56) References Cited

FOREIGN PATENT DOCUMENTS

| | | | |
|---|---|---|---|
| WO | 2009111691 | A2 | 9/2009 |
| WO | 2009126834 | A2 | 10/2009 |
| WO | 2009133208 | A1 | 11/2009 |
| WO | 2009142773 | A2 | 11/2009 |
| WO | 2010039248 | A1 | 4/2010 |
| WO | 2010051274 | A2 | 5/2010 |
| WO | 2010051310 | A2 | 5/2010 |
| WO | 2010060095 | A1 | 5/2010 |
| WO | 2010093627 | A2 | 8/2010 |
| WO | 2010115202 | A2 | 10/2010 |
| WO | 2010115551 | A1 | 10/2010 |
| WO | 2011005133 | A1 | 1/2011 |
| WO | 2011110642 | A2 | 9/2011 |
| WO | 2011130324 | A1 | 10/2011 |
| WO | 2011131746 | A2 | 10/2011 |
| WO | 2011137319 | A2 | 11/2011 |
| WO | 2011151412 | A1 | 12/2011 |
| WO | 2012016245 | A2 | 2/2012 |
| WO | 2012162418 | A1 | 11/2012 |
| WO | 2013049275 | A1 | 4/2013 |
| WO | 2014081944 | A2 | 5/2014 |
| WO | 2014081954 | A1 | 5/2014 |
| WO | 2014100079 | A1 | 6/2014 |
| WO | 2014165082 | A2 | 10/2014 |
| WO | 2014165093 | A2 | 10/2014 |
| WO | 2014189973 | A2 | 11/2014 |
| WO | 2014209804 | A1 | 12/2014 |
| WO | 2015057545 | A2 | 4/2015 |
| WO | 2015061668 | A1 | 4/2015 |
| WO | 2015089073 | A2 | 6/2015 |
| WO | 2015092393 | A2 | 6/2015 |
| WO | 2015109124 | A2 | 7/2015 |
| WO | 2015143199 | A1 | 9/2015 |
| WO | 2015195163 | A1 | 12/2015 |
| WO | 2016000619 | A1 | 1/2016 |
| WO | 2016004043 | A1 | 1/2016 |
| WO | 2016086021 | A1 | 6/2016 |
| WO | 2016086036 | | 6/2016 |
| WO | 2016179534 | | 11/2016 |
| WO | 2016197071 | A1 | 12/2016 |
| WO | 2017011618 | A1 | 1/2017 |
| WO | 2017223180 | A2 | 12/2017 |

OTHER PUBLICATIONS

Hurtado et al., "Potential role of 4-1 BB in T cell Activation Comparison with the Costimulatory Molecule CD28", Journal of Immunology, vol. 155, pp. 3360-3367, 1995.

Hurtado et al., "Signals through 4-1BB are Costimulatory to previously activated splenic T cells and inhibit activation-induced cell death", Journal of Immunology, vol. 158, pp. 2600-2609, 1997.

Hylarides et al., "Preparation and in Vivo Evaluation of an N-9p-[1251]1odophenethyl) maleimide—Antibody Conjugate" Bioconjugate Chem., vol. 2, pp. 435-440, 1991.

Hynes et al., "ERBB Receptors and Cancer: the Complexity of Targeted Inhibitors," Nature Reviews, vol. 5, pp. 341-356 (2005).

Ichimura et al., "Expression of c-met/HGF Receptor in Human Non-small cell lung carcinomas in vitro and in vivo and its prognostic significance," Japan Journal of Cancer Research 87:1063-69 (1996).

Irwin D. Kuntz, "Structure-based strategies for drug design and discovery," Science, 257(5073): 1078-1082 (1992).

Itoh, et al., "Application of Inverse Substrates to Trypsin-Catalyzed Peptid Synthesis", Bioorganic Chemistry (1996) 24, 0007, pp. 59-68.

Jacobs et al, "Fusion to a highly stable consensus albumin binding domain allows for tunable pharmacokinetics", Protein Engineering, Design and Selection, vol. 28, No. 10, pp. 385-393 (2015).

Jacobs et al. Design of novel FN3 domains with high stability by a consensus sequence approach. Protein Engineer Design Selection 25(3): 107-117, 2012.

Jacobs et al., "FN3 Domain Engineering", Protein Engineering, pp. 145-162, 2012.

Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).

Karatan, et al., "Molecular Recognition Properties of FN3 Mono bodies that Bind the Src SH3 Domain," Chemistry & Biology, 11: 835-844 (2004).

Klein et al., "Bispecific centyrin simultaneously targeting EGFR and c-Met demonstrates improved activity compared to the mixture of single agents," Cancer Res 73(8 Suppl): Abstract LB-312, Apr. 2013.

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).

Koide et al., "High-affinity single-domain binding proteins with a binary-code interface," PNAS, vol. 104, No. 16, pp. 6632-6637 (Apr. 17, 2007).

Koide, et al., "The Fibronectin Type III Domain as a Scaffold for Novel Binding Proteins," Journal of Molecular Biology, 284: 1141-1151 (1998).

Koide, et al., Teaching an Old Scaffold New Tricks: Monobodies Constructed Using Alternative Surfaces of the FN3 Scaffold, Journal of Molecular Biology, 415: 393-405 (2012).

Koivunen et al. Identification of Receptor Ligands with Phage Display Peptide Libraries J Nucl Med; 40:883-888, 1999.

Kumaran et al., "Confrmationally driven protease-catalyzed splicing of peptide segments: V8 protease-mediated syntheses of fragments derived from thermolysin and ribonucléase A", Protein Science, (1997) 6: pp. 2233-2241.

Kunkel et al., "Rapid and Efficient Site-Specific Mutagenesis without Phenotypic Selection", Methods in Enzymology, (1987) vol. 154 pp. 367-375.

Kwon et al., cDNA sequences of two inducible T-cell genes, Proc. Natl. Acad. Sci., vol. 86, pp. 1963-1967, Mar. 1989.

Langstein et al., "CD137 (ILA/4-1BB), a Member of the TNF Receptor Family, Induces Monocyte Activation via Bidirectional Signaling," The Journal of Immunology, vol. 160, pp. 2488-2494 (1998).

Langstein et al., "CD137 Induces Proliferation and Endomitosis in Monocytes," Blood, vol. 94, No. 9, pp. 3161-3168 (1999).

Langstein et al., "Identification of CD137 as a potent monocyte survival factor", Journal of Leukocyte Biology, vol. 65, pp. 829-833, Jun. 1999.

Lazar et al., "Transforming growth factor alpha: mutation of aspartic acid 47 and leucine 48 results in different biological activities", Mol Cell Biol. 8:1247-1252 (1988).

Lee et al., "A Glu-ruea-Lys Ligand-conjugated Lipid nanoparticle/siRNA systen inhibits Androgen Receptor Expression in vivo," Molecular Therapy-Nucleic Acids e348:1-11 (2016).

Lee et al., "4-1BB Promotes the Survival of CD8+ T Lymphocytes by Increasing Expression of Bcl-XL and Bf1-11," The Journal of Immunol., vol. 169, pp. 4882-4888 (2002).

Lehmann et al., Engineering proteins for thermostability the use of sequence alignments versus rational design and directed evolution, Current Opinion in Biotechnology, vol. 12, pp. 371-375 (2001).

Lejon et al., "Structural basis for the binding of naproxen to human serum albumin in the presence of fatty acids and he GA module", Acta Cryst. (2008) F pp. 64-69.

Lepenies et al., "The Role of Negative Costimulators Dunng Parasitic Infections," Endocrine, Metabolic & Immune Disorders—Drug Targets, vol. 8, pp. 279-288 (2008).

Li et al., "Skin toxicities associated with epidermal growth factor receptor inhibitors," Target Oncology, vol. 4, pp. 107-119 (2009).

Linardou, et al., "Somatic EGFR mutations and efficacy of tyrosine kinase inhibitors in NSCLC," National Review of Clinical Oncology, 6: 352-366 (2009).

Lipovsek, et al., "Evolution of an Interloop Disulfide Bond in High-Affinity Antibody Mimics Based on Fibronectin Type III Domain and Selected by Yeast Surface Display: Molecular Con-

(56) References Cited

OTHER PUBLICATIONS vergence with Single-Domain Camelid and Shark Antibodies," Journal of Molecular Biology, 368: 1024-1041 (2007).
Lohse et al., Fluorescein-Conjugated Lysine monomers for Solid Phase Synthesis of Fluorescent Peptides and PNA Pligomers Bioconjugate Chem, vol. 8, pp. 503-509, 1997 .pdf.
Ma et al., "c-Met: Structure, functions and potential for therapeutic inhibition," Cancer and Metastasis Reviews, 22:309-325 (2003).
Maatta et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).
Makkouk Amani; Chester Cariad; Kohrt Holbrook E., "Rationale for anti-CD137 cancer immunotherapy", European Journal of Cancer, Elsevier, Amsterdam NL, Amsterdam NL , (Jan. 2, 2016), vol. 54, doi:10.1016/j.ejca.2015.09.026, ISSN 0959-8049, pp. 112-119, XP029401784.
Mamluk et al., "Anti-tumor effect of CT-322 as an Adnectin inhibitor of vascular endothelial growth factor receptor-2", mAbs, 2(2), pp. 199-208, 2010.
Mattheakis et al., "An in vitro polysome display system for identifying ligands from very large peptide libraries", Proc. Natl. Acad. Sci. (1994) Vo.. 91, pp. 9022-9026.
Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.
McCracken, "Non-invasive monitoring of hematopoietic reconstitution and immune cell function through Positron Emission Tomography" University of California, Los Angeles, Dissertaton ProQuest LLC (2014) pp. 1-202.
McLaughlin et al., "Quantitative Assessmenet of the Heterogeneity of PD-L 1 Expression in Non-small Cell Lung Cancer (NSCLC)," Jama Oncol., vol. 2, No. 1, pp. 46-54, (Jan. 2016).
Meinke et al., "Cellulose-Binding Polypeptides from Cellulomonas fimi: Endoglucanase D (CenD), a Family A b-1,4-Glucanase," Journal of Bactenology, vol. 175, No. 7, pp. 1910-1918 (1993).
Mendelsohn et al., "Epidermal Growth Factor Receptor Targeting in Cancer," Seminars in Oncology, vol. 33, pp. 369-385 (2006).
Mendelsohn, et al., "The EGF receptor family as targets for cancer therapy," Oncogene, 19: 6550-6565 (2000).
Michel et al., "A soluble form of CD137 (ILA/4-1BB), a member of the TNF receptor family, is released by activated ymphocytes and is detectable in sera of patients with rheumatoid arthritis," Eur. J_ Immunol., vol. 28, 290-295 1998).
Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 (2011).
Alderson et al., "Molecular and Biological Characterization of Human 4-1 BB and its Ligand", Eur. J_ Immunol., vol. N, pp. 2219-2227, 1994.
Alfthan, et al., "Properties of a single-chain antibody containing different linker peptides," Protein Engineering, 8(7):725-731 (1995).
Attwood TK. Genomics. The Babel of bioinformatics. Science. 290(5491 ):471-473, 2000.
Baselga, et al., "Critical Update and Emerging Trends in Epidermal Growth Factor Receptor Targeting in Cancer," Journal of Clinical Oncology, 23(11): 2445-2459 (2005).
Bass, et al., "Hormone Phage: An Enrichment Method for Variant Proteins with Altered Binding Properties," Proteins: Structure, Function, and Genetics, 8: 309-314 (1990).
Batley et al., "Inhibition of FGF-1 Receptor Tyrosine Kinase Activity by PD 161570, a New Protein-Tyrosine Kinase nhibitor," Life Sciences, vol. 62, No. 20, pp. 143-150 (1998).
Bean, et al., "MET amplification occurs with or without T790M mutations in EGFR mutant lung tumors with acquired resistance to gefitinib or erlotinib," Proceedings of the National Academy of Science, 104(52): 20932-20937 (2007).
Binz et al., "High-affinity binders selected from designed ankyrin repeat protein libraries," Nature Biotechnology, vol. 22, No. 5, pp. 575-585 (May 2004).
Binz, et al., "Engineered proteins as specific binding reagents," Current Opinion in Biotechnology, 16: 459-469 (2005).
Birtalan et al., "The Intrinsic Contributions of Tyrosine, Serine, Glycine and Arginine to the Affinity and Specificity of Antibodies", Journal of Molecular Biology, vol. 377, Issue 5, pp. 1518-1528, Apr. 2008.
Bork et al., "Proposed acquisition of an animal protein domain by bacteria," Proceedings of the National Academy of Science, USA, vol. 89, pp. 8990-8994 (1992).
Brown et al., "Tolerance of single, but not multiple, amino acid replacements in antibody VH CDR 2: a means of minimizing B cell wastage from somatic hypermutation", J. Immuno. (1996) pp. 3285-3291.
Burgess et al., "Possible dissociation of the heparin-binding and mitogenic activities of heparin-binding (acidic fibroblast) growth factor-1 from its receptor-binding activities by site-directed mutagenesis of a single lysine residue" J Cell Biol (1990) 111:pp. 2129-2138.
Burton Earle Barnett et al, "Development of Novel Non-Immunoglobulin Centyrin-Based Cars (CARTyrins) Targeting Human Bcma", Blood 128(22) (2016).
Burton Earle Barnett, Xinxin Wang, David L. Hermanson, Yening Tan, Eric M. Osertag, Devon J. Shedlock, "Disclosures", Blood, American Society of Hematology, US, US , (Dec. 2, 2016), vol. 128, No. 22, doi:10.1182/blood.V128.22.4557.4557, ISSN 0006-4971, pp. 4557-4557, XP055711182.
Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.
Cappuzzo, et al., "Epidermal Growth Factor Receptor Gene and Protein and Gefitinib Sensitivity in Non-small-Cell Lung Cancer," Journal of the National Cancer Institute, 97: 643-655 (2005).
Chen et al., "Cell-Surface Display of Heterologous Proteins: From High-Throughput Screening to Environmental Applications", Biotechnology and Bioengineering, (2002) vol. 79, No. 5, pp. 496-503.
Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.
Christensen, et al., "c-Met as a target for human cancer and characterization of inhibitors for therapeutic intervention," Cancer Letters, 225: 1-26 (2005).
Clarke, et al., "Folding and Stability of a Fibronectin Type III Domain of Human Tenascin," Journal of Molecular Biology, 270: 771-778 (1997).
Cooper et al., "4-1 BB (CD 137) controls the clonal expansion and survival of COB T cells in vivo but does not t: ontribute the development of cytotoxicity", Eur. J_ Immunol., vol. 32, pp. 521-529, 2002.
Cooper et al., "Molecular cloning of a new transforming gene from a chemically transformed human cell line," Nature, vol. 311, pp. 29-33 (1984).
Cota, et al., "Two Proteins with the Same Structure Respond very Differently to Mutation: The Role of Plasticity in protein Stability", Journal of Molecular Biology, 302, 713-725 (2000).
DeBenedette et al., "Role of 4-1BB Ligand in Costimulation of T Lymphocyte Growth and its Upregulation on M12 B rymphomas by cAMP," J_ Exp_ Med., vol. 181, pp. 985-992 (1995).
Dehouck, et al., "Fast and accurate predictions of protein stability changes upon mutations using statistical potentials and neural networks: PoPMuSiC-2.0, Bioinformatics," 25(19): 2537-2543 (2009).
DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).
Diem et al., "Selection of high-affinity Centyrin FN3 domains from a simply library diversified at a combination of strand and loop positions." Protein Engin Design (2014) Selection 27(10): 419-429.

(56) References Cited

OTHER PUBLICATIONS

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).
Downward et al., "Autophosphorylation sites on the epidermal growth factor receptor," Nature, vol. 311, pp. 483-485 (1984).
Dutta, et al., "High-affinity fragment complementation of a fibronectin type III domain and its application to stability enhancement," Protein Science, 14: 2838-2848 (2005).
Engelman et al., "MET Amplification Leads to Gefitinib Resistance in Lung Cancer by Activating ERBB3 Signaling," Science, vol. 316, pp. 1039-1043 (2007).
Ferguson, Kathryn M., "Structure-Based View of Epidermal Growth Factor Receptor Regulation," Annual Review of Biophysics, vol. 37, pp. 353-373 (2008).
Garcia-Lbilcieta, et al., "Simple method for production of randomized human tenth fibronectin domain III libraries for use in combinatorial screening procedures," Bio Technologies, 44: 559-562 (2008).
Garon et al., "Pembrolizumab for the Treatment of Non-Small-Cell Lung Cancer," The New England Journal of Medicine, vol. 372, No. 21, pp. 2018-2028 (May 21, 2015).
Garrard et al., "Selection of an anti-IGF-1 Fab from a Fab phage library created by mutagenesis of multiple CDR loops," Gene, 128: 103-109 (1993).
GenBank Accession No. NP 002151, (2013).
GenBank Accession No. NP 001120972, Jun. 30, 2018.
Getmanova, et al., "Antagonists to Human and Mouse Vascular Endothelial Growth Factor Receptor 2 Generated by Directed Protein Evolution In Vitro," Chemistry & Biology, 13: 549-556 (2006).
Gill, et al., "Monoclonal Anti-epidermal Growth Factor Receptor Antibodies Which Are Inhibitors of Epidermal Growth Factor Binding and Antagonists of Epidermal Growth Factor-stimulated tyrosine Protein Kinase Activity," The Journal of Biological Chemistry, 259(12): 7755-7760 (1984).
Goldberg et al., "Engineering a Targeted Delivery Platform using Centyrins" Protein Engineering, Design & Selection, vol. 29, No. 12, pp. 563-572, 2016.
Goldstein, et al., "Biological efficacy of a chimeric antibody to the epidermal growth factor receptor in a human tumor xenograft model," Clinical Cancer Research, 1: 1311-1318 (1995).
Gramaglia et al., "Co-stimulation of antigen-specific CD4T cells by 4-1BB ligand, Eur. J. Immunol., vol. 30, p. ô €?" 92-402 (2000).
Grunwald et al., "Developing Inhibitors of the Epidermal Growth Factor Receptor for Cancer Treatment," Journal of the National Cancer Institute, vol. 95, No. 12, pp. 851-867 (2003).
Hackel et al., "Use of 64Cu-Labeled Fibronectin Domain with EGFR-Overexpressing Tumor Xenograft: Molecular Imaging1", Radiology (2012) vol. 263:No. 1 pp. 179-188.
Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).
Hackel, et al., "Stability and CDR Composition Biases Enrich Binder Functionality Landscapes," Journal of Molecular Biology, 401: 84-96 (2010).
Hallewell et al., "Genetically Engineered Polymers of Human CuZN Superoxide Dismutase," The Journal of Biological Chemistry, vol. 264, No. 9, pp. 5260-5268 (1989).
Hamill et al., "The Effect of Boundary Selection on the Stability and Folding of the Third Fibronectin Type III Domain from Human Tenascin", Biochemistry, 37: 8071-8079 (1998).
Michel et al., "CD137-induced apoptosis is independent of CD95," Immunology, vol. 98, pp. 42-46 (1999).
Michel et al., "Expression of soluble CD137 correlates with activation-induced cell death of lymphocytes", Cytokine, vol. 12, No. 6, pp. 742-746, 2000.
Miller, et al., "Ligand binding to proteins: the binding landscape model," Protein Science, 6(10): 2166-2179 (1997).
Murota, H. et al., "Exacerbating factors of itch in atopic dermatitis," Allergology International, 2017, No. 66:8-13.
Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.
NCBI Reference Sequence NP _005219.2, "Epidermal Growth Factor Receptor Isoform a Precursor [*Homo sapiens*]," pp. 1-14 (May 18, 2014).
Odegrip et al., "CIS display: In vitro selection of peptides from libraries of protein-DNA complexes", Proc Natl Acad Sci USA, vol. 101, No. 9, pp. 2806-2810, Mar. 2004.
Olson et al., "Design, expression, and stability of a diverse protein library based on the human fibronectin type III domain," Protein Science, vol. 16, 476-484 (2007).
Olson, William C. et al., "Antibody-drug Conjugates Targeing Prostate-Specific Membrane Antigen," Frontiers in Bioscience (Landmark Edition) 19: pp. 12-33, Jan. 1, 2014.
Pace, "Determination and Analysis of Urea and Guanidine Hydrochloride Denaturation Curves", Methods in Enzymology (1986) vol. 131, pp. 266-280.
Panek et al.,"In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444 (1997).
Parker, et al., "Antibody mimics based on human fibronectin type three domain engineered for thermostability and high-affinity binding to vascular endothelial growth factor receptor two," Protein Engineering, Design & Selection, 18(9):435-444 (2005).
Pauly et al., CD137 is expressed by follicular dendritic cells and costimulates B lymphocyte activation in germinal t; enters, Journal of Leukocyte Biology, vol. 72, pp. 35-42, Jul. 2002.
Peters et al., "MET: a promising anticancer therapeutic target," Nature Reviews Clinical Oncology, vol. 9, pp. 314-326 (2012).
Prewett et al., "Mouse-Human chimeric Anti-Epidermal Growth Factor Receptor Antibody C225 Inhibits the Growth Jf Human Renal Cell Carcinoma Xenografts in Nude Mice," Clinical Cancer Research, vol. 4, pp. 2957-2966 (1998).
Reiss, et al., "Inhibition of platelet aggregation by grafting RGD and KGD sequences on the structural scaffold of small disulfide rich proteins," Platelets, 17(3): 153-157 (2006).
Riely, et al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, 12(3): 839-844 (2006).
Roberts et al., "RNA-peptide fusions for the in vitro selection of peptides and proteins," Proceedings of the National Academy of Science USA, vol. 94, pp. 12297-12302 (1997).
Robinson et al., "Covalent Attachment of Arc Repressor Subunits by a Peptide Linker Enhances Affinity for Operator DNA," Biochemistry, vol. 35, pp. 109-116 (1996).
Rudikoff et al., "Single amino acid substitution altering antigen-binding specificity," Proc Natl Acad Sci USA 79:1979-1983(1982).
Rybalov et al., "PSMA, EpCAM, VEGF and G RPR as Imaging Targets in Locally Recurrent Prostate Cancer after Radiotherapy", Int. J. Mol. Sci. (2014) 15, pp. 6046-6061.
Safdari Y. et al., "Antibody humanization methods-a review and update," Biotechnology and Genetic Engineering Reviews 29(2):175-186 (2013).
Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).
Schmidt et al., "Novel mutations of the MET proto-oncogene in papillary rental carcinomas," Oncogene, vol. 18, pp. 2343-2350 (1999).
Schwarz et al., "ILA, a Member of the Human Nerve Growth Factor/Tumor Necrosis Factor Receptor Family, Regulates T-Lymphocyte Proliferation and Survival," Blood, vol. 87, No. 7, pp. 2839-2845 (Apr. 1, 1996).
Shalom D. Goldberg, Rosa M.F. Cardoso, Tricia Lin, Tracy Spinka-Doms, Donna Klein, Steven A. Jacobs, Vadim Dudkin, Gary Gilliland, Karyn T. O'neil, "Engineering a targeted delivery platform

(56) References Cited

OTHER PUBLICATIONS using Centyrins", Protein Engineering, Design and Selection, Oxford Journal, London, GB, GB , doi:10.1093/protein/gzw054, ISSN 1741-0126, XP055384705.
Shen J. et al., "Single variable domain-IgG fusion: a novel recombinant approach to Fc domain-containing bispecific antibodies," Journal of Biological Chemistry 281(16):10706-10714 (2006).
Shuford et al., "4-18B Costimulatory Signals Preferentially Induce COB+ T Cell Proliferation and Lead to the amplification In Vivo of Cytotoxic T Cell Responses," J_ Exp_ Med., vol. 186, No. 1, pp. 47-55 (Jul. 7, 1997).
Siegfried et al., "The Clinical Significance of Hepatocyte Growth Factor for Non-Small Cell Lung Cancer," Annals of Thoracic Surgery, vol. 66, pp. 1915-1918 (1998).
Sierra et al., "c-Met as a potential therapeutic target and biomarker in cancer," Therapeutic Advances in Medical Oncology, vol. 3, No. 51, pp. 521-535 (2011).
Siggers et al. Conformational dynamics in loop swap mutants of homologous fibronectin type III domains. Biophys J. Oct. 1, 2007 ;93(7):2447-56.
Skerra, et al., "Engineered protein scaffolds for molecular recognition," Journal of Molecular Recognition, 13: 167-187 (2000).
Skolnick, et al., "From genes to protein structure and function: novel applications of computational approaches in the genomic era," Trends Biotechnology, 18(1):34-39 (2000).
Slonomics® Technology Website "https://www.morphosys.com/science/drug-development-capabilities/slonomics", May 12, 2020.
Smith, "Filamentous fusion phage: novel expression vectors that display cloned antigens on the virion surface.", Association of Science (1985) vol. 228, pp. 1315(3).
Song et al. Cancer stem cells—an old idea that's new again: implications for the diagnosis and treatment of breast cancer. Expert Opin Biol Ther 7:4):431-438, 2007.
Stamos et al., "Crystal structure of the HGF b-chain in complex with the Sema domain of the Met receptor," The EMBO Journal, vol. 23, pp. 2325-2335 (2004).
Steiner, et al., "Efficient Selection of DARPins with Sub-nonomolar Affinities using SRP Phage Display," Journal of Molecular Biology, 382: 1211-1227 (2008).
Strand et al., "Site-Specific Radioiodination of HER2-Targeting Affibody Molecules using 4-Iodophenethylmaleimide Decreases Renal Uptake of Radioactivity"; Chemitry Open, vol. 4, pp. 174-182, 2015.
Strohl, William R., "Optimization of Fe-mediated effector functions of monoclonal antibodies," Current Opinion in Biotechnology, vol. 20, pp. 685-691 (2009).
SwissProt Accession No. P00533.2, "Epidermal Growth Factor Receptor," pp. 1-49 (Jun. 11, 2014).
Takahashi et al., "Cutting Edge: 4-1BB Is a Bona Fide CD8 T Cell Survival Signal," J Immunol., vol. 162, pp. 5037-5040 (1999).
Tang et al, "Anti-Transferrin Receptor-Modified Amphotericin B-Loaded PLA-PEG Nanoparticles Cure Candidal Meningitis and Reduce Durg Toxicity," Oct. 5, 2015, International Journal of Medicine, 2015:10, pp. 6227-6241.
Tannock and Hill. The Basic Science of Oncology. 1998. New York: McGraw-Hill;; pp. 357-358.
Teplyakov A. et al., "Antibody modeling assessment II. Structures and models," Proteins: Structure, Function, and Bioinformatics 82 (8):1563-1582 (2014).
Tie et al., "Safety and efficacy of nivolumab in the treatment of cancers: A meta-analysis of 27 prospective clinical rials," International Journal of Cancer, vol. 140, pp. 948-958, (2017).
Torres M. et al., "The immunoglobulin constant region contributes to affinity and specificity," Trends in immunology 29(2):91-97 (2008).
Turke et al., "Preexistence and Clonal Selection of MET Amplification in EGFR Mutant NSCLC," Cancer Cell, vol. 17, pp. 77-88 (2010).
Ullrich, et al., "Human epidermal growth factor receptor cDNA sequence and aberrant expression of the amplified gene in A431 epidermoid carcinoma cells," Nature, 309: 418-425 (1984).
UniProt Accession No. P10039. (2013).
Vajdos et al., "Comprehensive funtional maps of the antigen-binding site of an anti-ErbB2 antibody obtained with shotgun scanning mutagenisis", J. Mol. Biol. (2002) 32(2): pp. 415-428.
Van den Burg et al., "Selection of mutations for increased protein stability", Curr. Opin. Biotech. 13:333-337 (2002).
Wang et al., "VISTA, a novel mouse Ig superfamily ligand that negatively regulates T cell responses," Journal of Experimental Medicine, vol. 208, No. 3, pp. 577-592 (Mar. 14, 2011).
Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).
Wattanachaisaereekul, "Production of Polyketides by *Saccharomyces cerevisiae*", Ph.D. Thesis (2007) Center for Microbial Biotechnology, BioCentrum-DTU Technical University of Denmark, pp. 1-187.
Xu, et al., "Directed Evolution of High-Affinity Antibody Mimics Using mRNA Display," Chemistry & Biology, 9: 933-942 [2002).
Zhang et al., "Complete disulfide bond assignment of a recombinant immunoglobulin G4 monoclonal antibody," Analytical Biochemistry, vol. 311, pp. 1-9 (2002).
Zhou et al., "Characterization of human homologue of 4-1BB and its ligand", Immunology Letters, vol. 45, pp. 67-73, 1995.
Zucali, et al., "Role of cMET expression in non-small-cell lung cancer patients treated with eGFR tyrosine kinase inhibitors", Annals of Anocology (2008) 19:: 1605-1612.

* cited by examiner 300,000 CMV reactive PBMCs/well
Anti-CD8 @ 1 uM 300,000 CMV reactive PBMCs/well
Anti-CD8 @ 1 uM 300,000 M1 reactive PBMCs/well
Anti-CD8 @ 1 uM 300,000 M1 reactive PBMCs/well
Anti-CD8 @ 1 uM

365 does not increase IFNγ production in absence of pp65 peptide

6 day stimulation

365 does not affect pp65 peptide induced IFNγ production

6 day stimulation

CD8A-BINDING FIBRONECTIN TYPE III DOMAINS

CROSS-REFERENCE TO RELATED APPLICATIONS

This application is a continuation of U.S. patent application Ser. No. 17/689,869, filed Mar. 8, 2022 (now allowed), that is a continuation of U.S. patent application Ser. No. 16/821,064, filed Mar. 17, 2020, now U.S. Pat. No. 11,299,534 B2, issued Apr. 12, 2022, that is a continuation of U.S. patent application Ser. No. 15/839,915, filed Dec. 13, 2017, now U.S. Pat. No. 10,626,165 B2, issued Apr. 21, 2020, and claims priority to U.S. Provisional Application No. 62/434,017, filed Dec. 14, 2016. Each disclosure is incorporated herein by reference in its entirety.

REFERENCE TO SEQUENCE LISTING SUBMITTED ELECTRONICALLY

This application contains a sequence listing, which is submitted electronically. The contents of the electronic sequence listing (065768.12US4 Sequence Listing.xml; Size 399,942 bytes; and Date of Creation: May 14, 2024) is herein incorporated by reference in its entirety.

TECHNICAL FIELD

The present invention relates to fibronectin type III (FN3) domains that specifically bind to cluster of differentiation 8a (CD8a). Such FN3 domains may be used for example, for medical imaging, diagnostics, and pharmaceutical therapy. Methods for the production of such molecules and diagnostic agents comprising them are also provided.

BACKGROUND

The rapidly evolving fields of cancer immunotherapy have recently led to the FDA approval of several new immunotherapies, with many more therapies presently in clinical trials for a variety of cancers. Furthermore, cellular, small molecule, antibody-based immunotherapies, and combinations thereof, are being rigorously tested preclinically for clinical translation. The dynamic tumor microenvironment and tumor heterogeneity have become important topics in both preclinical and clinical studies (Hanahan D, Weinberg R A. Cell 2011; 144: 646-74; Mantovani A, Allavena P, Sica A, Balkwill F. Nature 2008; 454:436-44; Schreiber R D, Old L J, Smyth M J. Science 2011; 331:1565-70.), but the ability to monitor changes in the immune status of primary lesions and metastatic cancers is limited. Current methods to monitor lymphocytes from whole blood or biopsies from heterogeneous tumors do not reflect the dynamic and spatial information likely required to monitor immune responses to therapeutic intervention, many of which elicit whole body changes in immune cell numbers and localization. Therefore, molecular imaging methods that can noninvasively monitor both systemic and intratumoral alterations in immune cell numbers or localization during experimental therapies have the ability to increase the understanding of the dynamics of immunotherapeutic mechanism with the potential to provide translatable methods for predicting and/or assessing clinical immunotherapeutic responses.

Analysis of tumor-infiltrating lymphocytes (TIL) has demonstrated the importance of tumor immune microenvironment and that the presence of cytotoxic $CD8^+$ T cells can predict overall survival in breast, lung, ovarian, melanoma, and colorectal cancers (reviewed in refs. Pages F, et al. Oncogene 2010; 29:1093-102 And Gooden M J, et al. Br J Cancer 2011; 105: 93-103.). With the recent clinical successes of immunotherapies that alter the tumor immune microenvironment, including adoptive cell transfer (ACT) of T-cell receptor (TCR)- or chimeric antigen receptor-transduced cytotoxic T cells (Johnson L A, et al. Blood 02009; 114: 535-46; Rosenberg S A. Sci Transl Med 2012; 4:127ps8.), agonistic antibodies targeting CD137 (4-1BB) and CD40 (Melero I, et al. Clin Cancer Res 2013; 19:997-1008; Melero I, et al. Nat Rev Cancer 2007; 7: 95-106; Vinay D S, and Kwon B S. Mol Cancer Ther 2012; 11:1062-70.), and antibody blockade of the checkpoint inhibitors CTLA-4, PD-1, and PD-L1 (Callahan M K, and Wolchok, J D. J Leukoc Biol 2013; 94:41-53; Shin D S, and Ribas A. Curr Opin Immunol 2015; 33C:23-35; Topalian S L, et al. Cancer Cell 2015; 27:450-61.), the ability to noninvasively monitor the tumor immune response to therapy has become of upmost importance.

SUMMARY

The present invention comprises CD8A-binding fibronectin type III (FN3) domains. Also described are related polynucleotides capable of encoding the provided FN3 domains, cells expressing the provided FN3 domains, as well as associated vectors. In addition, methods of using the provided FN3 domains are described. For example, the FN3 domains of the invention can be used to noninvasively and quantitatively monitor the presence and abundance of CD8+ T cells.

In some embodiments, the present invention comprises isolated FN3 domains, wherein the FN3 domains bind to a human CD8A comprising SEQ ID NO: 35. In other embodiments, the CD8A-specific FN3 domains bind to human CD8A and cynomolgus monkey CD8A. In yet other embodiments, the CD8A-specific FN3 domains are based on Tencon sequence of SEQ ID NO: 1. In further embodiments, the CD8A-specific FN3 domains are based on the Tencon27 sequence of SEQ ID NO: 4. In some embodiments, the albumin-specific FN3 domains are isolated from the library comprising the sequence of SEQ ID NOs: 2, 3, 5, 6, 7 or 8. In some embodiments, the CD8A-specific FN3 domains do not activate CD8+ T-cells in vitro as measured by the enzyme-linked immunospot (ELISPOT) assay. In some embodiments, the CD8A-specific FN3 domains bind human CD8A with an affinity ($K_D$) of between about 0.02 to about 6.6 nM as measured by surface plasmon resonance. In other embodiments, the CD8A-specific FN3 domains have a cysteine substitution at residue position 54 of SEQ ID NOs 79, 81, 83, 89, 122 and 68. In other embodiments, the CD8A-specific FN3 domains comprise the amino acid sequence of SEQ ID NOs: 40-269. In other embodiments, the CD8A-specific FN3 domains are conjugated to a detectable label.

In addition to the described CD8A-specific FN3 domains, also provided are polynucleotide sequences capable of encoding the described FN3 domains. Vectors comprising the described polynucleotides are also provided, as are cells expressing the CD8A-specific FN3 domains herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). A process for the production of the described FN3 domains is also provided.

The present invention also comprises methods of conjugating or otherwise associating the described CD8A-specific FN3 domains to various molecules for diagnostic purposes. For example, Zr-89 or I-124 are ideal fusion partners for creation of diagnostic agents capable of detecting the presence of CD8+ T-cells. As such, the CD8A-specific FN3 domains have utility in cancer diagnostics using CD8A as a biomarker.

Another embodiment of the invention is a method of detecting CD8A-expressing cells in a biological sample comprising treating the biological sample with a diagnostic agent comprising the described CD8A-specific FN3 domains. These methods are provided in the EXAMPLES.

Within the scope of the invention are kits including the disclosed CD8A-specific FN3 domains. The kits may be used to carry out the methods of using the CD8A-specific FN3 domains provided herein, or other methods known to those skilled in the art. In some embodiments, the described kits may include the FN3 domains described herein and reagents for use in detecting the presence of human CD8A in a biological sample. The described kits may include one or more of the FN3 domains described herein and a vessel for containing the FN3 domains when not in use, instructions for use of the FN3 domains affixed to a solid support, and/or detectably labeled forms of the FN3 domains, as described herein.

BRIEF DESCRIPTION OF DRAWINGS

FIG. 11A includes kidneys, liver and spleen, while FIG. 11B is focused on the spleen. The 24 h time point for [124I]-IPEM CD8S365 is missing due to a technical issue. The high uptake of Zr-89 in kidneys due to residualization of the isotope is largely absent from the I-124 data.

DETAILED DESCRIPTION OF ILLUSTRATIVE EMBODIMENTS

Definitions

Figure 1A:
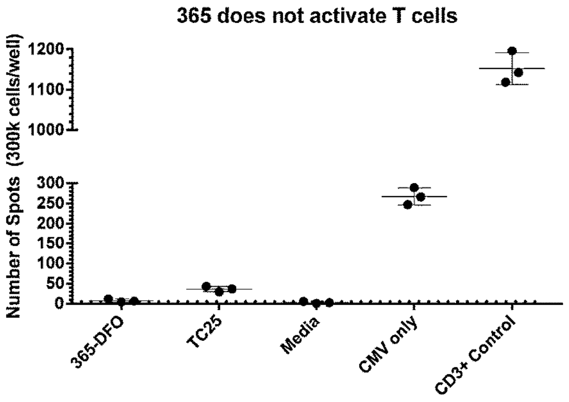
FIG. 1A-1D. The CD8S365-DFO conjugate does not activate T cells de novo and does not modulate the antigen dependent activation of T cells in a 24-hour $INF^{\gamma}$ EliSpot assay. CMV reactive T cells were treated with 365-DFO in the absence (A) or presence (B) of CMV peptides. A second M1 reactive donor was also tested in the absence (C) or presence (D) of M1 peptides.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" FN3 domain, as used herein, is intended to refer to an FN3 domain which is substantially free of other FN3 domains having different antigenic specificities (for instance, an isolated FN3 domain that specifically binds to human serum albumin is substantially free of FN3 domains that specifically bind antigens other than human serum albumin). An isolated FN3 domain that specifically binds to an epitope, isoform or variant of human serum albumin may, however, have cross-reactivity to other related antigens, for instance from other species (such as serum albumin species homologs).

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the 3rd FN3 domain of tenascin (TN3), or the 10th FN3 domain of fibronectin (FN10).

"Centyrin" as used herein refers to a FN3 domain that is based on the consensus sequence of the 15 different FN3 domains present in human tenascin C.

The term "capture agent" refers to substances that bind to a particular type of cells and enable the isolation of that cell from other cells. Examples of capture agents include but are not limited to magnetic beads, ferrofluids, encapsulating reagents and the like.

The term "biological sample" refers to blood, tissue, marrow, sputum and the like.

The term "diagnostic reagent" refers to any substance that may be used to analyze a biological sample, whether or not such substance is distributed as a single substance or in a combination with other substances in a diagnostic kit.

The term "substituting" or "substituted" or 'mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a predetermined antigen with a dissociation constant ($K_D$) of about $1\times10^{-6}$ M or less, for example about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Typically the FN3 domain of the invention binds to a predetermined antigen (i.e. human CD8A) with a $K_D$ that is at least ten fold less than its $K_D$ for a nonspecific antigen (for example BSA or casein) as measured by surface plasmon resonance using for example a Proteon Instrument (BioRad). The isolated FN3 domain of the invention that specifically binds to human CD8A may, however, have cross-reactivity to other related antigens, for example to the same predetermined antigen from other species (orthologs), such as *Macaca fascicularis* (cynomolgous monkey, cyno) or *Pan troglodytes* (chimpanzee).

The term "library" refers to a collection of variants. The library may be composed of polypeptide or polynucleotide variants.

As used herein, the terms "CD8A" or "CD8" specifically include the human CD8 alpha protein, for example, as described in NCBI Reference Sequence: NP_001139345.1, NP_0011759.3, and NP_741969.1. CD8A is also known in the scientific literature as CD8a molecule, MAL, p32, Leu2, T-cell surface glycoprotein CD8 alpha chain, CD8 antigen, alpha polypeptide (p32), Leu2 T-lymphocyte antigen, OKT8 T-cell antigen, T-cell antigen Leu2, T-lymphocyte differentiation antigen T8/Leu-2, and T8 T-cell antigen.

"Tencon" as used herein refers to the synthetic fibronectin type III (FN3) domain having the sequence shown in SEQ ID NO: 1 and described in U.S. Pat. Publ.No. US2010/0216708.

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than about 50 amino acids may be referred to as "peptides".

The term "in combination with" as used herein means that two or more therapeutics can be administered to a subject together in a mixture, concurrently as single agents or sequentially as single agents in any order.

Compositions of Matter

The present invention provides human CD8A binding FN3 domains and CD8A binding FN3 domains conjugated to detectable labels. The present invention provides polynucleotides encoding the FN3 domains of the invention or complementary nucleic acids thereof, vectors, host cells, and methods of making and using them.

CD8A Binding Molecules

The present invention provides fibronectin type III (FN3) domains that bind specifically to CD8A, optionally conjugated to a detectable label. These molecules may be widely used in preclinical applications and in cancer diagnostics using CD8A as a biomarker. The present invention provides polynucleotides encoding the FN3 domains of the invention or complementary nucleic acids thereof, vectors, host cells, and methods of making and using them.

The FN3 domains of the invention bind CD8A with high affinity and can localize CD8-expressing cells, thereby providing an efficient way to deliver diagnostic reagents into tumor microenvironment.

One embodiment of the invention an isolated FN3 domain that specifically binds a human CD8A comprising the amino acid sequence of SEQ ID NO: 35.

In some embodiment of the invention described herein, the FN3 domain of the invention cross-reacts with cynomolgus monkey CD8A having the amino acid sequence of SEQ ID NO: 271.

The FN3 domain of the invention may bind human, *Macaca fascicularis* and/or *Pan troglodytes* CD8A with a dissociation constant ($K_D$) of less than about $1\times10^{-7}$ M, for example less than about $1\times10^{-8}$ M, less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$), $K_{on}$, $K_{off}$) are made with standardized solutions of protein scaffold and antigen, and a standardized buffer, such as the buffer described herein.

In some embodiments, the CD8A binding FN3 domains comprise an initiator methionine (Met) linked to the N-terminus of the molecule.

In some embodiments, the CD8A binding FN3 domains comprise a cysteine (Cys) linked to the FN3 domain.

The addition of the N-terminal Met and/or the Cys may facilitate expression and/or conjugation of second molecules.

Another embodiment of the invention is an isolated FN3 domain that specifically binds human CD8A and wherein the CD8A-specific FN3 domain does not activate CD8+ T-cells in vitro. CD8+ T cell activation may be measured using standard methods. For example, the enzyme-linked immunospot (ELISPOT) assay may be used. The ELISPOT assay employs the sandwich enzyme-linked immunosorbent assay (ELISA) technique. The interferon-gamma antibody is precoated onto a PVDF (polyvinylidene difluoride)-backed microplate. Appropriately stimulated cells (cells+peptides, FN3 domains, etc) are pipetted into the wells and the microplate is placed into a humidified 37° C. $CO_2$ incubator for a specified period of time. During this incubation period, the immobilized interferon-gamma antibody, in the immediate vicinity of the secreting cells, binds the secreted interferon gamma. After washing away any cells and unbound substances, a second biotinylated interferon-gamma antibody is added to the wells. Following a wash to remove any unbound biotinylated antibody, alkaline-phosphatase conjugated to streptavidin is added. Unbound enzyme is subsequently removed by washing and a substrate solution (BCIP/NBT) is added. A blue-black colored precipitate forms and appears as spots at the sites of interferon-gamma localization, with each individual spot representing an individual interferon gamma-secreting cell. The spots can be counted with an automated ELISpot reader system or manually, using a stereomicroscope. The isolated CD8A binding FN3 domains of the invention do not activate CD8+ T-cells in vitro when tested at 1 μM concentrations as described in the EXAMPLES.

In some embodiments of the invention described herein, the isolated FN3 domain comprises the amino acid sequence of SEQ ID NOs: 40-269.

In some embodiments of the invention described herein, the CD8A-specific FN3 domain has a cysteine substitution at residue position 54 of SEQ ID NOs 79, 81, 83, 89, 122 and 68.

Substitutions resulting in introduction of cysteine into a protein sequence may be utilized to chemically conjugate small molecules such as cytotoxic agents, detectable labels, half-life extension molecules, chelators, polyethylene glycol and/or nucleic acids to the FN3 domain using standard chemistry.

In some embodiments, the FN3 domain specifically binding human CD8A competes for binding to human CD8A with the FN3 domain of SEQ ID NOs: 229-234. FN3 domains may be evaluated for ther competition with a reference molecule for binding human CD8A using well known in vitro methods. In an exemplary method, HEK cells recombinantly expressing human CD8A may be incubated with unlabeled reference molecule for 15 min at 4° C., followed by incubation with an excess of fluorescently labeled test FN3 domain for 45 min at 4° C. After washing in PBS/BSA, fluorescence may be measured by flow cytometry using standard methods. In another exemplary method, extracellular portion of human CD8A may be coated on the surface of an ELISA plate. Excess of unlabelled reference molecule may be added for about 15 minutes and subsequently biotinylated test FN3 domains may be added. After washes in PBS/Tween, binding of the test biotinylated FN3 domain may be detected using horseradish peroxidase (HRP)-conjugated streptavidine and the signal detected using standard methods. It is readily apparent that in the competition assays, reference molecule may be labelled and the test FN3 domain unlabeled. The test FN3 domain may compete with the reference molecule when the reference molecule inhibits binding of the test FN3 domain, or the test FN3 domain inhibits binding of the reference molecule by 20%, 30%, 40%, 50%, 60%, 70%, 80%, 85%, 90%, 95% or 100%.

In some embodiments, the isolated FN3 domain that specifically binds human CD8A of the invention is conjugated to a chelator that can bind to a radioactive metal and may be used as an imaging agent to evaluate tumor distribution, diagnosis for the presence of CD8-T cells inside tumors and/or efficacy of cancer treatment.

In some embodiments, the CD8A-specific FN3 domains are removed from the blood via renal and/or liver clearance.

Isolation of CD8A Binding FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind CD8A. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on the Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

A library designed based on the Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

TABLE 1

| Tencon topology | |
|---|---|
| FN3 domain | Tencon (SEQ ID NO: 1) |
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence-based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_// www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

The FN3 domains specifically binding human CD8A of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to CD8A by any method known in the art and described in the Example. Exemplary well-known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding CD8A are further characterized for their inhibition of CD8A activity, internalization, stability, and other desired characteristics.

The FN3 domains specifically binding human CD8A of the invention may be generated using any FN3 domain as a template to generate a library and screening the library for molecules specifically binding human CD8A using methods provided within. Exemplar FN3 domains that may be used are the 3rd FN3 domain of tenascin C (TN3) (SEQ ID NO: 145), Fibcon (SEQ ID NO: 146), and the $10^{th}$ FN3 domain of fibronectin (FN10) (SEQ ID NO: 147). Standard cloning and expression techniques are used to clone the libraries into a vector or synthesize double stranded cDNA cassettes of the library, to express, or to translate the libraries in vitro. For example, ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172, 197; 5,223,409; 6,582,915; 6,472, 147).

In some embodiments of the invention described herein, the FN3 domain specifically binding human CD8A is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

The FN3 domains specifically binding human CD8A of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (C) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domains specifically binding human CD8A of the invention may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domains of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 148), $(GGGS)_2$ (SEQ ID NO: 149), $(GGGGS)_5$ (SEQ ID NO: 150), $(AP)_2$ (SEQ ID NO: 151), $(AP)_5$ (SEQ ID NO: 152), $(AP)_{10}$ (SEQ ID NO: 153), $(AP)_{20}$ (SEQ ID NO: 154) and $A(EAAAK)_5AAA$ (SEQ ID NO: 142). The dimers and multimers may be linked to each other in a N-to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Diagnostic Agents

According to the invention, a CD8A-specific FN3 domain of the invention may comprise a detectable label. In an embodiment, the detectable label may be complexed with a chelating agent that is conjugated to the FN3 domain. In another embodiment, the detectable label may be complexed with a chelating agent that is conjugated to a linker that is conjugated to the FN3 domain. In still another embodiment, the detectable label may be coupled to a linker that is conjugated to the FN3 domain. In still yet another embodiment, a detectable label may be indirectly attached to a peptide of the invention by the ability of the label to be specifically bound by a second molecule. One example of this type of an indirectly attached label is a biotin label that can be specifically bound by the second molecule, streptavidin. Single, dual or multiple labeling may be advantageous. As used herein, a "detectable label" is any type of label which, when attached to an FN3 domain of the invention renders the FN3 domain detectable. A detectable label may also be toxic to cells or cytotoxic. In general, detectable labels may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. In a specific embodiment, the detectable label is a radionuclide. The skilled artisan would readily recognize other useful labels that are not mentioned above, which may be employed in the operation of the present invention.

A detectable label emits a signal that can be detected by a signal transducing machine. In some cases, the detectable label can emit a signal spontaneously, such as when the detectable label is a radionuclide. In other cases, the detectable label emits a signal as a result of being stimulated by an external field such as when the detectable label is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) machines. As such, the detectable label comprises a label that can be detected using magnetic resonance imaging, scintigraphic imaging, ultrasound, or fluorescence.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. An FN3 domain of the invention can be labeled for fluorescence detection by labeling the agent with a fluorophore using techniques well known in the art (see, e.g., Lohse et al., Bioconj Chem 8:503-509 (1997)). For example, many known dyes are capable of being coupled to $NH_2$-ternninal amino acid residues. Alternatively, a fluorochrome such as fluorescein may be bound to a lysine residue of the peptide linker.

A radionuclide may be a γ-emitting radionuclide, Auger-emitting radionuclide, β-emitting radionuclide, an alpha-emitting radionuclide, or a positron-emitting radionuclide. A radionuclide may be a detectable label and/or a cytotoxic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97, 103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121 m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived there from. In a specific embodiment, a radionuclide is selected from the group consisting of copper-64, zirconium-89, yttrium-90, indium-111, and lutetium-177. In another specific embodiment, a radionuclide is selected from the group consisting of yttrium-90, indium-111, and lutetium-177. In an exemplary embodiment, a radionuclide is zirconium-89.

A variety of metal atoms may be used as a detectable label. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e., iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms may be metal ions in the form of +1, +2, or +3 oxidation states. For instance, non-limiting examples include $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni_{2+}$, $Ni^{3+}$, $Ag^{+}$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

According to the invention, an FN3 domain comprising a chelating agent may incorporate a radionuclide or metal atom. Incorporation of the radionuclide or metal atom with an FN3domain-chelating agent complex may be achieved by various methods common in the art of coordination chemistry.

Half-Life Extending Moieties

The FN3 domain specifically binding human CD8A of the invention may incorporate other subunits for example via covalent interaction. In one aspect of the invention, the FN3 domain of the invention further comprises a half-life extending moiety. Exemplary half-life extending moieties are albumin, albumin variants, albumin-binding proteins and/or domains, transferrin and fragments and analogues thereof, and Fc regions.

Additional moieties may be incorporated into the FN3 domain of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the FN3 domain of the invention by incorporating a cysteine residue to the C-terminus of the molecule, or engineering cysteines into residue positions that face away from the human CD8A binding face of the molecule, and attaching a pegyl group to the cysteine using well known methods. FN3 domain of the invention incorporating additional moieties may be compared for functionality by several well known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention provides for nucleic acids encoding the FN3 domains specifically binding human CD8A of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains of the invention are also within the scope of the invention.

One embodiment of the invention is an isolated polynucleotide encoding the FN3 domain specifically binding human CD8A comprising the amino acid sequence of SEQ ID NOs: 40-269.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising the vector of the invention. The FN3 domain specifically binding human CD8A of the invention may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, NY (1989); Harlow and Lane, Antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

Another embodiment of the invention is a method of producing the isolated FN3 domain specifically binding human CD8A of the invention, comprising culturing the isolated host cell of the invention under conditions such that the isolated FN3 domain specifically binding human CD8A is expressed, and purifying the FN3 domain.

The FN3 domain specifically binding human CD8A may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Kits for Detecting Human CD8A

Provided herein are kits for detecting CD8A in a biological sample. These kits include one or more of the CD8A-specific FN3 domains described herein and instructions for use of the kit.

The provided CD8A-specific FN3 domain may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of CD8A can further include, for example, buffers or other reagents for use in an assay for determining the level of CD8A. The instructions can be, for example, printed instructions for performing the assay and/or instructions for evaluating the level of CD8A.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

Uses of Human CD8A Binding FN3 Domains of the Invention

The FN3 domains specifically binding human CD8A of the invention may be used to diagnose human disease or specific pathologies in cells, tissues, organs, fluid, or, generally, a host, using CD8A as a biomarker. The methods of the invention may be used in an animal patient belonging to any classification. Examples of such animals include mammals such as humans, rodents, dogs, cats and farm animals.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1. Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

```
Tencon: (SEQ ID NO: 1):
LPAPKNLVVSEVTEDSLRLSWTAPDAAFDSFLIQYQESEKVGEAINLTV

PGSERSYDLTGLKPGTEYTVSIYGVKGGHRSNPLSAEFTT
```

Various libraries were generated using the tencon scaffold and various design strategies. In general, libraries TCL1 and TCL2 produced good binders. Generation of TCL1 and TCL2 libraries are described in detail in Int. Pat. Publ. No. WO2014081944A2.

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a double-stranded DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO: 32). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

TCL1 library (SEQ ID NO: 2)
LPAPKNLVVSEVTEDSLRLSWTAPDAAFDSFLIQYQESEKVGEAINLTV

PGSERSYDLTGLKPGTEYTVSIYGVX$_{7-12}$PLSAEFTT;

wherein $X_1$, $X_2$, $X_3$, $X_4$, $X_5$, $X_6$, $X_7$ is any amino acid; and $X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 2 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 1 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library (SEQ ID NO: 3)

LPAPKNLVVSEVTEDSLRLSWX$_1$X$_2$X$_3$X$_4$X$_5$X$_6$X$_7$X$_8$SFLIQYQESEKVGEAINLTVPGSERSYDLTGLKPGTEYTVSIYGVX$_9$X$_{10}$X$_{11}$X$_{12}$X$_{13}$SX$_{14}$X$_{15}$LSAEFTT; wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

TABLE 1

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

```
Stabilized Tencon (Tencon27)
                                        (SEQ ID NO: 4)
LPAPKNLVVSRVTEDSARLSWTAPDAAFDSFLIQYQESEKVGEAIVLTVP

GSERSYDLTGLKPGTEYTVSIYGVKGGHRSNPLSAIFTT
```

TCL7 (Randomized FG and BC loops)
(SEQ ID NO: 5)
LPAPKNLVVSRVTEDSARLSW$X_1X_2X_3X_4X_5X_6X_7X_8X_9$FDSFLIQYQES

EKVGEAIVLTVPGSERSYDLTGLKPGTEYTVSIYGV$X_{10}X_{11}X_{12}X_{13}$ $X_{14}X_{15}X_{16}X_{17}X_{18}X_{19}$SNPLSAIFTT;

wherein $X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ is A, D, E, F, G, H, I, K, L, N, P, Q, R, S, T, V, W or Y; and $X_7$, $X_8$, $X_9$, $X_{17}$, $X_{18}$ and $X_{19}$, is A, D, E, F, G, H, I, K, L, N, P, Q, R, S, T, V, W, Y or deleted.

TCL9 (Randomized FG loop)
(SEQ ID NO: 6)
LPAPKNLVVSRVTEDSARLSWTAPDAAFDSFLIQYQESEKVGEAIVLTVP

GSERSYDLTGLKPGTEYTVSIYGV$X_1X_2X_3X_4X_5X_6X_7X_8X_9X_{10}X_{11}$ $X_{12}$SNPLSAIFTT;

$X_1$, $X_2$, $X_3$, $X_4$, $X_5$, $X_6$ and $X_7$, is A, D, E, F, G, H, I, K, L, N, P, Q, R, S, T, V, W or Y; and $X_8$, $X_9$, $X_{10}$, $X_{11}$ and $X_{12}$ is A, D, E, F, G, H, I, K, L, N, P, Q, R, S, T, V, W, Y or deleted.

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 μg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen spin column. The yield for each sub-library of TCL9 ranged from 32-34 μg.

Construction of FG BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID No. 13-16) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide endoding for amino acid A17 (130mer-L17A, SEQ ID No. 17) was produced by PCR using oligos POP2222ext (SEQ ID No. 18) and LS1114 (SEQ ID No. 19). This was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID No. 20) and LS1117 (SEQ ID No. 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7 (SEQ ID No. 31), FG8 (SEQ ID No. 30), FG9 (SEQ ID No. 29), FG10 (SEQ ID No. 28), FG11 (SEQ ID No. 27), and FG12 (SEQ ID No. 26) as templates with oligonucleotides SDG10 (SEQ ID No. 22) and SDG24 (SEQ ID No. 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID No. 24) and SDG28 (SEQ ID No. 25). 7.5 μg of each reaction product were then digested with Not1 and cleaned up with a Qiagen PCR purification column. 5.2 μg of this DNA, was ligated to an equal molar amount of RepA DNA fragment (~14 μg) digested with PspOMI and the product amplified by PCR using oligos POP2222.

Example 2: Generation of Tencon Libraries Having Alternative Binding Surfaces The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4). A full description of the methods used to construct this library is described in US. Pat. Publ. No. 2013/0226834.

TCL14 library (SEQ ID NO: 7):
LPAPKNLVVSRVTEDSARLSWTAPDAAFDSF$X_1$I$X_2$Y$X_3$E$X_4$$X_5$$X_6$$X_7$GE

AIVLTVPGSERSYDLTGLKPGTEY$X_8$V$X_9$I$X_{10}$GVKGG$X_{11}$$X_{12}$S$X_{13}$PL

SAIFTT;

Wherein $X_1$, $X_2$, $X_3$, $X_4$, $X_5$, $X_6$, $X_{10}$, $X_{11}$, $X_{12}$ and $X_{13}$ are A, D, E, F, G, H, I, K, L, N, P, Q, R, S, T, V, W, Y, or M.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 2). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 200) as described in Table 2. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and 186 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 2.

TCL24 Library
(SEQ ID NO: 8)
LPAPKNLVVSRVTEDSARLSWTAPDAAFDSF$X_1$I$X_2$Y$X_3$E$X_4$$X_5$$X_6$$X_7$GE

AI$X_8$L$X_9$VPGSERSYDLTGLKPGTEY$X_{10}$V$X_{11}$I$X_{12}$GVKGG$X_{13}$$X_{14}$S $X_{15}$PL$X_{16}$A$X_{17}$FTT;

wherein $X_1$, $X_2$, $X_3$, $X_4$, $X_5$, $X_6$, $X_{10}$, $X_{11}$, $X_{12}$ and $X_{13}$ are A, D, E, F, G, H, I, K, L, N, P, Q, R, S, T, V or W.

TABLE 2

Amino acid frequency (%) at each randomized position for TCL21, TCL23, and TCL24.

| Amino Acid | TCL19 | TCL21 | TCL23 | TCL24 |
|---|---|---|---|---|
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |

TABLE 2-continued

| Amino acid frequency (%) at each randomized position for TCL21, TCL23, and TCL24. | | | | |
|---|---|---|---|---|
| Amino Acid | TCL19 | TCL21 | TCL23 | TCL24 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc Natl Acad Sci USA 101: 2806-2810, 2004) as described above for the loop libraries.

Example 3: Selection of Fibronectin Type III (FN3) Domains that Bind Cd8a

Design and Production of Human CD8 Alpha Antigens:

Two human CD8 alpha (Swiss Prot P01732) constructs were expressed and purified from HEK cells to produce recombinant protein for CIS-Display panning (Table 3).

TABLE 3

| CD8A constructs generated for use as antigens | | |
|---|---|---|
| Construct | SEQID No. | Description |
| CD8W7 | 35 | Human CD8 alpha residues 22-167 fused to Fc fragment of human IgG1 |
| CD8W13 | 36 | Human CD8 alpha residues 22-182 fused to Fc fragment of human IgG1 |

Each construct was designed to include a murine IgG Kappa secretion signal (SEQ ID No 3) and was fused to the Fc fragment of human IgG1 (SEQID No. 4). The CD8 alpha and Fc fragment sequences were connected by a linker containing a flag and polyhistidine tag sequence (SEQ ID No 5.)

Plasmids encoding these proteins were transfected into HEK 293-Expi cells by transient transfection and culture supernatants were harvested by centrifugation at 6000×g and clarified with a 0.2 micron filter. Supernatants were loaded onto a HiTrap Mabsure Select column (GE Healthcare) and CD8A proteins eluted in 0.1 M Na-Acetate pH 3.5 and neutralized by addition of 2M Tris pH 7. Each sample was then dialyzed into PBS pH 7.4 for biotinylation with a No Weigh EZ-Link-Sulfo-NHS-LC-Biotin biotinylation kit (Thermo Scientific).

Library Screening

Cis-display was used to select human CD8 alpha-binding domains from the TCL18, TCL19, TCL21, TCL23, and TCL24 libraries. Biotinylated CD8W7 and CD8W13 were used for panning. For in vitro transcription and translation (ITT), 3 μg of library DNA were incubated with 0.1 mM complete amino acids, 1× S30 premix components, and 15 μL of S30 extract (Promega) in a total volume of 50 μL and incubated at 30° C. After 1 hour, 375 μL of blocking solution ((0.1% Casein (Thermo Fisher, Rockford, IL), 100 mg/ml Herring Sperm DNA (Promega, Madison, WI), 1 mg/mL heparin (Sigma-Aldrich, St. Louis, MO)) was added and the reaction was incubated on ice for 15 minutes. For selection, biotinylated antigen was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, IL) (Rounds 1, 3, and 5) or streptavidin magnetic beads (Promega, Madison, WI) (Rounds 2 and 4) and unbound library members were removed by washing the beads 5-14 times with 500 μL PBST followed by 2 washes with 500 μL PBS. Additional selection rounds were performed in order to identify scaffold molecules with improved affinities. Briefly, outputs from round 5 were prepared as described above and subjected to additional iterative rounds of selection with the following changes: the biotinylated target concentration decreased to 25 nM (Rounds 6 and 7) or 2.5 nM (Rounds 8 and 9), and an additional 1 hour wash was performed in the presence of an excess of non-biotinylated target protein. The goal of these changes was to simultaneously select for binders with a potentially faster on-rate and a slower off-rate yielding a substantially lower $K_D$).

Following panning, selected FN3 domains were amplified by PCR using oligos Tcon6 (SEQID NO: 33) and Tcon5shortE86I (SEQID NO: 34), subcloned by annealing into a pET15-LIC and transformed into BL21-GOLD (DE3) cells (Agilent, Santa Clara,CA) for soluble expression in *E. coli* using standard molecular biology techniques. Single clones were picked and grown to saturation in 1 mL LB with ampicillin in 96 deepwell plates at 37° C. The following day, 25 μL was transferred to fresh 1 mL LB-Amp media in 96 deepwell plates and grown at 37° C. for 2 hours. IPTG was added at 1 mM final concentration and protein expression was induced at 30° C. for 16 hours. The cells were harvested by centrifugation and subsequently lysed with Bugbuster HT (EMD Chemicals, Gibbstown, NJ) supplemented with 0.2 mg/ml final Chicken Egg White Lysozyme (Sigma-Aldrich, St. Louis, MO). Cells were harvested approximately 16 hours later by centrifugation and frozen at −20° C. Cell lysis was achieved by incubating each pellet in 0.6 mL of BugBuster® HT lysis buffer (Novagen EMD Biosciences) with shaking at room temperature for 45 minutes.

Selection of FN3 Domains that Bind CD8A

Neutravidin-coated plates were blocked for 1 hour in Starting Block T20 (Pierce) and then coated with biotinylated CD8W7 or CD8W13 (same antigen as in panning) or negative control (human Fc) for 1 hour. Plates were rinsed with TBST and diluted lysate was applied to plates for 1 hour. Following additional rinses, wells were treated with HRP-conjugated anti-FN3 domain antibody (PAB25) for 1 h and then assayed with POD (Roche). FN3 domain molecules with signals at least 10-fold above background were selected for further analysis.

Small Scale Expression and Purification of Identified FN3 Domains Binding CD8A

Isolated clones from unique hits identified by biochemical binding ELISA were combined into a single hit plate for growth in 96-well block plates; clones grew in 1 mL cultures (LB media supplemented with kanamycin for selection) at 37° C. overnight with shaking. For protein expression in 96-block plates, 1 mL TB media supplemented with kanamycin was inoculated with 50 μL of the overnight culture and grown at 37° C. with continual shaking at 300 rpm until $OD_{600}$=0.6-1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Pellets were lysed with BugBuster® HT lysis buffer (Novagen EMD Biosciences) and His-tagged Centyrins purified from the clarified lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of anti-CD8 alpha FN3 domain molecules. Aliquots (10 μL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Wild-type Tencon was included in each run as a control. Agilent ChemStation software was used to analyse the elution profiles. Only those proteins with elution profiles similar to that of the tenascin consensus protein in the same run were considered for further characterization. After panning, ELISA screening and size exclusion chromatographic analysis, a total of 190 unique anti-human CD8 alpha FN3 domains were isolated that bound to recombinant human CD8 alpha greater than 10-fold over background and were free of aggregates by SEC (Table 4, SEQID no. 40-228, and 70).

TABLE 4

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P282AR9P1356_A10 | 40 | 4258 | 2093 | 2.91E−04 | 10584 | 3122 |
| P282AR9P1356_A4 | 41 | 16674 | 4380 | 8.61E−05 | 26447 | 8632 |
| P282AR9P1356_A6 | 42 | 10835 | 3441 | 9.73E−05 | 31432 | 5783 |
| P282AR9P1356_B9 | 43 | 17158 | 3670 | 2.95E−04 | 36397 | 5437 |
| P282AR9P1356_D3 | 44 | 5963 | 2403 | 1.58E−04 | 13852 | 3365 |
| P282AR9P1356_H1 | 45 | 14696 | 3234 | 1.14E−04 | 46317 | 5699 |
| P282AR9P1356_H6 | 46 | 6646 | 2642 | 8.08E−05 | 14393 | 3205 |
| P282BR9P1357_A9 | 47 | 3117 | 1074 | 5.90E−04 | 7281 | 1940 |
| P282BR9P1357_B2 | 48 | 5931 | 2875 | 1.00E−04 | 17974 | 3841 |
| P282BR9P1357_C10 | 49 | 9779 | 2901 | 4.58E−04 | 24476 | 5110 |
| P282BR9P1357_C4 | 50 | 16809 | 4224 | 1.27E−04 | 41586 | 7064 |
| P282BR9P1357_D12 | 51 | 15269 | 3899 | 8.76E−05 | 40450 | 7364 |
| P282BR9P1357_D2 | 52 | 9606 | 1568 | 1.05E−03 | 25843 | 2525 |
| P282BR9P1357_E5 | 53 | 6726 | 2587 | 2.10E−04 | 10563 | 4101 |
| P282BR9P1357_G9 | 54 | 12733 | 2803 | 3.04E−04 | 41492 | 4635 |
| P282BR9P1357_H3 | 55 | 11142 | 3033 | 2.85E−04 | 27090 | 5701 |
| P282CR9P1358_C2 | 56 | 10086 | 1059 | 1.13E−03 | 55786 | 7047 |
| P282CR9P1358_C5 | 57 | 2706 | 511 | 9.99E−04 | 25688 | 1831 |
| P282CR9P1358_D10 | 58 | 28650 | 2764 | 3.11E−04 | 74051 | 4072 |
| P282CR9P1358_F11 | 59 | 6420 | 749 | 1.35E−03 | 62412 | 6585 |
| P282CR9P1358_F5 | 60 | 24427 | 3072 | 6.37E−04 | 85691 | 13667 |
| P282DR9P1359_A12 | 61 | 32222 | 5952 | 8.12E−05 | 88032 | 15491 |
| P282DR9P1359_A7 | 62 | 38382 | 8764 | 7.54E−04 | 83943 | 22803 |
| P282DR9P1359_A8 | 63 | 21124 | 2113 | 6.38E−04 | 70263 | 7766 |
| P282DR9P1359_B2 | 64 | 22228 | 2726 | 6.38E−04 | 60866 | 4472 |
| P282DR9P1359_C10 | 65 | 27822 | 2879 | 9.91E−04 | 98481 | 15134 |
| P282DR9P1359_C11 | 66 | 18176 | 1288 | 2.16E−03 | 19916 | 457 |
| P282DR9P1359_C12 | 67 | 15106 | 944 | 9.78E−04 | 66538 | 3636 |
| P282DR9P1359_C5 | 68 | 31017 | 5551 | 1.74E−04 | 95679 | 14183 |
| P282DR9P1359_D12 | 69 | 4540 | 542 | 1.93E−03 | 37139 | 1746 |
| P282DR9P1359_E11 | 70 | 40607 | 7578 | 2.65E−04 | 104291 | 33144 |
| P282DR9P1359_E2 | 71 | 28491 | 4824 | 2.06E−03 | 77725 | 10939 |
| P282DR9P1359_E3 | 72 | 4307 | 349 | 2.63E−03 | 52426 | 1625 |
| P282DR9P1359_E5 | 73 | 24100 | 1954 | 1.01E−03 | 81183 | 13601 |
| P282DR9P1359_E6 | 74 | 20507 | 1262 | 1.71E−03 | 61734 | 5065 |
| P282DR9P1359_E8 | 75 | 26074 | 2919 | 1.19E−03 | 80973 | 16948 |
| P282DR9P1359_F11 | 76 | 35639 | 6592 | 5.54E−04 | 86740 | 16146 |
| P282DR9P1359_F2 | 77 | 18415 | 3047 | 7.22E−04 | 38228 | 4031 |
| P282DR9P1359_F3 | 78 | 6343 | 646 | 1.06E−03 | 48861 | 3084 |
| P282DR9P1359_F5 | 79 | 48931 | 8483 | 9.02E−05 | 113733 | 34709 |
| P282DR9P1359_F6 | 80 | 19937 | 3782 | 3.89E−04 | 73219 | 10680 |
| P282DR9P1359_F7 | 81 | 38323 | 6932 | 3.65E−04 | 96456 | 26331 |
| P282DR9P1359_G4 | 82 | 26568 | 2670 | 5.17E−04 | 78619 | 6006 |
| P282DR9P1359_G7 | 83 | 37626 | 6129 | 1.14E−04 | 69085 | 8769 |
| P282DR9P1359_H5 | 84 | 919 | 278 | 4.49E−03 | 2252 | 500 |
| P282ER9P1360_A9 | 85 | 23379 | 5344 | 1.33E−04 | 64694 | 8732 |
| P282ER9P1360_C1 | 86 | 25874 | 6291 | 1.81E−04 | 64813 | 9679 |
| P282ER9P1360_C4 | 87 | 19202 | 3459 | 1.07E−03 | 33427 | 3896 |
| P282ER9P1360_C6 | 88 | 25942 | 5079 | 1.75E−04 | 52783 | 7579 |

TABLE 4-continued

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P282ER9P1360_C8 | 89 | 30578 | 6013 | 1.56E−04 | 66829 | 10220 |
| P282ER9P1360_D11 | 90 | 36755 | 3210 | 1.42E−04 | 76564 | 1937 |
| P282ER9P1360_E4 | 91 | 26889 | 5030 | 1.91E−04 | 60757 | 6867 |
| P282ER9P1360_F11 | 92 | 22442 | 3863 | 2.25E−04 | 48653 | 4407 |
| P282ER9P1360_G10 | 93 | 26951 | 7046 | 2.07E−03 | 62701 | 22641 |
| P282ER9P1360_G7 | 94 | 25438 | 5869 | 2.21E−04 | 69709 | 9921 |
| P282ER9P1360_H10 | 95 | 2513 | 506 | 1.04E−03 | 27063 | 1887 |
| P282ER9P1360_H2 | 96 | 15165 | 3479 | 2.69E−04 | 44563 | 4535 |
| P282ER9P1360_H3 | 97 | 19992 | 4271 | 2.42E−04 | 65994 | 6441 |
| P282FR9P1361_A3 | 98 | 7670 | 1661 | 7.57E−04 | 8476 | 740 |
| P282FR9P1361_A5 | 99 | 32752 | 5213 | 1.92E−04 | 63541 | 8108 |
| P282FR9P1361_C7 | 100 | 8538 | 1575 | 2.24E−03 | 11639 | 896 |
| P282FR9P1361_D3 | 101 | 6881 | 1028 | 5.02E−03 | 14762 | 764 |
| P282FR9P1361_E12 | 102 | 15794 | 1130 | 1.09E−03 | 63536 | 15052 |
| P282FR9P1361_F1 | 103 | 5498 | 801 | 1.26E−03 | 9869 | 1392 |
| P282FR9P1361_F11 | 104 | 2189 | 382 | 2.13E−03 | 2289 | 384 |
| P282FR9P1361_F2 | 105 | 4610 | 498 | 4.96E−03 | 10883 | 462 |
| P282FR9P1361_F3 | 106 | 5157 | 674 | 1.07E−02 | 9709 | 513 |
| P282FR9P1361_F7 | 107 | 7001 | 1107 | 1.14E−03 | 1705 | 353 |
| P282FR9P1361_G9 | 108 | 859 | 297 | 6.53E−03 | 3746 | 666 |
| P282FR9P1361_H4 | 109 | 13056 | 3736 | 3.17E−04 | 26273 | 2504 |
| P282FR9P1361_H5 | 110 | 5730 | 698 | 5.77E−03 | 11794 | 637 |
| P283AR9P1362_A3 | 111 | 5535 | 1400 | 1.53E−03 | 17345 | 3533 |
| P283AR9P1362_A4 | 112 | 6314 | 2539 | 3.02E−04 | 21218 | 4402 |
| P283AR9P1362_B10 | 113 | 15380 | 3703 | 1.39E−04 | 35686 | 8380 |
| P283AR9P1362_B2 | 114 | 13649 | 3505 | 1.60E−04 | 38828 | 6479 |
| P283AR9P1362_B8 | 115 | 5737 | 1576 | 6.48E−04 | 12886 | 2271 |
| P283AR9P1362_C12 | 116 | 7064 | 2616 | 9.94E−05 | 14808 | 3832 |
| P283AR9P1362_C6 | 117 | 15955 | 4147 | 1.09E−03 | 17494 | 5690 |
| P283AR9P1362_C7 | 118 | 10957 | 2792 | 1.86E−04 | 19690 | 5515 |
| P283AR9P1362_D2 | 119 | 8650 | 2758 | 2.53E−04 | 17182 | 5333 |
| P283AR9P1362_D3 | 120 | 9498 | 3484 | 1.25E−04 | 34619 | 6052 |
| P283AR9P1362_D4 | 121 | 9832 | 2977 | 9.72E−05 | 25671 | 4101 |
| P283AR9P1362_D6 | 122 | 13686 | 3664 | 2.64E−05 | 33547 | 7721 |
| P283AR9P1362_D7 | 123 | 17327 | 3354 | 1.18E−04 | 27491 | 4849 |
| P283AR9P1362_E9 | 124 | 6178 | 2010 | 3.27E−04 | 15869 | 2837 |
| P283AR9P1362_F12 | 125 | 8970 | 2623 | 7.28E−05 | 26333 | 3794 |
| P283AR9P1362_F2 | 126 | 9619 | 1366 | 2.11E−03 | 26443 | 5518 |
| P283AR9P1362_F8 | 127 | 9195 | 3167 | 1.12E−04 | 23735 | 4571 |
| P283AR9P1362_G11 | 128 | 12690 | 3531 | 1.02E−04 | 32484 | 6826 |
| P283AR9P1362_G3 | 129 | 18512 | 4307 | 9.45E−05 | 35268 | 9198 |
| P283AR9P1362_H11 | 130 | 5734 | 2268 | 1.80E−04 | 11588 | 3655 |
| P283BR9P1363_A10 | 131 | 7886 | 2753 | 3.60E−04 | 27790 | 4105 |
| P283BR9P1363_A8 | 132 | 11285 | 2536 | 3.53E−04 | 24234 | 3453 |
| P283BR9P1363_B2 | 133 | 8358 | 2399 | 2.08E−04 | 14846 | 2819 |
| P283BR9P1363_B6 | 134 | 14534 | 3453 | 2.69E−04 | 37691 | 6839 |
| P283BR9P1363_C4 | 135 | 9073 | 2247 | 4.09E−04 | 23387 | 3266 |
| P283BR9P1363_C8 | 136 | 16541 | 3739 | 3.35E−04 | 37175 | 9082 |
| P283BR9P1363_D11 | 137 | 8692 | 2890 | 4.95E−04 | 20572 | 11630 |
| P283BR9P1363_E4 | 138 | 10790 | 2498 | 3.29E−04 | 17702 | 2469 |
| P283BR9P1363_E6 | 139 | 8239 | 2079 | 1.36E−03 | 16784 | 3715 |
| P283BR9P1363_F2 | 140 | 14473 | 3274 | 2.88E−04 | 33286 | 5278 |
| P283BR9P1363_F4 | 141 | 11933 | 2963 | 1.55E−04 | 20245 | 4479 |
| P283BR9P1363_F6 | 142 | 10632 | 3229 | 8.21E−05 | 31568 | 4571 |
| P283BR9P1363_G2 | 143 | 9640 | 3226 | 1.22E−04 | 15899 | 5383 |
| P283BR9P1363_G5 | 144 | 14798 | 3307 | 1.40E−04 | 24945 | 4430 |
| P283BR9P1363_G7 | 145 | 4639 | 2340 | 4.01E−05 | 7212 | 3022 |
| P283DR9P1364_A4 | 146 | 9491 | 1024 | 1.09E−03 | 48337 | 6653 |
| P283DR9P1364_A7 | 147 | 8985 | 435 | 1.97E−03 | 39870 | 2641 |
| P283DR9P1364_B1 | 148 | 1477 | 666 | 1.56E−03 | 8617 | 746 |
| P283DR9P1364_B11 | 149 | 4255 | 451 | 1.30E−03 | 22852 | 1590 |
| P283DR9P1364_B4 | 150 | 45452 | 6062 | 1.09E−04 | 96492 | 20238 |
| P283DR9P1364_C10 | 151 | 4936 | 649 | 1.29E−03 | 34234 | 2713 |
| P283DR9P1364_D11 | 152 | 32293 | 4223 | 5.14E−04 | 70431 | 16240 |
| P283DR9P1364_D8 | 153 | 656 | 244 | 6.61E−03 | 2484 | 365 |
| P283DR9P1364_D9 | 154 | 42285 | 5245 | 4.30E−04 | 88300 | 19979 |
| P283DR9P1364_E3 | 155 | 1285 | 317 | 2.53E−03 | 9128 | 887 |
| P283DR9P1364_E5 | 156 | 17625 | 1269 | 8.25E−04 | 55654 | 5091 |
| P283DR9P1364_E7 | 157 | 5394 | 442 | 2.43E−03 | 28732 | 2241 |
| P283DR9P1364_E8 | 158 | 14321 | 1181 | 7.56E−04 | 59328 | 5510 |
| P283DR9P1364_E9 | 159 | 4295 | 548 | 1.90E−03 | 19688 | 2096 |
| P283DR9P1364_F2 | 160 | 39164 | 6252 | 1.61E−04 | 91474 | 16946 |

TABLE 4-continued

Summary of CD8A-binding FN3 domains identified from ELISA screens

| Clone ID | SEQ ID NO: | Human T-cell Binding 2 uM (MFI) | Human T-cell Binding 0.2 uM (MFI) | kd (1/s) | Cyno T-cell Binding 2 uM (MFI) | Cyno T-cell Binding 0.2 uM (MFI) |
|---|---|---|---|---|---|---|
| P283DR9P1364_F6 | 161 | 17215 | 1831 | 1.00E-03 | 33767 | 3161 |
| P283DR9P1364_F8 | 162 | 6305 | 458 | 1.74E-03 | 36659 | 1302 |
| P283DR9P1364_G10 | 163 | 6291 | 409 | 2.53E-03 | 10920 | 769 |
| P283DR9P1364_G9 | 164 | 9892 | 401 | 7.79E-03 | 47097 | 2796 |
| P283DR9P1364_H1 | 165 | 29248 | 3033 | 6.13E-04 | 54014 | 10610 |
| P283DR9P1364_H11 | 166 | 11479 | 834 | 9.64E-04 | 60609 | 9459 |
| P283DR9P1364_H6 | 167 | 2623 | 268 | 2.30E-03 | 6002 | 418 |
| P283DR9P1364_H9 | 168 | 32763 | 4057 | 2.71E-04 | 54593 | 4556 |
| P283ER9P1365_A1 | 169 | 25512 | 3862 | 4.67E-04 | 9676 | 1365 |
| P283ER9P1365_A7 | 170 | 18513 | 1315 | 7.86E-04 | 36568 | 2960 |
| P283ER9P1365_B6 | 171 | 22998 | 3397 | 2.88E-04 | 30081 | 2692 |
| P283ER9P1365_C1 | 172 | 8004 | 644 | 1.15E-03 | 23975 | 1884 |
| P283ER9P1365_E2 | 173 | 20011 | 2867 | 3.11E-04 | 17177 | 1905 |
| P283ER9P1365_F4 | 174 | 24065 | 2596 | 2.16E-04 | 43243 | 2038 |
| P283ER9P1365_G1 | 175 | 1280 | 318 | 3.67E-03 | 489 | 383 |
| P283ER9P1365_G3 | 176 | 12481 | 2916 | 2.50E-03 | 3480 | 1470 |
| P283ER9P1365_H3 | 177 | 17965 | 953 | 3.75E-04 | 19560 | 436 |
| P283FR9P1366_A1 | 178 | 8782 | 516 | 2.26E-03 | 39384 | 1650 |
| P283FR9P1366_A5 | 179 | 27649 | 3598 | 5.85E-04 | 67839 | 10945 |
| P283FR9P1366_A9 | 180 | 1717 | 252 | 3.94E-03 | 8809 | 580 |
| P283FR9P1366_B7 | 181 | 11365 | 899 | 1.15E-03 | 51186 | 4668 |
| P283FR9P1366_C2 | 182 | 40957 | 4319 | 4.91E-04 | 89242 | 19288 |
| P283FR9P1366_C3 | 183 | 1823 | 407 | 2.07E-03 | 4628 | 1044 |
| P283FR9P1366_C4 | 184 | 33821 | 3754 | 5.36E-04 | 63373 | 10200 |
| P283FR9P1366_C6 | 185 | 4541 | 483 | 1.43E-03 | 26242 | 1675 |
| P283FR9P1366_D12 | 186 | 27793 | 1528 | 1.76E-03 | 87643 | 8143 |
| P283FR9P1366_D6 | 187 | 32924 | 4554 | 5.09E-04 | 79621 | 10399 |
| P283FR9P1366_D7 | 188 | 7517 | 566 | 3.54E-04 | 41434 | 2581 |
| P283FR9P1366_D8 | 189 | 3394 | 413 | 1.34E-03 | 28181 | 2296 |
| P283FR9P1366_E11 | 190 | 4594 | 567 | 1.41E-03 | 14194 | 1469 |
| P283FR9P1366_F5 | 191 | 6880 | 720 | 1.04E-03 | 46414 | 4695 |
| P283FR9P1366_F8 | 192 | 3970 | 369 | 4.03E-03 | 26970 | 2269 |
| P283FR9P1366_F9 | 193 | 33559 | 6295 | 4.94E-04 | 84279 | 24622 |
| P283FR9P1366_G1 | 194 | 3605 | 650 | 8.72E-04 | 39796 | 4981 |
| P283FR9P1366_G5 | 195 | 8450 | 261 | 7.05E-04 | 36380 | 369 |
| P283FR9P1366_G8 | 196 | 6857 | 574 | 1.08E-03 | 37144 | 3126 |
| P283FR9P1366_H10 | 197 | 25020 | 2414 | 6.30E-04 | 75192 | 13854 |
| P283FR9P1366_H11 | 198 | 18896 | 2331 | 1.39E-03 | 37386 | 3659 |
| P283FR9P1366_H3 | 199 | 7671 | 632 | 1.21E-03 | 40770 | 3173 |
| P283FR9P1366_H5 | 200 | 3137 | 252 | 3.18E-03 | 5091 | 477 |
| P283FR9P1366_H6 | 201 | 43937 | 7129 | 2.05E-04 | 81542 | 18993 |
| P283FR9P1366_H7 | 202 | 13778 | 567 | 1.77E-03 | 24435 | 1238 |
| P283FR9P1366_H8 | 203 | 24942 | 4544 | 1.75E-04 | 61256 | 17144 |
| P283FR9P1366_H9 | 204 | 8570 | 693 | 1.98E-03 | 36501 | 2877 |
| P283GR7P1367_A11 | 205 | 11326 | 1029 | 6.35E-04 | 66691 | 5666 |
| P283GR7P1367_B4 | 206 | 8302 | 446 | 5.18E-03 | 396 | 367 |
| P283GR7P1367_B7 | 207 | 10865 | 739 | 1.27E-03 | 37518 | 3134 |
| P283GR7P1367_B9 | 208 | 11242 | 1092 | 1.16E-03 | 2924 | 442 |
| P283GR7P1367_C9 | 209 | 10989 | 896 | 2.21E-03 | 66977 | 5553 |
| P283GR7P1367_E5 | 210 | 10014 | 1333 | 1.24E-03 | 3189 | 533 |
| P283GR7P1367_F5 | 211 | 4565 | 601 | 1.08E-03 | 28950 | 2051 |
| P283GR7P1367_G8 | 212 | 1463 | 450 | 3.85E-03 | 21031 | 1421 |
| P283GR7P1367_H2 | 213 | 1621 | 390 | 2.35E-03 | 4207 | 864 |
| P283GR7P1367_H8 | 214 | 5269 | 303 | 9.74E-03 | 20918 | 930 |
| P283GR7P1367_H9 | 215 | 1714 | 434 | 1.47E-03 | 6121 | 918 |
| P283HR7P1368_A10 | 216 | 13632 | 3233 | 5.13E-04 | 42326 | 4772 |
| P283HR7P1368_B12 | 217 | 13399 | 1538 | 4.53E-05 | 18650 | 826 |
| P283HR7P1368_C3 | 218 | 12727 | 2215 | 3.49E-04 | 13326 | 1306 |
| P283HR7P1368_D1 | 219 | 14077 | 2312 | 1.66E-03 | 7850 | 1408 |
| P283HR7P1368_D2 | 220 | 15246 | 1907 | 1.30E-03 | 11132 | 950 |
| P283HR7P1368_D4 | 221 | 28979 | 6850 | 2.35E-04 | 52999 | 23549 |
| P283HR7P1368_F10 | 222 | 18836 | 2661 | 1.65E-04 | 16121 | 1019 |
| P283HR7P1368_F6 | 223 | 14325 | 3510 | 1.80E-04 | 20580 | 3541 |
| P283HR7P1368_G1 | 224 | 31276 | 4940 | 2.15E-03 | 69817 | 11559 |
| P283HR7P1368_G10 | 225 | 8122 | 753 | 1.45E-03 | 23790 | 2660 |
| P283HR7P1368_G11 | 226 | 19305 | 2647 | 3.73E-04 | 14857 | 1343 |
| P283HR7P1368_H1 | 227 | 15389 | 2460 | 5.52E-04 | 17285 | 1974 |
| P283HR7P1368_H8 | 228 | 22758 | 1612 | 7.63E-04 | 35932 | 4888 |
| Tencon25-His | 270 | 341 | 219 | | 337 | 336 |

Screen for Binding to T-Cells from Human and Cynomolgus Monkey Donors

Binding of the 190 ELISA hits to human and cynomologous monkey primary CD8 T cells was assessed by flow cytometry. The FN3 domain molecules were diluted to 2 μM and 0.2 μM in PBS and incubated with human or cynomologous monkey CD8+ T cells in 96-well format. After 1 hour at 4° C., the cells were washed once with PBS and then resuspended with an anti-FN3 domain antibody (PAB25) solution. Following this incubation, the cells were washed twice with PBS and a PE conjugated secondary antibody and a viability dye were added. Finally, cells were washed and resuspended in PBS for flow cytometric analysis using a BD Canto Instrument. Cells were gating on live cells and median fluorescence intensity of the bound Centyrins (PE channel) was calculated using Cytobank software. Results are summarized in Table 4.

Off-Rate Analysis of Anti-Human CD8 Alpha Centyrins

Purified anti-CD8A FN3 domains were subjected to off-rate analysis using a Proteon surface plasmon resonance instrument in order to pick clones with the slowest off-rates for further characterization. Measured off-rates ranged from 2.64E-5 to 1.07E-2 $sec^{-1}$ as shown in Table 4.

Goat anti-human Fc IgG (Jackson immunoresearch, Cat #109-005-098) was directly immobilized on a GLC sensor chip at 10 μg/ml, pH5.0 via amine coupling (pH 5.0) on all 6 ligand channels in vertical orientation on the chip with a flow rate of 30 μl/min in PBST (PBS, 0.005% Tween). The immobilized GAH-Fc IgG densities averaged about 6000 Response Units (Ru) with less than 1% variation among different channels. In house human CD8A-Fc was captured in vertical orientation at 3 different ligand densities, 10, 5, 2.5 μg/ml for 5 minutes at 30 ul/minute flowrate. All FN3 domains were normalized to a 3 μM concentration, and tested for binding in horizontal orientation. All 6 analyte channels were used for FN3 domains to maximize the screening throughput. The dissociation phase was monitored for 15 minutes at a flow rate of 100 μl/min using PBST as running buffer. Regeneration of the surface was achieved by a short pulse of 0.85% phosphoric acid (18 s contact time at 100 uL/min). Data analyses were performed using Bio-Rad ProteOn Manager software (version 3.1.0.6). Raw data were double referenced by subtraction of the interspot (empty chip surface, no protein immobilized or captured) signals to correct the non-specific binding of the FN3 domain to the pre-coated GAH-Fc IgG surface, followed by a double correction using empty channel L6 where no hCD8A-Fc was captured. The processed binding data were locally fit to a 1:1 simple Langmuir binding model to extract the koff for each FN3 domain binding to captured hCD8A-Fc.

Example 4: Engineering of Anti-CD8a FN3 Domains

A number of mutations were designed into top anti-CD8A candidates in order to eliminate post translational modification risks of oxidation (methionine, or tryptophan), deamidation (NS), isomerization (DG) and clipping (DP). Proline residues found in beta strands were also mutated as proline has a potential for destabilizing beta strands (Chiba T., et al. J Biol Chem. 2003; 278:47016-24). Only residues derived from FN3 domain library-designed positions were considered for mutation. Variant sequences were chosen to either mimic similar chemical properties of the parent molecule (example tryptophan to tyrosine) or to replace the PTM risk amino acid with an amino acid found in other CD8A FN3 domains at that position. A full list of engineered sequences is found in Table 5. The dissociation rate between each mutant and recombinant CD8 alpha was measured by surface plasmon resonance to estimate relative binding strengths.

TABLE 5

Dissociation rates of CD8A Centyrin mutants. Mutants are grouped according to the parent molecule.

| Sample | $k_d$ (1/s) | Mutations | SEQ ID NO: |
|---|---|---|---|
| P282DR9P1359_C5 | 1.47E−04 | Parent | 68 |
| CD8S402 | 4.84E−05 | D40P | 266 |
| CD8S396 | 1.52E−04 | W32Y | 260 |
| CD8S398 | 4.43E−04 | W32S | 262 |
| CD8S397 | 6.60E−04 | W32Q | 261 |
| CD8S399 | 1.34E−03 | W38Y | 263 |
| CD8S401 | 1.27E−02 | W38I | 265 |
| CD8S400 | 2.26E−02 | W38L | 264 |
| CD8S404 | 3.09E−02 | P36A | 268 |
| P282DR9P1359_F5 | 5.78E−05 | Parent | 79 |
| CD8S371 | 1.94E−04 | W48Y | 235 |
| CD8S377 | 4.00E−04 | W81E | 241 |
| CD8S374 | 4.03E−04 | W81Y | 238 |
| CD8S372 | 5.71E−04 | W48L | 236 |
| CD8S375 | 8.30E−04 | W81L | 239 |
| CD8S376 | 8.46E−04 | W81S | 240 |
| CD8S373 | 4.03E−03 | W48I | 237 |
| P282DR9P1359_G7 | 1.06E−05 | | 83 |
| CD8S379 | 4.97E−05 | D43S | 243 |
| CD8S378 | 5.80E−05 | D43E | 242 |
| CD8S388 | 7.54E−05 | N81Q | 252 |
| CD8S387 | 1.25E−04 | W83E | 251 |
| CD8S381 | 2.00E−04 | W70F | 245 |
| CD8S383 | 7.47E−04 | W74Y | 247 |
| CD8S380 | 1.21E−03 | W70Y | 244 |
| CD8S382 | 2.47E−01 | W70S | 246 |
| P282ER9P1360_C8 | 1.79E−04 | Parent | 89 |
| CD8S390 | 1.52E−04 | W68Y | 254 |
| CD8S389 | 1.84E−04 | W68F | 253 |
| CD8S391 | 3.20E−04 | W68H | 255 |
| CD8S405 | 1.14E−03 | P48T | 269 |
| P282DR9P1359_F7 | 3.39E−04 | Parent | 81 |
| CD8S403 | 1.33E−04 | P36A | 267 |
| CD8S392 | 1.55E−03 | W38Y | 256 |
| CD8S395 | 1.89E−03 | W38H | 259 |
| CD8S393 | 2.55E−03 | W38L | 257 |
| CD8S394 | 3.55E−03 | W38I | 258 |

From the data presented in Table 5, it is apparent that a number of mutations that reduce developability risks maintain dissociation rates similar to that of the parent molecule. Mutants CD8S402 (elimination of DP site), CD8S390 (elimination of Trp residue), and CD8S403 (removal of Pro from beta strand) resulted in slower dissociation rates than the parent appropriate molecule, indicative of tighter binding. A number of other mutations maintain binding similar to the parent molecule and thus might be preferred over the parent as these molecules pose less CMC related risks during development.

Example 5: Affinity Measurements of CD8a-Binding FN3 Domains

Nineteen anti-CD8A candidates were selected for full kinetic analysis of binding to recombinant human CD8 alpha. These candidates were selected from the above positive hits (Table 4) using the criteria of 1) strong relative binding to human T-cells, 2) strong relative binding to cyno T-cells, 3) minimal reduction in cell binding at 0.2 uM compared to 2 uM, 4) free of aggregates via SEC, 5) off-rates slower than 2.07E-3 sec-1, 6) sequence diversity with respect to sequence families, and 7) relative propensity for sequences with potential developability challenges (oxidation, deamidation, clipping and hydrophobicity).

Affinities of the top 19 candidates, later a repeat of the top 6 candidates, binding to hCD8A-Fc were measured on a ProteOn XPR36 instrument (Bio-Rad) using GLC sensor chips under similar conditions to those for koff screening. Goat anti-human Fc antibody was directly immobilized on the chip by standard amine coupling at 10 μg/ml, pH 5.0 on all 6 ligand channels in vertical orientation on the chip with a flow rate of 30 μl/min in PBST (PBS, 0.005% Tween), achieving an average of 6200 Rus on each ligand channel. Human CD8A-Fc was then captured at five surface densities ranging from 200 to 1200 response units, leaving the 6th channel as empty channel control for GAH-Fc IgG surface. Binding was measured by flowing five different concentrations of anti-CD8A FN3 domains (1 μM diluted in a 3-fold dilution series) as analytes simultaneously in the horizontal orientation over the captured hCD8A-Fc surfaces, with a sixth analyte channel containing only running buffer PBST. All interactions were measured at 100 uL/min flow rate with association and dissociation times being 4, 30 minutes respectively. Ligand surface regeneration was achieved by 1 short pulse of 0.85% phosphoric acid (18 s contact time at 100 uL/min). Data analyses were performed using Bio-Rad ProteOn Manager software (version 3.1.0.6). Raw data were double referenced by subtraction of the interspot (empty chip surface, no protein immobilized or captured) signals to correct the non-specific binding of the FN3 domain to the pre-coated GAH-Fc IgG surface, followed by a double referencing using the buffer blank response (to correct for any baseline drift resulting from ligand dissociation over time). It has been consistently observed in multiple analyses that the anti-CD8A FN3 domain binding data do not conform well to the 1:1 simple Langmuir binding model, implying either the reagents issues and/or the intrinsically complicated binding mechanisms that can't be accounted for using a simple 1:1 binding mode. Given that the GAH-Fc capture of hCD8A-Fc format is the least disruptive relative to other formats in introducing potential experimental artifacts (such as ligand activity loss and/or artificial eptiopes/heterogeneous ligand population due to amine coupling), it is considered that the results from the GAH-Fc capture experiments reported here represent the most reliable ProteOn SPR data, despite the non-conforming 1:1 Langmuir fits observed in many instances. A heterogeneous ligand model was chosen to fit the data assuming two different ligand species, either due to the heterogeneity in the ligand protein population or due to potential different mechanisms for each FN3 domain binding to the 2 hCD8A monomers in the Fc fusion protein. In this case, because each anti-CD8A FN3 domain would have separate affinities, the resultant sensorgram reflects the sum of two independent reactions with two sets of rate constants, which were reported for each FN3 domain binding.

TABLE 6

Summary of kinetic affinities for top six anti-CD8A FN3 domain candidates.

| Sample | Lower Affinity Population | | | Higher Affinity Population | | |
|---|---|---|---|---|---|---|
| (SEQ ID NO:) | $k_a$ (1/Ms) | $k_d$ (1/s) | $K_D$ (nM) | $k_a$ (1/Ms) | $k_d$ (1/s) | $K_D$ (nM) |
| P282DR9P1359_F5 (79) | 3.48E+04 | 6.60E−05 | 6.6 | 3.80E+05 | 1.42E−05 | 0.04 |
| P282DR9P1359_F7 (81) | 4.03E+04 | 3.65E−04 | 12 | 4.04E+05 | 7.99E−05 | 0.5 |
| P282DR9P1359_G7 (83) | 6.84E+04 | 5.51E−05 | 2.1 | 2.76E+05 | 1.49E−05 | 0.05 |
| P282ER9P1360_C8 (89) | 3.09E+04 | 9.52E−05 | 4.1 | 2.18E+05 | 4.71E−05 | 0.2 |
| P283AR9P1362_D6 (122) | 5.62E+04 | 3.12E−05 | 0.98 | 1.55E+05 | 1.00E−06 | 0.03 |
| P282DR9P1359_C5 (68) | 1.92E+04 | 1.27E−04 | 6.5 | 3.00E+05 | 5.79E−06 | 0.02 |

Note:

Affinity, $K_D$ = kd/ka.

Example 6: Labeling of Anti-CD8a FN3 Domains with DFO And 89ZR

Anti-CD8A FN3 domains were modified to include a single cysteine residue for conjugation of maleimide containing chelators or PET labels. Synthetic plasmid DNA encoding clones P282DR9P1359_F5, P282DR9P1359_F7, P282DR9P1359_G7, P282ER9P1360_C8, P283AR9P1362_D6, and P282DR9P1359_C5 with a mutation of residue E54 to cysteine were synthesized at DNA2.0 (Table 7). E54 was chosen as the position for mutation based on earlier studies that demonstrated maintenance of binding affinity, stability, and expression levels for other FN3 domains mutated at this residue (Goldberg S. et al. Protein Engineering Design and Selection 2016 Epub ahead of print).

TABLE 7

Modified anti-CD8A FN3 domain molecules

| Original Clone | SEQID NO | Clone with E54C | SEQID No |
|---|---|---|---|
| P282DR9P1359_F5 | 79 | CD8S368 | 229 |
| P282DR9P1359_F7 | 81 | CD8S367 | 230 |
| P282DR9P1359_G7 | 83 | CD8S370 | 231 |
| P282ER9P1360_C8 | 89 | CD8S365 | 232 |
| P283AR9P1362_D6 | 122 | CD8S369 | 233 |
| P282DR9P1359_C5 | 68 | CD8S366 | 234 |

Anti-CD8A FN3 domins modified with a free cysteine were conjugated to Deferoxamine (DFO) in order to chelate radiometals. 0.5 mL of a 100-500 μM anti-CD8A FN3 domain solution was combined with 10 μL of 500 mM TCEP (Sigma, cat. #646547), gently flushed with nitrogen, and incubated for 1 hour at room temperature. 1.0 mL of saturated ammonium sulfate (4.02 M) was added to each tube to reach a final concentration of 3.2M before incubation on ice for 10 minutes and centrifugation at 16,000×g or higher to pellet the protein. The resulting pellet was resuspended and washed in 1.0 mL of 3.2 M ammonium sulfate supplemented with 100 mM sodium phosphate pH 7.2 and 1 mM EDTA before centrifuging again. After the second centrifugation step, the resulting pellet was dissolved in 100 mM sodium phosphate 7. 0, 1 mM EDTA and combined with 10 uL of 50 mM DFO solution to make a final molar ratio of 5:1 DFO to anti-CD8A. This reaction was allowed to proceed at room temperature for 30 minutes before quenching with 5.0 microliters of beta-mercaptoethanol. Excess DFO was finally removed by a variety of methods including a second round of ammonium sulfate precipitation as described above, passing through a desalting column such as Zeba 7k column (Pierce Cat #89889), or by purification with nickle-NTA resin (Qiagen #30450). Anti-CD8A FN3domain-DFO conjugates were formulated in 1×PBS for further analysis.

Following conjugation to DFO, the binding of each anti-CD8A FN3 domain to recombinant human CD8 alpha was assessed by surface plasmon resonance as previously described. All samples retained tight binding to human CD8A following mutation of E54 to Cys and conjugation to DFO (Table 8).

TABLE 8

Binding affinity following DFO conjugation

| | Lower Affinity Population | | | Higher Affinity Population | | |
|---|---|---|---|---|---|---|
| Sample | $k_a$ (1/Ms) | $k_d$ (1/s) | $K_D$ (nM) | $k_a$ (1/Ms) | $k_d$ (1/s) | $K_D$ (nM) |
| CD8S365-DFO | 4.41E+03 | 4.29E−05 | 9.73 | 6.80E+04 | 4.18E−05 | 0.6 |
| CD8S366-DFO | 5.85E+03 | 1.06E−04 | 18.2 | 7.95E+04 | 7.01E−05 | 0.9 |
| CD8S367-DFO | 1.09E+04 | 9.75E−04 | 89.1 | 8.45E+04 | 1.31E−04 | 1.55 |
| CD8S368-DFO | 7.32E+03 | 9.98E−05 | 13.6 | 1.08E+05 | 2.53E−05 | 0.23 |
| CD8S369-DFO | 2.87E+03 | ≤1E−05 | ≤3.4 | 3.73E+04 | ≤1E−05 | ≤0.3 |
| CD8S370-DFO | 5.91E+03 | 7.65E−05 | 13 | 4.64E+04 | ≤2E−05 | ≤0.3 |

Example 7: Binding of Anti-CD8a FN3 Domains to Human and Cyno T-Cells

A full dose response binding curve was generated for the nineteen selected anti-CD8A FN3 domains. Each candidate was diluted to 20 μM in PBS followed by a 1:3 dilution series to generate either an 11-point or an 18-point dose response curve. Human or cyno CD8+ T cells were incubated with the diluted FN3 domain for 1 hour at 4° C. Cells were washed once with PBS and incubated with an anti-centyrin antibody (PAB25) for 1 hour at 4° C. The cells were washed twice with PBS, followed by incubation with a PE-secondary, anti-CD3-PacB, anti-CD4-APC, and a viability dye. Finally, cells were washed and resuspended in PBS for flow cytometric analysis using a BD Canto Instrument. CD8 T cells were defined as live CD3+CD4-cells. Median fluorescence intensity of the bound Centyrins (PE channel) and % of cells showing positive staining calculated using Cytobank software. Results were graphed using Prism and $EC_{50}$ values were calculated using the 4-parameter dose response variable slope equation.

A MesoScale Discovery-Cell Affinity Technology (MSD-CAT) based equilibrium cell-binding assay was performed to determine the affinity of the top six anti-CD8A candidates binding to primary human cytotoxic T cell surface CD8A receptors. Each anti-CD8A FN3 domain at a constant concentration of 50 pM was pre-incubated with 10 different concentrations of primary cytotoxic CD8 T cells (columns 2-11 in a row). Cell viability was checked prior to the binding measurements and a >85% viability was desired for valid analysis. Since these cells were from different donors, in case of donor-to-donor variations, only cells of the same donors were combined together. Each individual anti-CD8A FN3 domain binding was measured in replicates using cells from the same donors. Cells and FN3 domains were incubated overnight at 4° C. on a rotator to reach equilibrium. Following the incubation the cells were spun down along with cell bound anti-CD8A FN3 domains and the unbound (free) anti-CD8A FN3 domains in the supernatants is quantified using MSD assays where biotinylated recombinant hCD8A-Fc protein was captured at 0.6 ug/mL in assay buffer to streptavidin MSD plates overnight ~16 hours at 4° C. After blocking the plate, supernatant with free anti-CD8A FN3 domains was added to the plate and incubated for 1 hr, then followed by SulfoTag pAb139 (In-house) detection at 1.6 μg/ml. A buffer control without any FN3 domain and hCD8A (plate background binding control) in column 1 and FN3 domain alone control without hCD8A (100% free/unbound) in column 12 were included. Mouse Anti-hCD8A mAb (mlgGlk, BD Biosciences, cat #555364, clone RPA-T8) was included as a postive control. Tencon27 was included in the initial assay validation as a negative control and no significant binding was observed, and therefore, was not included in the later cell binding due to the cell availability. Plates were read immediately on the MSD Sector Imager 6000™ Reader for luminescence levels after adding MSD Read Buffer by diluting 1:4 of stock into H2O.

Raw MSD data were exported and analysed in Prism using a non-linear fit with variable slope function to derive the Bmax and Hillslope values. Only those with converged Bmax values and hillslope within the range of −1.5~−0.5 (ideal −1.0) will be considered for further analysis. Binding data were then normalized using the Bmax values to calculate the normalized % free FN3 domains. A surface CD8 density of 50,000 receptors per cell was used for the receptor concentration calculation. A saturation criterion of <20% free Centyrin at highest CD8 cell concentrations was required to determine the affinity using a "Solution Affinity Equation for normalized data" for a 1:1 binding model.

Anti-CD8A FN3 domains bound to primary cells with affinities ranging from 0.167 to 2.81 nM (Table 9).

TABLE 9

Summary of $EC_{50}$ values for top six anti-CD8A FN3 domain candidates.

| Clone ID (SEQ ID NO:) | EC50 Binding to Human T-cells by Flow Cytometry (nM) | EC50 Binding to cyno T-cells by Flow Cytometry (nM) | Affinity for Human T-cells by MSD-CAT (nM) |
|---|---|---|---|
| CD8S365 (232) | 556.0 | 123.6 | 0.167 |
| CD8S366 (234) | 162.7 | 69.5 | 0.123 |
| CD8S367 (230) | 194.5 | 50.8 | 0.225 |
| CD8S368 (229) | 154.7 | 70.0 | 0.459 |
| CD8S369 (233) | 124.2 | 72.3 | 2.81 |
| CD8S370 (231) | 208.7 | 67.6 | 0.869 |

Example 8: Activation of Human T-Cells

De Novo Activation

In order to determine if the anti-CD8A FN3 domains activate T cells, a flow cytometry assay was performed to monitor changes in T cell activation markers. Six anti-CD8A FN3 domains were evaluated for T-cell activation. De novo activation was assessed by incubating the FN3 domains at either 1 μM or 10 nM in duplicate with human pan-T cells in media for 4 days. Two independent donors were tested. Plate bound anti-CD3 was used a positive control at 2 doses, 0.1 ug/mL and 0.01 ug/mL. PBS was used as a negative control. Cells were then stained with a viability dye and the following panel of antibodies: CD4-FITC, CD3-PerCP-Cy5.5, CD69-PacB, CD45RA-BV605, CD25-BV650, CD127-PE, and CD137-PE-Cy7. CD8+ cells were defined as live CD3+CD4− cells and were profiled for each T-cell activation marker. Median fluorescence intensity values were calculated using FlowJo software and replicate values were averaged. Results are summarized in Table 10A (donor 022) and 10B (donor 146). For 365, 366, 367, 368, and 370, small changes in the T cell activation markers were observed in only 1 out of the 2 donors tested at the highest dose level of 1 μM. These changes were absent in both donors at the 10 nM dose, suggesting the molecules do not activate T cells de novo at relevant concentrations. The 369 molecule does appear to significantly activate CD137 expression in both donors at the highest dose level.

TABLE 10

Median Fluorescence Intensity (MFI) values for various T cells activation markers on CD8+ T cells for Donor 022 (A) and Donor 146 (B)

| Donor | Sample (SEQ ID NO:) | Anti-CD8A FN3 conc μM | Anti-CD3 ug/mL | CD45RA MFI | CD25 MFI | CD69 MFI | CD127 MFI | CD137 MFI |
|---|---|---|---|---|---|---|---|---|
| | | | | A | | | | |
| 022 | PBS control | 0 | 0 | 12856 | 571 | 223 | 651 | 296 |
| 022 | PBS control | 0 | 0.01 | 13133 | 707 | 403 | 517 | 343 |
| 022 | PBS control | 0 | 0.1 | 11394 | 1333 | 1694 | 158 | 529 |
| 022 | CD8S366 (234) | 1 | 0 | 15054 | 949 | 477 | 425 | 310 |
| 022 | CD8S366 (234) | 0.01 | 0 | 13336 | 814 | 230 | 586 | 301 |
| 022 | CD8S368 (229) | 1 | 0 | 12992 | 858 | 698 | 367 | 329 |
| 022 | CD8S368 (229) | 0.01 | 0 | 15262 | 677 | 276 | 489 | 306 |
| 022 | CD8S367 (230) | 1 | 0 | 15409 | 796 | 401 | 511 | 297 |
| 022 | CD8S367 (230) | 0.01 | 0 | 13666 | 723 | 261 | 502 | 312 |
| 022 | CD8S370 (231) | 1 | 0 | 12946 | 916 | 572 | 376 | 353 |
| 022 | CD8S370 (231) | 0.01 | 0 | 14973 | 776 | 353 | 435 | 331 |
| 022 | CD8S365 (232) | 1 | 0 | 13935 | 904 | 562 | 367 | 328 |
| 022 | CD8S365 (232) | 0.01 | 0 | 15156 | 697 | 243 | 504 | 323 |
| 022 | CD8S369 (233) | 1 | 0 | 13661 | 783 | 440 | 441 | 5122 |
| 022 | CD8S369 (233) | 0.01 | 0 | 16513 | 717 | 251 | 596 | 416 |
| 022 | TenCon | 1 | 0 | 14920 | 702 | 284 | 447 | 334 |
| | | | | B | | | | |
| 146 | PBS | 0 | 0 | 7172 | 627 | 61 | 1313 | 500 |
| 146 | PBS | 0 | 0.01 | 8076 | 681 | 153 | 1296 | 617 |
| 146 | PBS | 0 | 0.1 | 5171 | 1462 | 1100 | 139 | 798 |
| 146 | CD8S366 (234) | 1 | 0 | 8531 | 673 | 95 | 1368 | 589 |
| 146 | CD8S366 (234) | 0.01 | 0 | 9414 | 623 | 74 | 1615 | 559 |
| 146 | CD8S368 (229) | 1 | 0 | 8386 | 691 | 96 | 1301 | 561 |
| 146 | CD8S368 (229) | 0.01 | 0 | 9147 | 628 | 82 | 1424 | 586 |
| 146 | CD8S367 (230) | 1 | 0 | 8167 | 660 | 95 | 1322 | 581 |
| 146 | CD8S367 (230) | 0.01 | 0 | 8734 | 586 | 77 | 1479 | 571 |
| 146 | CD8S370 (231) | 1 | 0 | 8590 | 737 | 86 | 1362 | 583 |
| 146 | CD8S370 (231) | 0.01 | 0 | 7934 | 635 | 71 | 1526 | 559 |
| 146 | CD8S365 (232) | 1 | 0 | 8344 | 813 | 85 | 1238 | 586 |
| 146 | CD8S365 (232) | 0.01 | 0 | 8460 | 628 | 80 | 1355 | 605 |
| 146 | CD8S369 (233) | 1 | 0 | 8778 | 681 | 92 | 1369 | 5690 |
| 146 | CD8S369 (233) | 0.01 | 0 | 7862 | 591 | 74 | 1498 | 784 |
| 146 | TenCon | 1 | 0 | 7325 | 609 | 78 | 1198 | 574 |
| 146 | TenCon | 0.01 | 0 | 7764 | 596 | 66 | 1281 | 530 |

TABLE 10

Median Fluorescence Intensity (MFI) values for various T cells activation markers on CD8+ T cells for Donor 022 (A) and Donor 146 (B)

| Donor | Sample (SEQ ID NO:) | Anti-CD8A FN3 conc μM | Anti-CD3 ug/mL | CD45RA MFI | CD25 MFI | CD69 MFI | CD127 MFI | CD137 MFI |
|---|---|---|---|---|---|---|---|---|
| A | | | | | | | | |
| 022 | PBS control | 0 | 0 | 12856 | 571 | 223 | 651 | 296 |
| 022 | PBS control | 0 | 0.01 | 13133 | 707 | 403 | 517 | 343 |
| 022 | PBS control | 0 | 0.1 | 11394 | 1333 | 1694 | 158 | 529 |
| 022 | CD8S366 (234) | 1 | 0 | 15054 | 949 | 477 | 425 | 310 |
| 022 | CD8S366 (234) | 0.01 | 0 | 13336 | 814 | 230 | 586 | 301 |
| 022 | CD8S368 (229) | 1 | 0 | 12992 | 858 | 698 | 367 | 329 |
| 022 | CD8S368 (229) | 0.01 | 0 | 15262 | 677 | 276 | 489 | 306 |
| 022 | CD8S367 (230) | 1 | 0 | 15409 | 796 | 401 | 511 | 297 |
| 022 | CD8S367 (230) | 0.01 | 0 | 13666 | 723 | 261 | 502 | 312 |
| 022 | CD8S370 (231) | 1 | 0 | 12946 | 916 | 572 | 376 | 353 |
| 022 | CD8S370 (231) | 0.01 | 0 | 14973 | 776 | 353 | 435 | 331 |
| 022 | CD8S365 (232) | 1 | 0 | 13935 | 904 | 562 | 367 | 328 |
| 022 | CD8S365 (232) | 0.01 | 0 | 15156 | 697 | 243 | 504 | 323 |
| 022 | CD8S369 (233) | 1 | 0 | 13661 | 783 | 440 | 441 | 5122 |
| 022 | CD8S369 (233) | 0.01 | 0 | 16513 | 717 | 251 | 596 | 416 |
| 022 | TenCon | 1 | 0 | 14920 | 702 | 284 | 447 | 334 |
| B | | | | | | | | |
| 146 | PBS | 0 | 0 | 7172 | 627 | 61 | 1313 | 500 |
| 146 | PBS | 0 | 0.01 | 8076 | 681 | 153 | 1296 | 617 |
| 146 | PBS | 0 | 0.1 | 5171 | 1462 | 1100 | 139 | 798 |
| 146 | CD8S366 (234) | 1 | 0 | 8531 | 673 | 95 | 1368 | 589 |
| 146 | CD8S366 (234) | 0.01 | 0 | 9414 | 623 | 74 | 1615 | 559 |
| 146 | CD8S368 (229) | 1 | 0 | 8386 | 691 | 96 | 1301 | 561 |
| 146 | CD8S368 (229) | 0.01 | 0 | 9147 | 628 | 82 | 1424 | 586 |
| 146 | CD8S367 (230) | 1 | 0 | 8167 | 660 | 95 | 1322 | 581 |
| 146 | CD8S367 (230) | 0.01 | 0 | 8734 | 586 | 77 | 1479 | 571 |
| 146 | CD8S370 (231) | 1 | 0 | 8590 | 737 | 86 | 1362 | 583 |
| 146 | CD8S370 (231) | 0.01 | 0 | 7934 | 635 | 71 | 1526 | 559 |
| 146 | CD8S365 (232) | 1 | 0 | 8344 | 813 | 85 | 1238 | 586 |
| 146 | CD8S365 (232) | 0.01 | 0 | 8460 | 628 | 80 | 1355 | 605 |
| 146 | CD8S369 (233) | 1 | 0 | 8778 | 681 | 92 | 1369 | 5690 |
| 146 | CD8S369 (233) | 0.01 | 0 | 7862 | 591 | 74 | 1498 | 784 |
| 146 | TenCon | 1 | 0 | 7325 | 609 | 78 | 1198 | 574 |
| 146 | TenCon | 0.01 | 0 | 7764 | 596 | 66 | 1281 | 530 |

Pan T-Cell Activation

In order to determine if the anti-CD8A FN3 domains can affect markers of T cell activation in pan-actived T cells, the anti-CD8A FN3 domains were also evaluated in combination with a low dose of plate bound CD3. In this assay, a sub-optimal concentration (0.01 μg/mL) of plate bound anti-CD3 was used to activate the T cells in the presence of either 1 uM or 10 nM anti-CD8A. After 4 days, the cells were assessed using the same panel and gating strategy as described above. Two independednt donors were tested. Median fluorescence intensity values were calculated using FlowJo software and replicate values were averaged. Results are summarized in Tables 11A (donor 022) and 11B (donor 146).

TABLES 11A and B

Median Fluorescence Intensity (MFI) values for various T cells activation markers on CD8+ T cells for Donor 022 (A) and Donor 146 (B) in the presence of plate bound CD3.

A

| Donor | Sample (SEQ ID NO:) | Anti-CD8A FN3 conc μM | Anti-CD3 μg/mL | CD45RA MFI | CD25 MFI | CD69 MFI | CD127 MFI | CD137 MFI |
|---|---|---|---|---|---|---|---|---|
| 022 | PBS control | 0 | 0 | 12856 | 571 | 223 | 651 | 296 |
| 022 | PBS control | 0 | 0.01 | 13133 | 707 | 403 | 517 | 343 |
| 022 | PBS control | 0 | 0.1 | 11394 | 1333 | 1694 | 158 | 529 |
| 022 | CD8S366 (234) | 1 | 0.01 | 11918 | 892 | 1005 | 369 | 376 |
| 022 | CD8S366 (234) | 0.01 | 0.01 | 13417 | 1068 | 848 | 384 | 399 |
| 022 | CD8S368 (229) | 1 | 0.01 | 11311 | 1147 | 1279 | 260 | 428 |
| 022 | CD8S368 (229) | 0.01 | 0.01 | 13441 | 760 | 599 | 499 | 348 |
| 022 | CD8S367 (230) | 1 | 0.01 | 13271 | 1135 | 1127 | 367 | 385 |
| 022 | CD8S367 (230) | 0.01 | 0.01 | 14521 | 960 | 636 | 483 | 362 |
| 022 | CD8S370 (231) | 1 | 0.01 | 15138 | 1103 | 890 | 407 | 378 |
| 022 | CD8S370 (231) | 0.01 | 0.01 | 14230 | 875 | 612 | 431 | 355 |
| 022 | CD8S365 (232) | 1 | 0.01 | 14395 | 1112 | 907 | 380 | 407 |
| 022 | CD8S365 (232) | 0.01 | 0.01 | 14006 | 1175 | 1063 | 297 | 430 |
| 022 | CD8S369 (233) | 1 | 0.01 | 13735 | 877 | 759 | 464 | 5457 |
| 022 | CD8S369 (233) | 0.01 | 0.01 | 13864 | 842 | 617 | 450 | 498 |
| 022 | TenCon | 1 | 0.01 | 14687 | 791 | 553 | 408 | 358 |
| 022 | TenCon | 0.01 | 0.01 | 13090 | 759 | 630 | 464 | 368 |

B

| Donor | Sample (SEQ ID NO:) | Anti-CD8A FN3 conc μM | Anti-CD3, μg/mL | CD45RA MFI | CD25 MFI | CD69 MFI | CD127 MFI | CD137 MFI |
|---|---|---|---|---|---|---|---|---|
| 146 | PBS control | 0 | 0 | 12856 | 571 | 223 | 651 | 296 |
| 146 | PBS control | 0 | 0.01 | 13133 | 707 | 403 | 517 | 343 |
| 146 | PBS control | 0 | 0.1 | 11394 | 1333 | 1694 | 158 | 529 |
| 146 | CD8S366 (234) | 1 | 0.01 | 6798 | 876 | 163 | 1095 | 632 |
| 146 | CD8S366 (234) | 0.01 | 0.01 | 8589 | 775 | 158 | 1077 | 637 |
| 146 | CD8S368 (229) | 1 | 0.01 | 6576 | 945 | 175 | 1105 | 662 |
| 146 | CD8S368 (229) | 0.01 | 0.01 | 7608 | 843 | 200 | 950 | 678 |
| 146 | CD8S367 (230) | 1 | 0.01 | 6447 | 897 | 173 | 1088 | 672 |
| 146 | CD8S367 (230) | 0.01 | 0.01 | 7899 | 801 | 175 | 1031 | 655 |

TABLES 11A and B-continued

Median Fluorescence Intensity (MFI) values for various T cells activation markers on CD8+ T cells for Donor 022 (A) and Donor 146 (B) in the presence of plate bound CD3.

| | | | | | | | | |
|---|---|---|---|---|---|---|---|---|
| 146 | CD8S370 (231) | 1 | 0.01 | 7327 | 992 | 169 | 1055 | 687 |
| 146 | CD8S370 (231) | 0.01 | 0.01 | 8676 | 790 | 183 | 946 | 675 |
| 146 | CD8S365 (232) | 1 | 0.01 | 6624 | 977 | 172 | 1059 | 670 |
| 146 | CD8S365 (232) | 0.01 | 0.01 | 7902 | 843 | 193 | 985 | 659 |
| 146 | CD8S369 (233) | 1 | 0.01 | 7660 | 933 | 165 | 1149 | 7114 |
| 146 | CD8S369 (233) | 0.01 | 0.01 | 7892 | 854 | 187 | 989 | 842 |
| 146 | TenCon | 1 | 0.01 | 8352 | 829 | 170 | 1026 | 658 |
| 146 | TenCon | 0.01 | 0.01 | 7627 | 761 | 185 | 1043 | 673 |

Cytokine Response

Figure 1B:
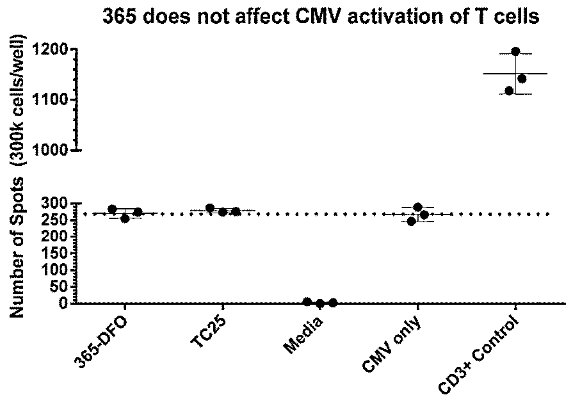
Figure 1C:
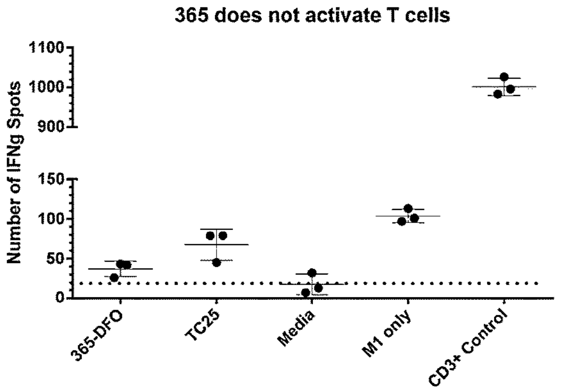
Figure 1D:
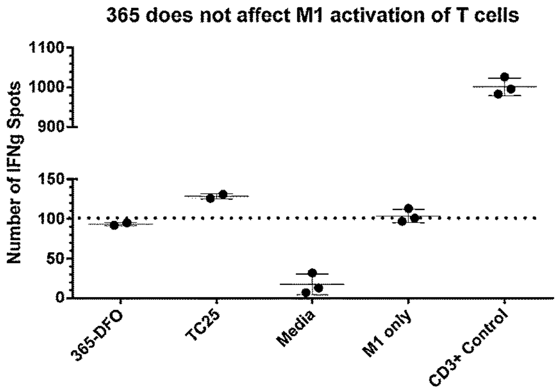

In order to determine if any of the changes observed in the activation markers resulting in changes in cytokine production, antigen-dependent T cell activation assays were also performed using two anti-CD8A FN3 domains. For one set of assays, either CMV reactive or M1 reactive human PBMCs were thawed and rested overnight at 37° C. in 6 well plates. The following day, the PBMCs were harvested by pipetting, counted, and plated onto IFNg Mabtech ELISpot plates in the presence or absence of 10 μg/mL peptide. 1 μM anti-CD8A FN3-DFO conjugate was added to the wells and plates were allowed to incubate at 37° C. for approximately 24 hours undisturbed. The cells were removed, and the plates were washed 5 times with PBS. The supplied detection antibody was added, and plates were incubated for 2 hours. The plates were again washed, and the kit substrate was added to each well. Plates were developed for approximately 5 minutes before the reaction was stopped by running the plate under water. Plates were dried upside down overnight in the dark. Plates were read on the AID EliSpot Reader and spot counts were generated using the AID EliSpot Software. Results were graphed in Prism. Results are summarized in FIG. 1. In this assay, 365-DFO does not increase the number of IFNg spots compared to media alone or non-CD8A binding TenCon control in the absence of peptide (FIG. 1A, 1C). Peptide and CD3 are included as positive controls. In the presence of peptide, the 365-DFO does not change the number of IFNg spots compared to peptide alone or peptide with non-CD8A binding tencon (FIG. 1B, 1D). Media is included as a negative control and CD3 is included as a positive control. These results suggest that the centyrin does not affect T cell activation.

Figure 2A:
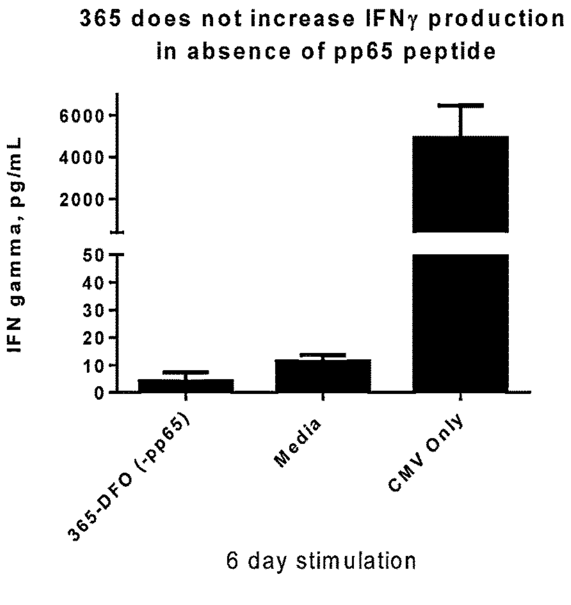
FIGS. 2A and 2B. The CD8S365-DFO conjugate does not activate T cells de novo and does not modulate the antigen dependent activation of T cells in a 6-day $INF^{\gamma}$ MSD assay. CMV reactive T cells were treated with 365-DFO in the absence (A) or presence (B) of CMV peptides.
Figure 2B:
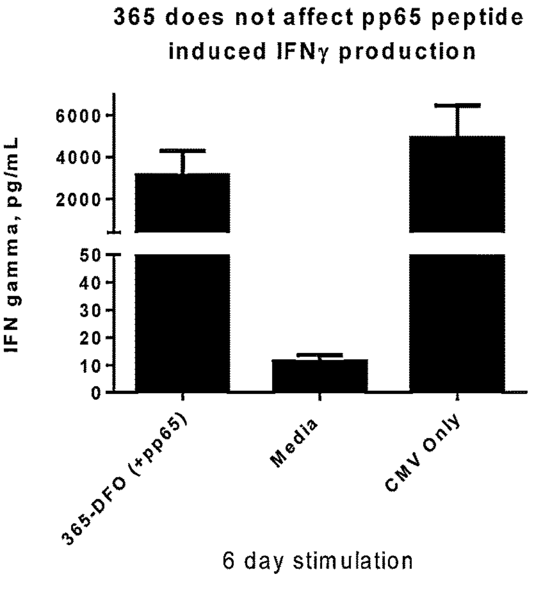

To confirm these results in a longer-term assay, IFN-gamma levels were also measured in a 6-Day activation assay. For this study, CMV reactive PBMCs were incubated in triplicate with anti-CD8A FN3 domains at 1 uM in the presence or absence of 0.25 μg/mL pp65 peptide. Cells were incubated for 6 days at 37° C. At each timepoint the cells were centrifuged and supernatant was harvested. Samples were stored at −80° C. until analyzed. Thawed samples were analyzed for IFN-gamma using a single-plex Meso Scale Discovery (MSD) based ELISA. For this assay, a standard curve was prepared as per manufacturer's instructions. Samples and standards were added to pre-coated 96 well MSD plates. After a 2-hour incubation, the kit detection antibody was added. After another 2-hour incubation, plates were washed three times followed by the addition of the supplied read buffer. Plates were read on MSD Sector Imager 6000 plate reader. Raw MSD data files were analyzed against the standard curves generated using the MSD Discovery Workbench software. The analyzed data graphed using the Tibco Spotfire program. Results are summarized in FIG. 2. In this assay, 365-DFO does not increase the secretion of IFNg into the media compared to media alone in the absence of peptide (FIG. 2A). CMV peptide is included as a positive control. In the presence of peptide, the 365-DFO also does not change the amount of IFNg secretion compared to peptide alone (FIG. 2B). Media is included as a negative control. These results suggest that the centyrin does not affect T cell activation.

Example 9: Labeling of Anti-CD8A FN3 Domains with 1124/1125

The current method to radiolabel CD8S365 with iodine-124 to produce [124I]-IPEM CD8S 365 (Scheme 1) was adapted from literature procedures (*Bioconjugate Chem.* 1991, 2, 435-440; *ChemistryOpen* 2015, 4, 174-182).

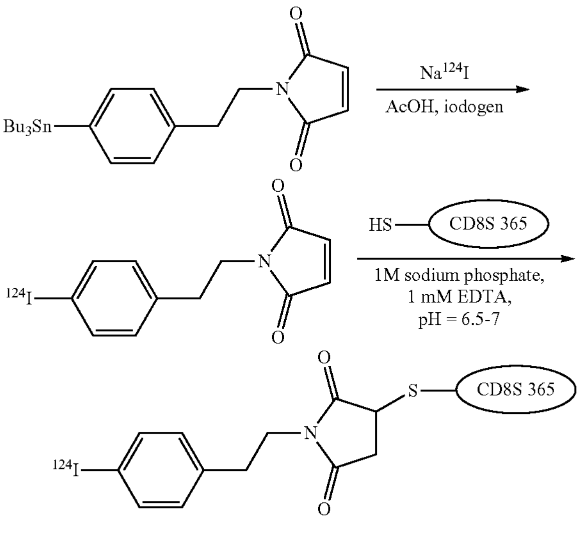

Scheme 1: Synthesis of [$^{124}$I]-IPEM CD8S 365

To a 1.5 mL Eppendorf vial was added, in order, $Na^{124}I$ solution (≤13 μL, ≤2.5 mCi), AcOH (5 μL to acidify the solution), 1-(4-(tributylstannyl)phenethyl)-1H-pyrrole-2,5-dione (75 μL, 1.00 mg/mL in MeCN) and iodogen (5 μL, 1.00 mg/mL in MeCN) solution. The reaction was left for 5 min at room temperature.

Figure 3:
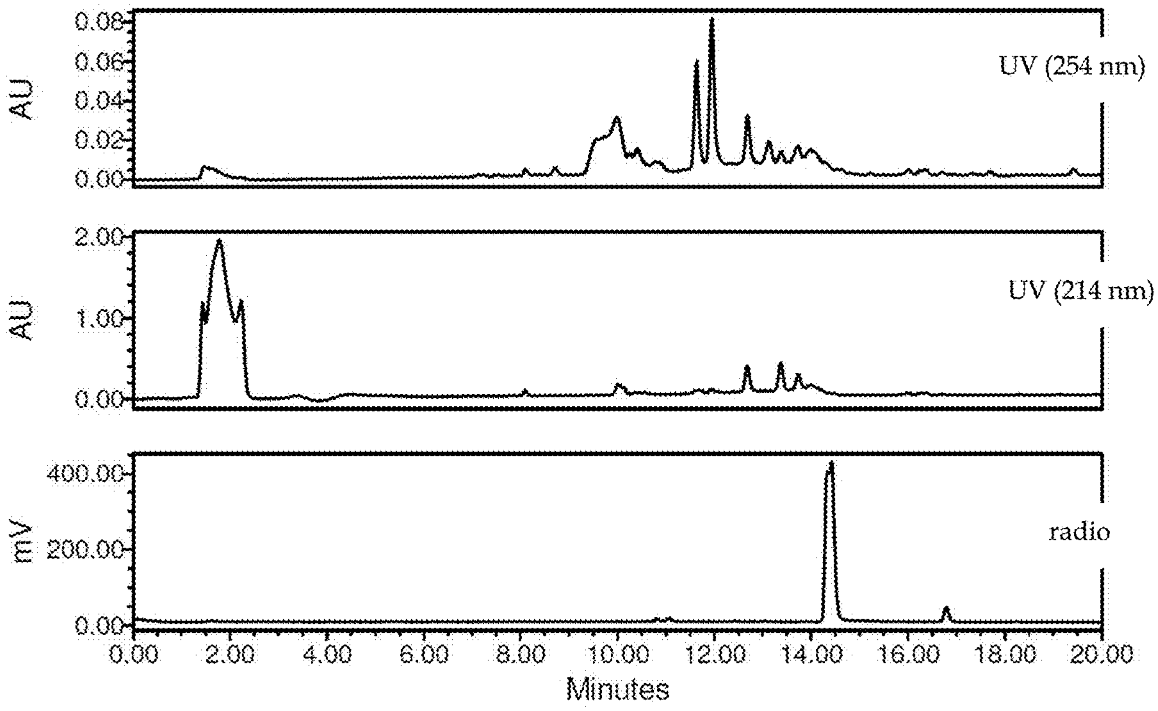
FIG. 3. Crude preparatory HPLC trace of [124I]-IPEM. Preparatory HPLC was performed using a Waters 1525 Binary HPLC pump, a Waters 2489 dual wavelength UV/Visible Detector (λ=214 and 254 nm), a Bioscan Flow Count radiodetector (B-FC-2000) and a Atlantis T3, 100 Å, 5 µm, 150×4.6 mm HPLC column. The elution profile used was as follows: solvent A=H2O (0.1% AcOH (v/v)), Solvent B=MeCN (0.1% AcOH (v/v)), flow rate=1.5 mLmin-1; initial=80% A, 20 min=0% A (linear gradient). Multiple small molecule absorbance on UV-vis traces at 254 nm (top graph) and 214 nm (middle graph) indicate presence of impurities and by-products in the crude reaction mixture. Radiotrace (bottom graph) also shows expected baseline peaks due to radiolabeled impurities.

The crude reaction mixture was diluted with 0.5 mL of 20% EtOH/$H_2O$ and was purified directly on preparatory HPLC, the retention time=14.4 min (FIG. 3). The [$^{124}$I]-IPEM was collected in a 1 dram vial that had been pre-treated with Sigma-Cote™ (then rinsed with 3 mL of 70% EtOH, followed by 3 mL of $H_2O$); total volume collected off preparatory HPLC <750 μL.

Figure 4:
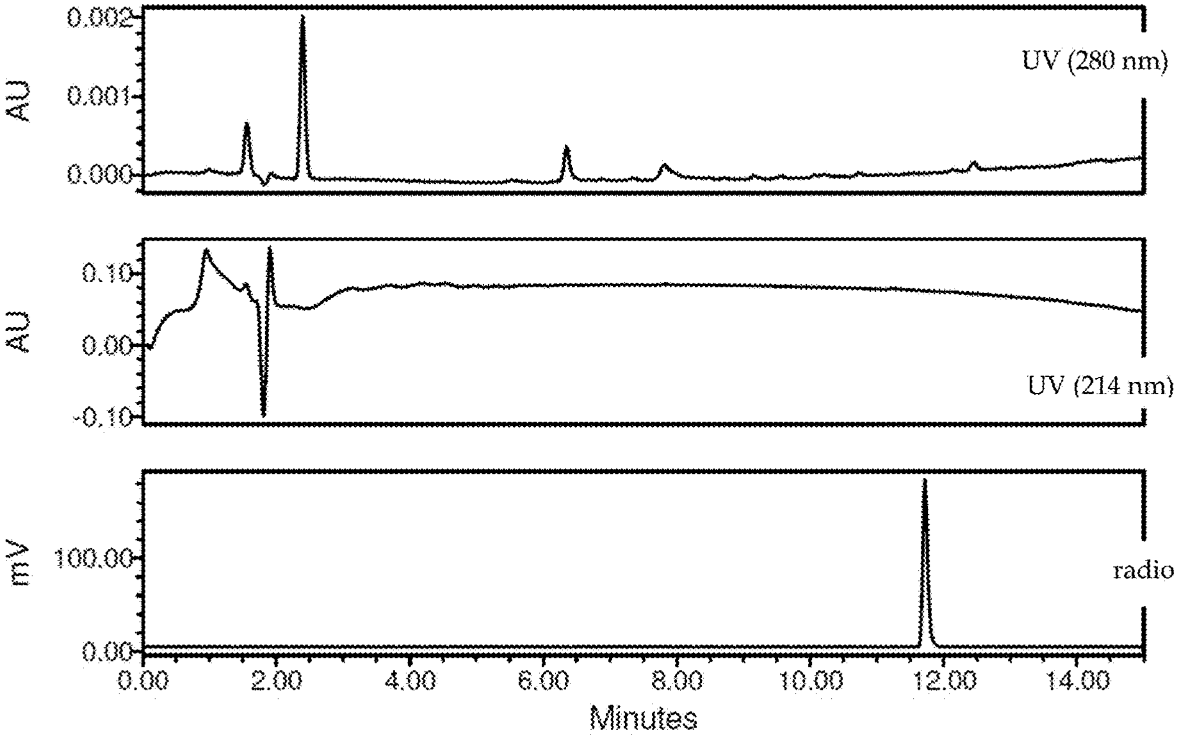
FIG. 4. Analytical HPLC trace of [124I]-IPEM. Analytical HPLC was performed using a Waters 1525 Binary HPLC pump, a Waters 2707 autosampler, a Waters 2489 dual wavelength UV/Visible Detector (λ=214 and 280 nm), a Bioscan Flow Count radiodetector (B-FC-2000) and a Phenomenex Kinetex 5 µm XB-C18 100 Å, 150×4.6 mm HPLC column. The elution profile used was as follows: solvent A=H2O (0.1% TFA (v/v)), Solvent B=MeCN (0.1% TFA (v/v)), flow rate=1 mLmin-1; initial=90% A, 15 min=0% A (linear gradient). Analytically pure [I-124] IPEM shows a single radiopeak (bottom graph) with a smooth baseline confirming successful purification. Please note that [I-124] IPEM is an organic small molecule; hence, lacking absorption at 280 nm (top graph) and 214 nm (middle graph).

An aliquot (~5-25 μCi) of the purified fraction was then injected on analytical HPLC (FIG. 4, retention time=11.7 min).

The purified [$^{124}$I]-IPEM was then concentrated under vacuum at ambient temperature to a volume of <100 μL.

Sodium phosphate buffer (1.0 M sodium phosphate, 1 mM EDTA, pH=6.86) was added (≥25 μL) to bring the pH to ~6.5-7 (checked by strip). Lastly freshly reduced CD8S 365 (c~4.57 mg/mL in 100 mM sodium phosphate buffer, 1 mM EDTA, pH=6.86), was added in appropriate amount to achieve targeted specific activity (ie. if targeting specific activity of 25 mCi/mg and 2.0 mCi of [$^{124}$I]-IPEM was collected add 17.5 μL of centyrin at c~4.57 mg/mL). The conjugation reaction was left for 60 min at ambient temperature and the reaction progress was checked to verify that the conversion exceeded 90% by iTLC.

Figure 5:
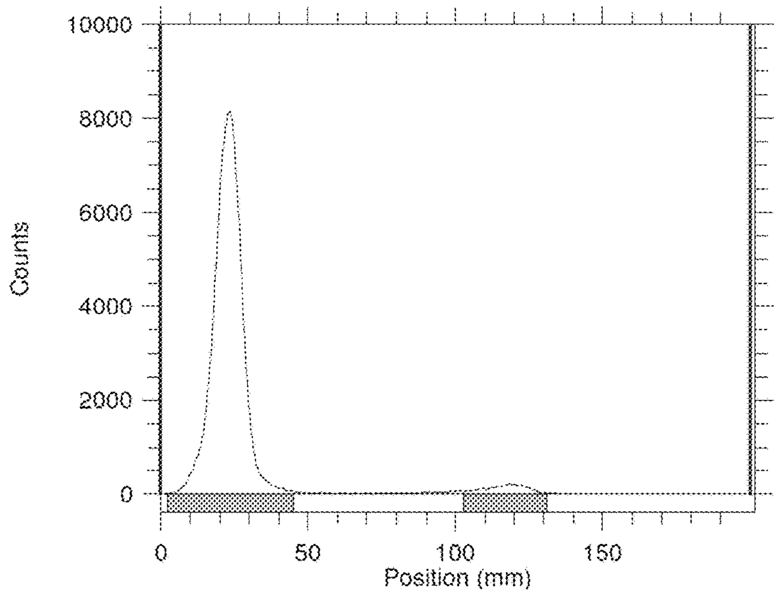
FIG. 5. Radio TLC of purified [124I]-IPEM CD8S365. The iTLC-SG plate (Agilent, cat #SGI0001) was read on a Bioscan AR-2000 radio-TLC imaging scanner. The radio TLC plate (FIG. 3) was co-spotted with 1 µL of NaI (0.1 M) and developed using citric acid (0.5 mM, pH=5) as eluent. The origin=20 mm and the solvent front=100 mm. The radio TLC eluent was prepared by dissolving 96 mg of citric acid (Spectrum cat #CI131) in 25 mL of Trace Select H2O and then Na2CO3 was added (245 µL, 2 M); the pH was checked by strip (pH=5).

Purification consisted of diluting the reaction solution with PBS/10% EtOH (1 mL, pH=7) transferring the reaction solution from the 1 dram vial into a Vivaspin 6 5 kDa MWCO centrifugal filter (see appendix for the pre-conditioning). After the transfer, the reaction Eppendorf was rinsed with PBS/10% EtOH (2×1 mL, pH=7) and the washings were added to the filter. The crude reaction mixture was centrifuged at 4000 rpm, at 20° C. for 30 min. Following centrifugation <500 μL of solution remained and was found to have a radiochemical purity (RCP) >95% by radio TLC (FIG. 5). The purified [$^{124}$I]-IPEM CD8S 365 was diluted to a volume of 500 μL with PBS/10% EtOH if the volume was <500 μL and then filtered through a Millex-GV 0.22 μm hydrophilic Durapore (PVDF) membrane.

Figure 6:
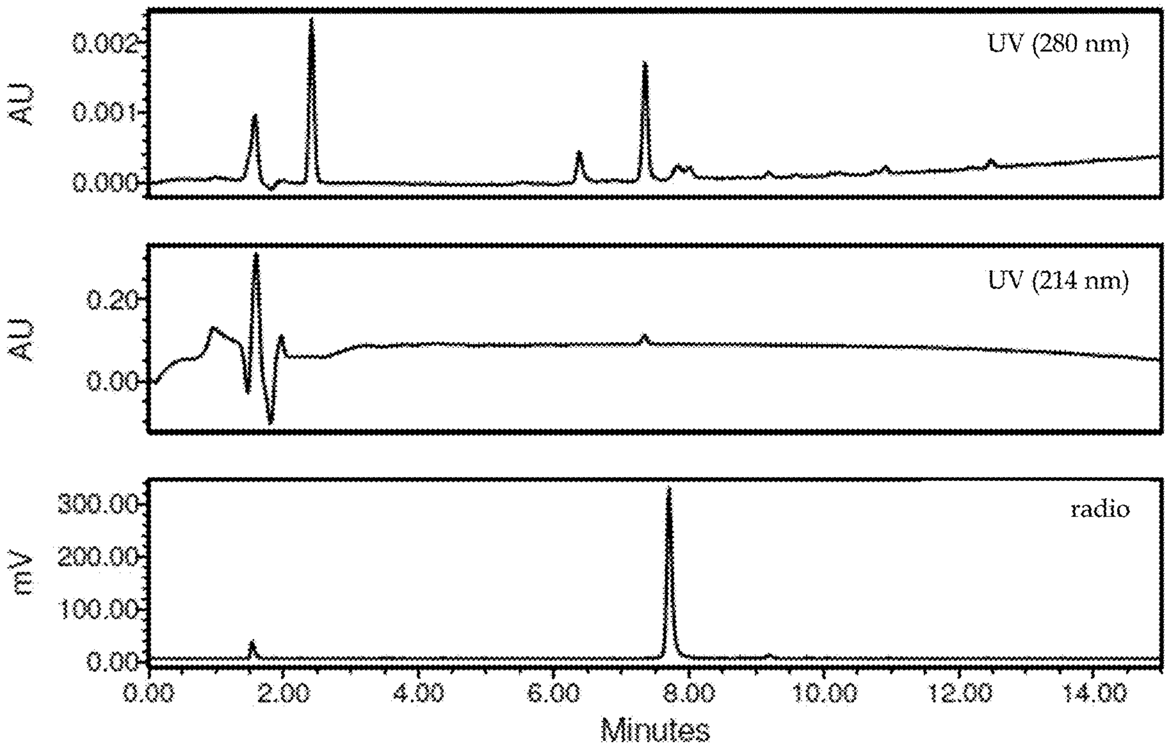
FIG. 6. Analytical HPLC trace of purified [124I]-IPEM CD8S 365. Analytical HPLC was performed using a Waters 1525 Binary HPLC pump, a Waters 2707 autosampler, a Waters 2489 dual wavelength UV/Visible Detector (λ=214 and 280 nm), a Bioscan Flow Count radiodetector (B-FC-2000) and a Phenomenex Kinetex 5 µm XB-C18 100 Å, 150×4.6 mm HPLC column. The elution profile used was as follows: solvent A=H2O (0.1% TFA (v/v)), Solvent B=MeCN (0.1% TFA (v/v)), flow rate=1 mLmin-1; initial=90% A, 15 min=0% A (linear gradient). Biomolecule (CD8S) absorbance at 280 nm (top graph) and small molecule (1124-IPEM) absorbance at 214 nm (middle graph) confirms successful conjugation reaction. UV and radio traces (bottom graph) indicate an analytically pure sample.
Figure 7:
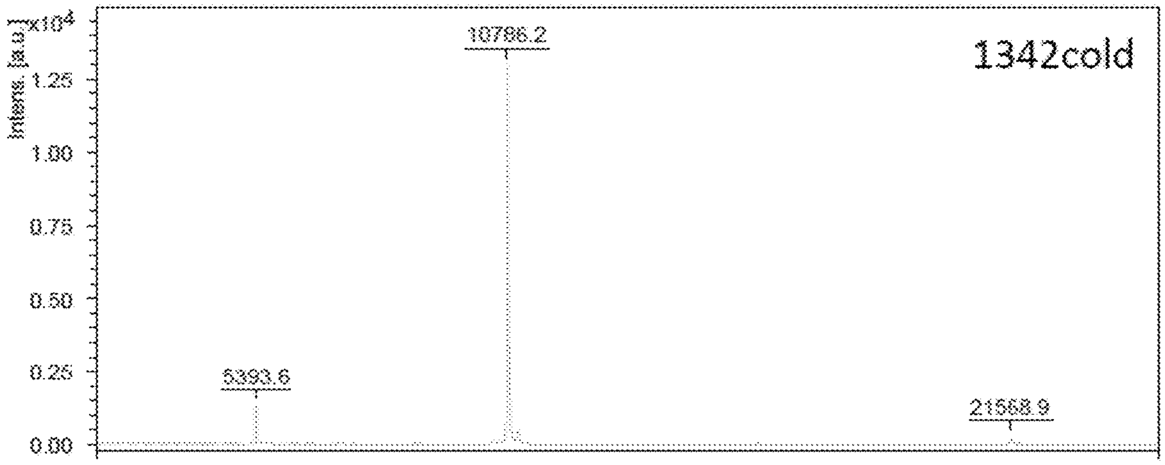
FIG. 7. MALDI-MS of IPEM CD8S365 (theoretical MW=10786.12). The MALDI-MS analysis was performed at the Biointerfaces Institute using a Bruker UltrafleXtreme MALDI TOF/TOF in positive ion mode (linear detector). A saturated solution of sinapinic acid was prepared in TA30 solvent (30:70 (v/v) MeCN:0.1% TFA in water). The sample (c=0.397 mgmL−1) was mixed in a 1:1 ratio with the matrix solution and 1 µL was spotted on the plate. A protein solution was used as an external standard.
Figure 8:
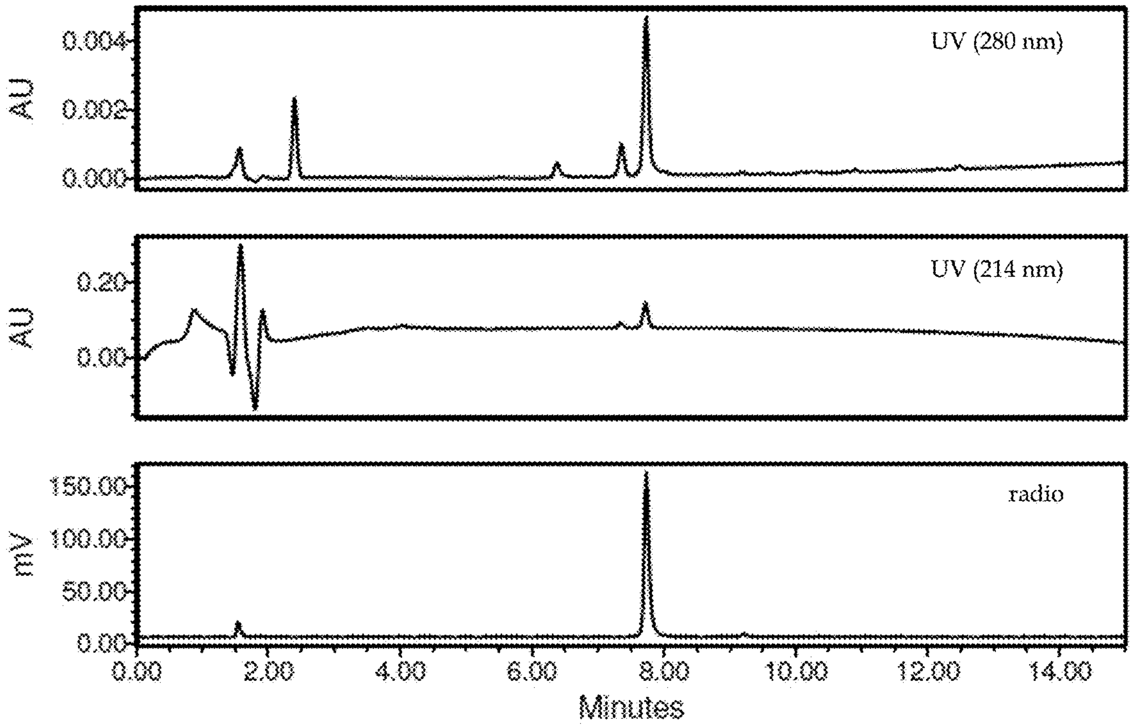
FIG. 8. Co-injection of [124I]-IPEM CD8S365 with cold standard. Analytical HPLC was performed using a Waters 1525 Binary HPLC pump, a Waters 2707 autosampler, a Waters 2489 dual wavelength UV/Visible Detector (λ=214 and 280 nm), a Bioscan Flow Count radiodetector (B-FC-2000) and a Phenomenex Kinetex 5 µm XB-C18 100 Å, 150×4.6 mm HPLC column. The elution profile used was as follows: solvent A=H2O (0.1% TFA (v/v)), Solvent B=MeCN (0.1% TFA (v/v)), flow rate=1 mLmin−1; initial=90% A, 15 min=0% A (linear gradient). Co-injection with cold sample leads to complete overlap of UV peaks (top and middle graphs), confirming the product's molecular identity (i.e. Cold and radiolabeled conjugates are identical except for the replacement of Iodine by Iodine-124)

The radiochemical yield from the protocol is ~50% with a radiochemical purity ≥95% RCP by radio TLC). Analytical reverse phase HPLC was used to determine the protein concentration and specific activity of the final product. The average integration of the peak at retention time=7.3 min in the UV at λ=280 nm was used to extrapolate the protein concentration from a calibration curve (FIG. 6 for a representative example). A co-injection with the non-radioactive cold standard IPEM CD8S 365 (MALDI analysis shown in FIG. 7) was also conducted (see FIG. 8). The bacterial endotoxin concentration was measured using the Endosafe® portable test system using a 10× dilution with LAL reagent water.

Example 10: Detection of CD8 Expression in Cynomolgus Monkeys

Two anti-CD8A FN3 molecules (CD8S365 and CD8S368) were selected for PET imaging in non-human primates (NHP). The anti-CD8A molecules were radiolabeled with either Zr-89 (Zevacor, Somerset, NJ) or I-124 (CPDC, Hamilton, Canada, and Zevacor, Somerset, NJ). Approximately 1-2 mCi of radiolabeled anti-CD8A molecules was(were) injected into the saphenous vein of a female NHP (cynomolgus macaque), while anesthetized with isoflurane in oxygen. Each animal was scanned in a large-bore microPET Focus 220 PET scanner (Siemens, Knoxville, TN), with the bed moved to accommodate the entire body of the animal (head to lower abdomen). Each scan lasted approximately 1 h, and scans were acquired at 15 min, 2 h, and 24 h after injection. PET images were reconstructed using a 2D maximum likelihood expectation maximization (ML-EM) algorithm, into 3D images of voxel size 1.898×1.898×0.796 mm, dimensions 128×128×475. Blood samples were obtained at multiple time points from the saphenous vein in the opposite leg to the injection, and the blood radioactivity counted in a well counter.

Figure 9:
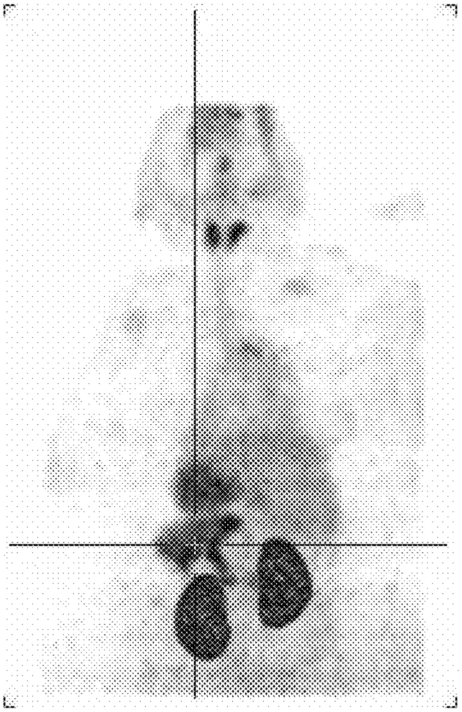
FIG. 9. Representative PET image showing CD8S365-IPEM5 radiolabeled with I-124, taken at 2 h post-injection. The image is a maximum intensity projection (anterior-posterior), with the spleen centered on the cross-hairs. The organs below the spleen are the kidneys, and the image is oriented to show the head at the top. The uptake in the thyroid is evidence of some de-iodination of the protein.

PET images were analyzed using PMOD v3.7 software (PMOD, Zurich, Switzerland). Regions-of-interest were drawn manually around organs such as spleen, kidneys and liver. Counts were converted to units of percent injected dose per gram of tissue (% ID/g), while blood radioactivity was presented as % ID. A representative PET image is shown in FIG. 9.

Figure 10:
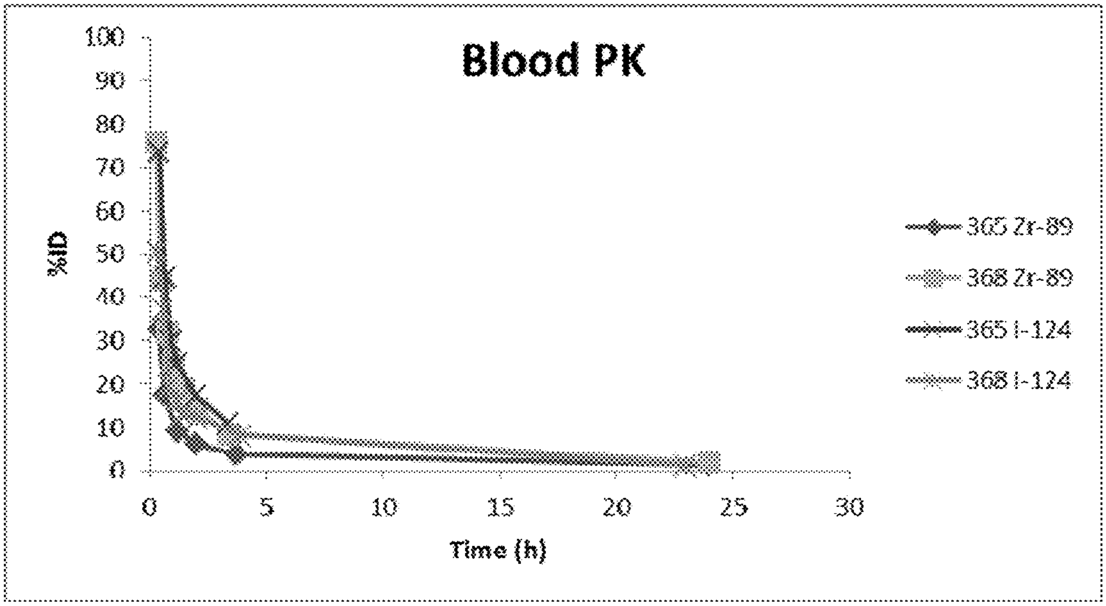
FIG. 10. Time-activity curves for blood radioactivity in non-human primate for each anti-CD8A FN3 domain labeled with either Zr-89 or I-124.

Blood kinetics for each NHP and each anti-CD8A FN3 domain molecule (labeled with either Zr-89 or I-124) are shown in Table 11, and summarized in FIG. 10. For the same animals and anti-CD8A molecules, the organ biodistributions are shown in Table 12 (units are % ID/g), and summarized in FIG. 11. The Zr-89 labeled molecules exhibited residualization of the radioisotope in the excretory organs, which caused a large background signal in the kidneys, potentially obscuring other nearby tissues. This was largely absent from the I-124 labeled molecules. The spleen uptake was very similar between the two different molecules and two different radioisotopes for all time points.

TABLE 11

Blood kinetics for each centyrin, radiolabeled with either Zr-89 or I-124 (entries are % ID).

| Time (h) | 365 Zr-89 | Time (h) | 368 Zr-89 | Time (h) | 365 I-124 | Time (h) | 368 I-124 |
|---|---|---|---|---|---|---|---|
| 0.38 | 32.49 | 0.25 | 75.64 | 0.40 | 73.53 | 0.33 | 50.56 |
| 0.62 | 17.62 | 0.50 | 44.01 | 0.65 | 44.59 | 0.57 | 37.07 |
| 1.18 | 9.03 | 0.75 | 32.06 | 0.92 | 29.79 | 0.87 | 19.33 |
| 2.00 | 6.12 | 1.00 | 24.20 | 1.13 | 24.51 | 1.17 | 16.01 |
| 3.70 | 3.77 | 1.50 | 18.82 | 2.00 | 17.14 | 1.37 | 12.84 |
| 24.00 | 1.36 | 2.00 | 14.22 | 3.33 | 10.92 | 2.07 | 12.18 |
| | | 3.33 | 8.40 | | | 3.88 | 8.20 |
| | | 24.00 | 1.94 | | | 23.03 | 1.24 |

Figure 11A:
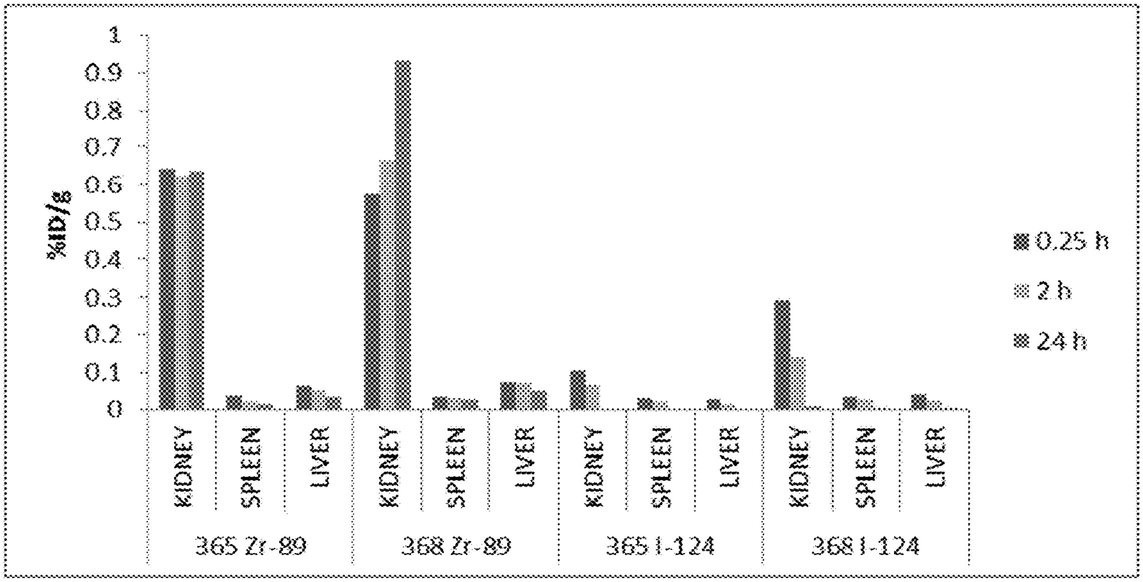
FIGS. 11A and 11B. Time-activity curves for organ radioactivity in NHP for each centyrin labeled with either Zr-89 or I-124.
Figure 11B:
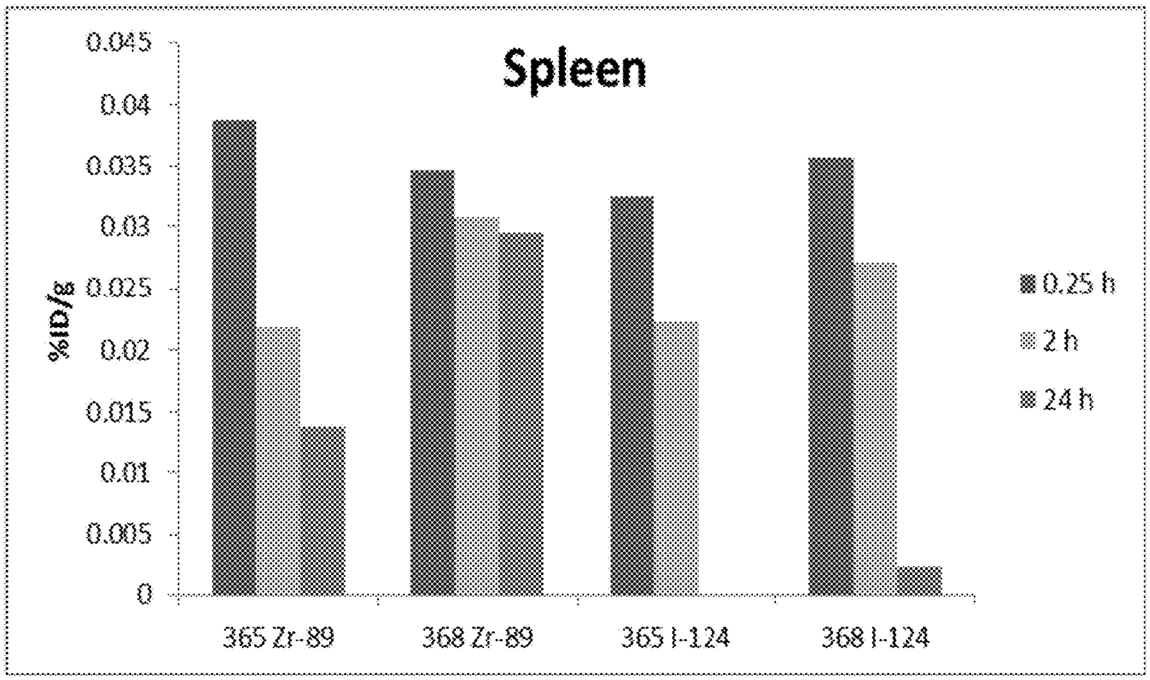

For the same animals and anti-CD8A molecules, the organ biodistributions are shown in Table 12 (units are % ID/g), and summarized in FIG. 11.

TABLE 12

Organ uptake for the different centyrins, labeled with either Zr-89 or I-124 (entries are % ID/g).

| Time (h) | Kidney | Spleen | Liver |
|---|---|---|---|
| 365 Zr-89 | | | |
| 0.25 h | 0.641 | 0.0386 | 0.0620 |
| 2 h | 0.624 | 0.0218 | 0.0513 |
| 24 h | 0.633 | 0.0136 | 0.0354 |
| 368 Zr-89 | | | |
| 0.25 h | 0.575 | 0.0345 | 0.0740 |
| 2 h | 0.664 | 0.0307 | 0.0688 |
| 24 h | 0.931 | 0.0294 | 0.0508 |
| 365 I-124 | | | |
| 0.25h | 0.104 | 0.0324 | 0.0291 |
| 2 h | 0.065 | 0.0222 | 0.0142 |
| 24 h | Not collected due to technical issue | | |
| 368 I-124 | | | |
| 0.25 h | 0.292 | 0.0357 | 0.0439 |
| 2 h | 0.140 | 0.0271 | 0.0241 |
| 24 h | 0.0089 | 0.0022 | 0.0029 |

Example 11: Specificity of Anti-CD8A FN3 Domains in Cynomolgus Monkeys

Figure 12A:
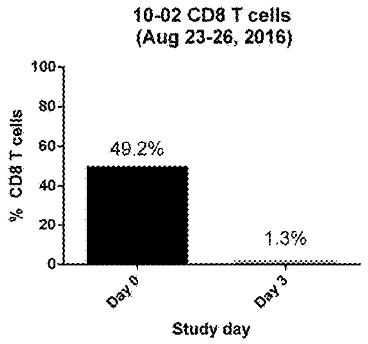
FIG. 12A-12C. Confirmation of CD8 T cell depletion by Day 3 in blood taken from a non-human primate (12A). Also shown are changes in CD4 (12B) and CD3 T cells (12C).
Figure 12B:
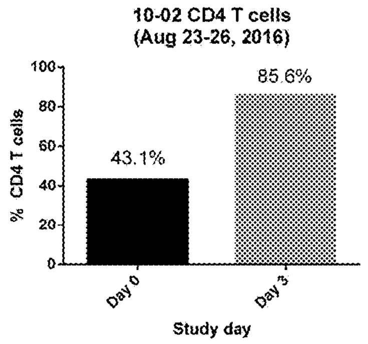
Figure 12C:
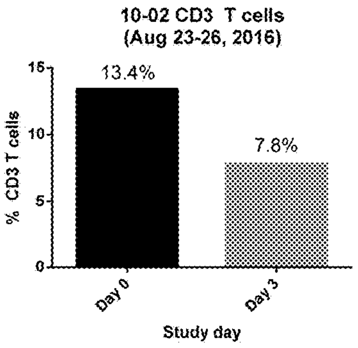

In order to test specificity of the anti-CD8A molecules, the same monkeys were treated with a chimeric CD8-depleting antibody (CM-T807 mouse V/human Fc anti-CD8 antibody) to reduce CD8+ T cells prior to imaging. Animals were administered s.c. with 10 mg/kg CD8 depleting antibody 3 days prior to imaging. CD8 depletion was confirmed by measuring the percentage of CD8 T cells in blood samples taken from each animal before and after depletion (FIG. 12).

Approximately 1-2 mCi of radiolabeled [I-124]CD8S365 anti-CD8 FN3 domain molecule was injected into the saphenous vein of a female NHP (cynomolgus macaque), while anesthetized with isoflurane in oxygen. Each animal was scanned in a large-bore microPET Focus 220 PET scanner (Siemens, Knoxville, TN), with the bed moved to accommodate the entire body of the animal (head to lower abdomen). Each scan lasted approximately 1 h, and scans were acquired at 15 min, 2 h, and 24 h after injection. PET images were reconstructed using a 2D maximum likelihood expectation maximization (ML-EM) algorithm, into 3D images of voxel size 1.898×1.898×0.796 mm, dimensions 128×128×475. Blood samples were obtained at multiple time points from the saphenous vein in the opposite leg to the injection, and the blood radioactivity counted in a well counter.

Figure 13:
FIG. 13. Representative PET image showing the 365 anti-CD8A FN3 domain radiolabeled with I-124, taken at 2 h post-injection in a CD8-depleted animal. The image is a maximum intensity projection (anterior-posterior). This is to be compared against the non-depleted animal in FIG. 9, where the spleen is clearly visible above the kidney.

PET images were analyzed using PMOD v3.7 software (PMOD, Zurich, Switzerland). Regions-of-interest were drawn manually around organs such as spleen, kidneys and liver. Counts were converted to units of percent injected dose per gram of tissue (% ID/g), while blood radioactivity was presented as % ID. A representative PET image is shown in FIG. 13 for a depleted animal, showing a complete absence of the spleen signal seen in the non-depleted animal in FIG. 9.

Figure 14:
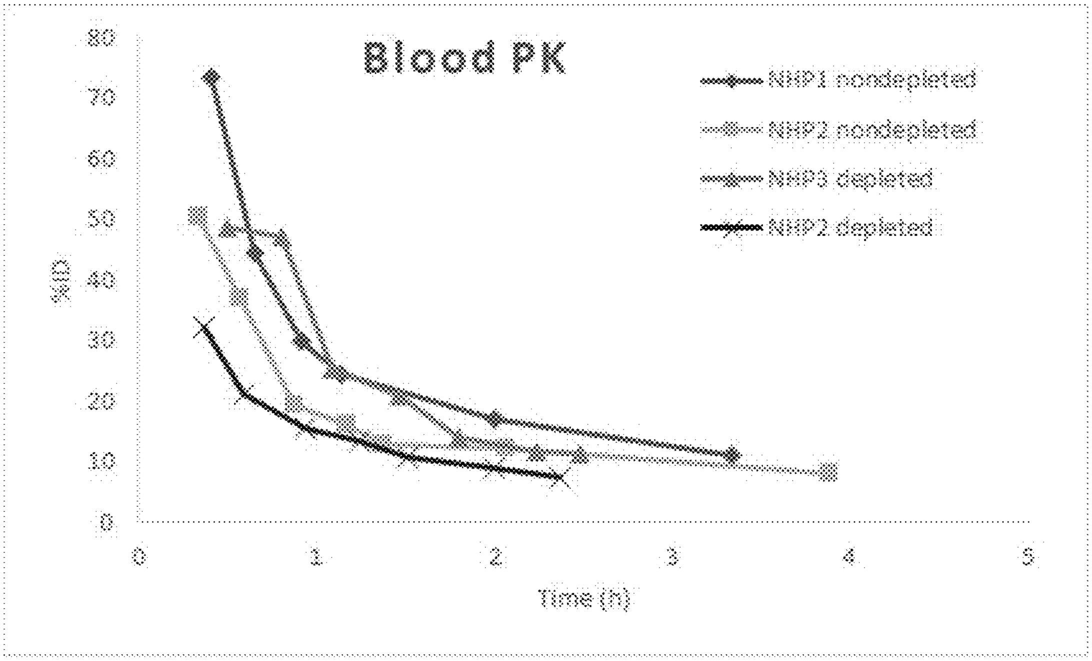
FIG. 14. Time-activity curves for blood radioactivity in cynomolgus monkeys for both depleted and non-depleted animals after administration of [124I]-IPEM CD8S365.
Figure 15A:
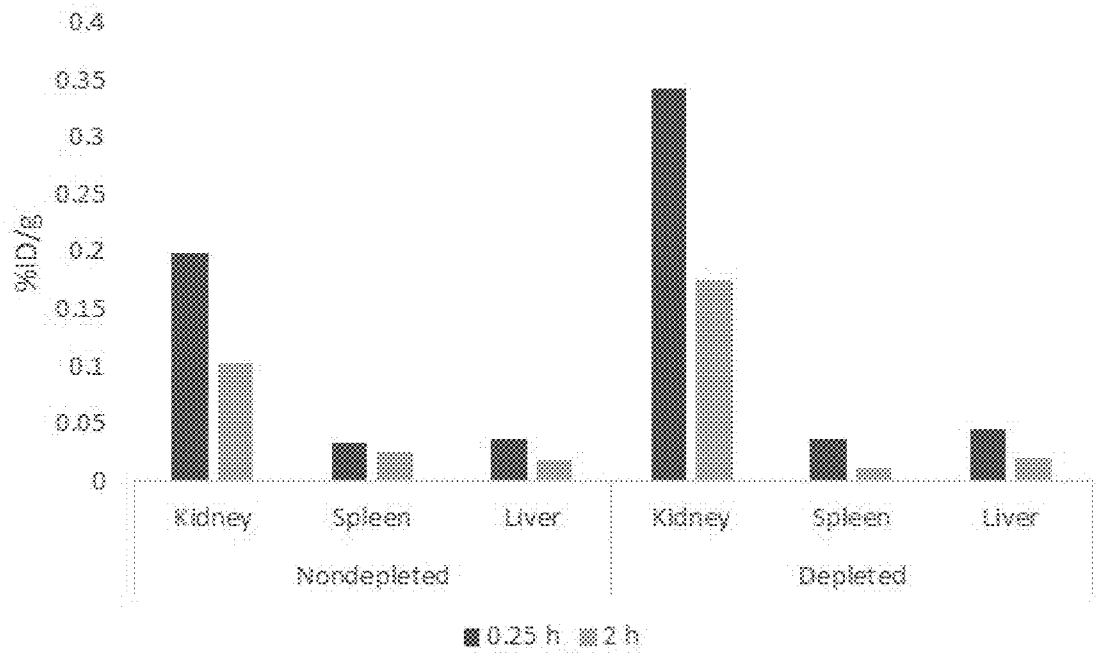
FIGS. 15A and 15B. Time-activity curves for organ radioactivity in cynomolgus monkeys for both depleted and non-depleted animals. 15A includes kidneys, liver and spleen, while 15B is focused on the spleen.
Figure 15B:
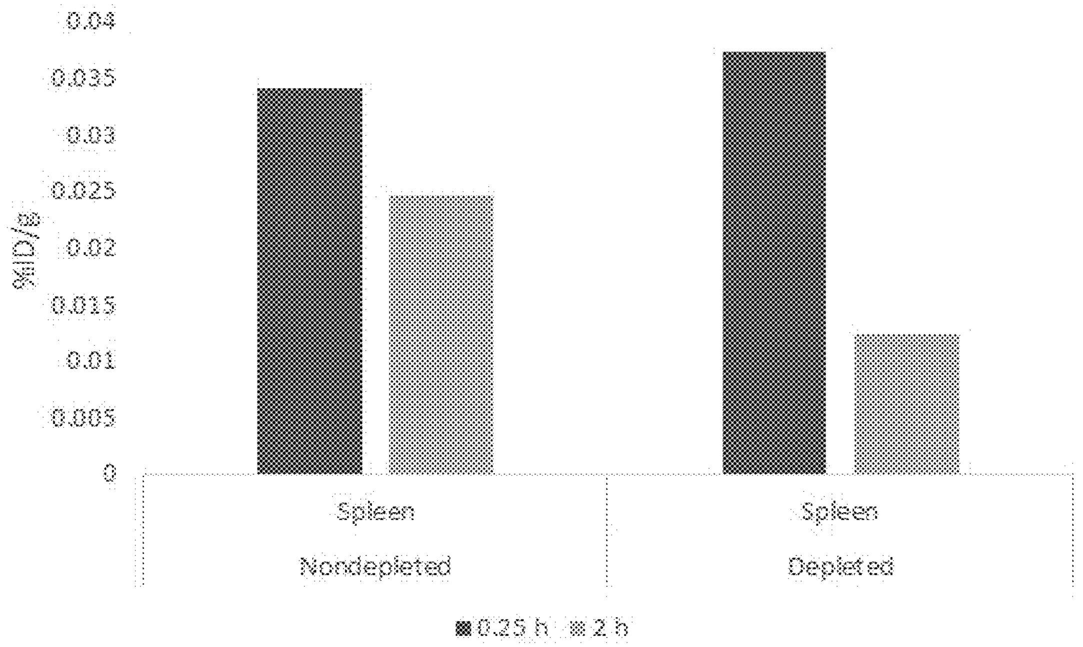

Blood kinetics for each NHP, both depleted and non-depleted, are shown in FIG. 14, while the organ uptakes are shown in FIG. 15. There is little difference in blood kinetics between the depleted and non-depleted animals. Spleen uptake at the earliest time point are similar between depleted and non-depleted, since this is dominated by blood flow. However, at later time points (2 h) the spleen uptake in the depleted animals is less than half that seen in the non-depleted animals, and is essentially at background levels, demonstrating CD8A specificity of the radiolabeled centyrin.

Example 12: Sensitivity and Specificity of PET Imaging in CD8 Over-Expressing Tumors In order to determine the lowest number of cells that can be detected with the anti-CD8A FN3 domain molecules and PET, a study was performed in mice using different numbers of CD8 overexpressing cells. Forty 4-5-week-old female NOD-scid IL2r$\gamma^{null}$ (NSG) mice (JAX Laboratory) were used, and acclimated for 7-10 days. Mice were group housed in IVC-cages under a 12-h light:dark cycle (lights on at 06:30 h) at a temperature of 19 to 22° C. Mice were fed a standard autoclaved laboratory chow and water ad libitum. Mice were ear-tagged and tails were tattooed 5-7 days prior to the start of the study to identify each animal.

HEK-293 parental and HEK-293-luc CD8+ over-expressing cell lines were maintained as 2D-cultures. Mice where implanted subcutaneously with a total of $10^6$ tumor cells in a 1:1 medium to cultrex mix containing varying ratios of HEK-293-Luc CD8+ expressing cells and HEK-293 parental cells. Once tumors were palpable, approximately 10-14 days and 200-300 $mm^3$ in size, the human CD8+ cells were visualized using [I-124]CD8-S365.

Luciferase expression of HEK-293-Luc CD8+ cells was quantified in vivo using bioluminescence imaging in an IVIS Spectrum optical imager (Perkin Elmer). Dynamic optical imaging was performed immediately after injection of 150 mg/kg D-luciferin to identify the peak light emission.

Approximately 0.2-0.5 mCi of radiolabeled anti-CD8A FN3 domain molecules was injected into the tail vein while anesthetized with isoflurane in oxygen. Each animal was scanned in an Inveon microPET-CT scanner (Siemens, Knoxville, TN) for 20 min static scan. Scans were acquired at 2-3 h post tracer injection. PET images were reconstructed using a 2D maximum likelihood expectation maximization (ML-EM) algorithm, into 3D images of voxel size 0.776×0.776×0.796 mm, dimensions 128×128×159.

Figure 16:
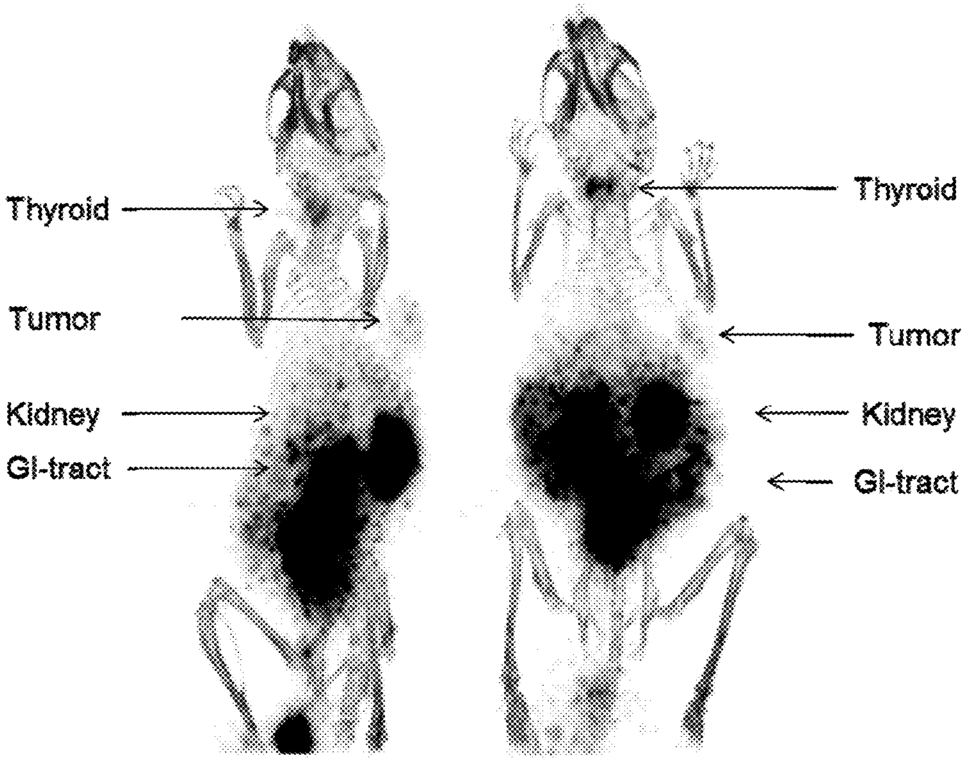
FIG. 16. Representative PET image of a two idenitally treated mice showing the CD8S365-IPEM radiolabeled with I-124, taken at 3 h post-injection. The image is a 3D maximum intensity projection, overlaid on a CT scan. Tumor (formed from HEK-293-luc transfected to over-express huCD8+) and other organs are indicated by arrows. The uptake in the thyroid is evidence of some de-iodination of the protein.

PET images were analyzed using PMOD v3.7 software (PMOD, Zurich, Switzerland). Regions-of-interest were drawn manually around the tumor and other organs such as spleen, kidneys and liver. Counts were converted to units of percent injected dose per gram of tissue (% ID/g). A representative PET image is shown in FIG. 16. Luciferase expression was quantified by drawing regions-of-interest in Living Image v4.4 software (Perkin Elmer). Light emission was measured in units of photons/sec/$cm^2$/steradian.

Figure 17:
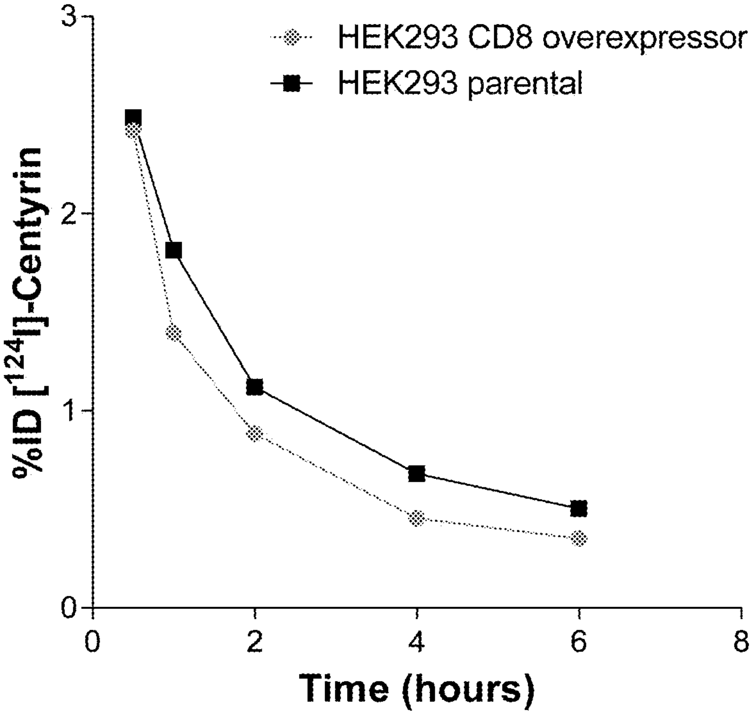
FIG. 17. Time-activity curve for blood radioactivity in mice bearing either HEK-293-luc CD8+ or HEK-293 parental tumors.
Figure 18:
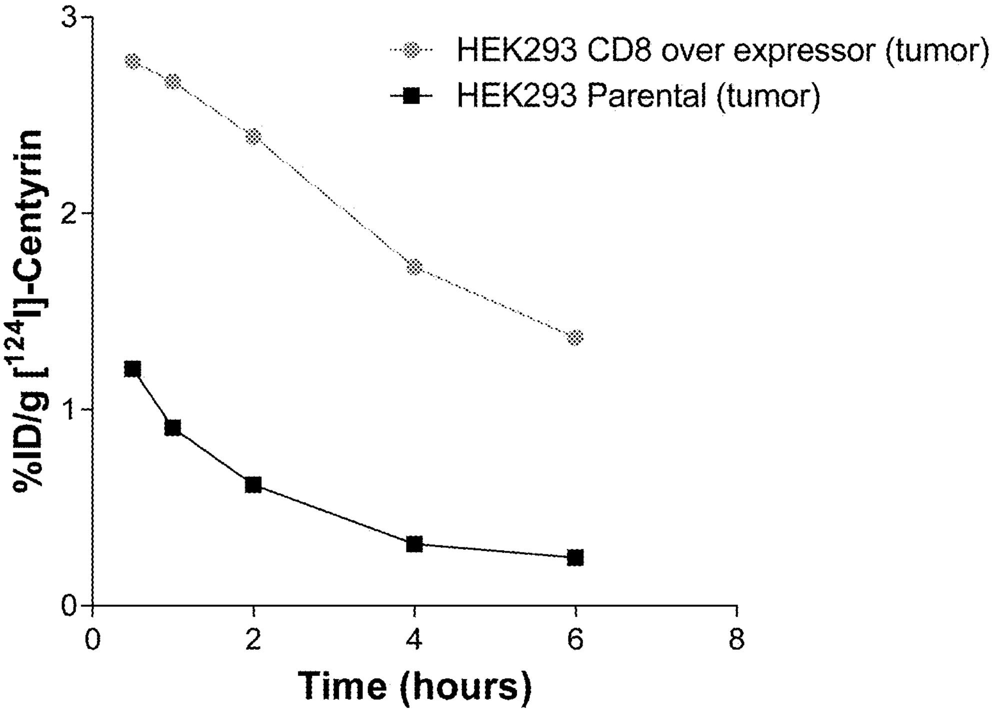
FIG. 18. Time-activity curve for tumor radioactivity in mice bearing either HEK-293-luc CD8+ or HEK-293 parental tumors.
Figure 19:
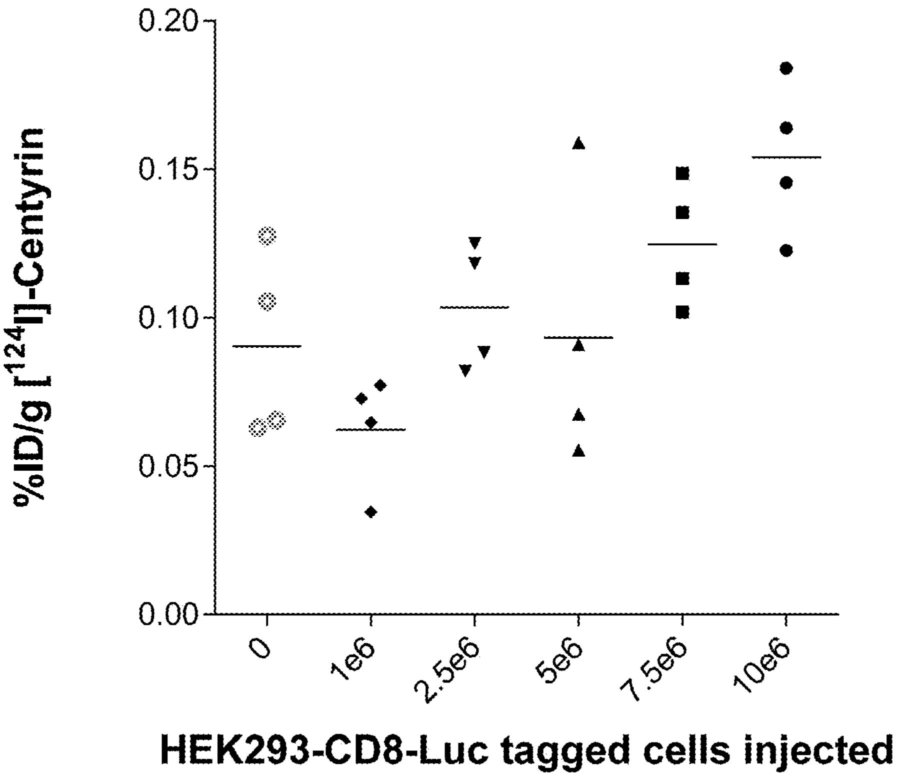
FIG. 19. Uptake of the I-124 labeled CD8S365 in the HEK293 CD8 overexpressing cells, as a function of the number of implanted cells.

Time-activity curves of radiolabeled anti-CD8A FN3 domain molecules in the blood and tumor for both CD8+ HEK293 cells and parental cells are shown in FIG. 17 and FIG. 18. There is a significant increase in anti-CD8A FN3-binding in the CD8-expressing cells compared to the parentals, while the blood activity is the same for both. Uptake of the anti-CD8A FN3 by the CD8+ HEK293 cells is shown in FIG. 19, as a function of number of implanted cells. Based on these data, it is estimated that the lowest level of detection is approximately $7.5\times10^6$ cells.

SEQUENCE LISTING

SEQ ID No. 1 = Original Tencon Sequence
LPAPKNLVVSEVTEDSLRLSWTAPDAAFDSFLIQYQESEKVGEAINLTVP

GSERSYDLTGLKPGTEYTVSIYGVKGGHRSNPLSAEFTT

SEQ ID No. 2 = TCL1 library
LPAPKNLVVSEVTEDSLRLSWTAPDAAFDSFLIQYQESEKVGEAINLTVP

GSERSYDLTGLKPGTEYTVSIYGV$(X)_{7-12}$PLSAEFTT;

wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted SEQ ID No. 3 = TCL2 library
LPAPKNLVVSEVTEDSLRLSW$X_1X_2X_3X_4X_5X_6X_7X_8$SFLIQYQESEKVG

EAINLTVPGSERSYDLTGLKPGTEYTVSIYGV$X_9X_{10}X_{11}X_{12}X_{13}$S$X_{14}$ $X_{15}$LSAEFTT;

wherein
$X_1$ is Ala, Arg, Asn, Asp, Glu, Gln, Gly, His, Ile, Leu, Lys, Phe, Pro, Ser, Thr, Trp, Tyr or Val;
$X_2$ is Ala, Arg, Asn, Asp, Glu, Gln, Gly, His, Ile, Leu, Lys, Phe, Pro, Ser, Thr, Trp, Tyr or Val;
$X_3$ Ala, Arg, Asn, Asp, Glu, Gln, Gly, His, Ile, Leu, Lys, Phe, Pro, Ser, Thr, Trp, Tyr or Val;
$X_4$ is Ala, Arg, Asn, Asp, Glu, Gln, Gly, His, Ile, Leu, Lys, Phe, Pro, Ser, Thr, Trp, Tyr or Val;
$X_5$ is Ala, Arg, Asn, Asp, Glu, Gln, Gly, His, Ile, Leu, Lys, Phe, Pro, Ser, Thr, Trp, Tyr or Val;
$X_6$ is Ala, Arg, Asn, Asp, Glu, Gln, Gly, His, Ile, Leu, Lys, Phe, Pro, Ser, Thr, Trp, Tyr or Val;
$X_7$ is Phe, Ile, Leu, Val or Tyr;
$X_8$ is Asp, Glu or Thr;
$X_9$ is Ala, Arg, Asn, Asp, Glu, Gln, Gly, His, Ile, Leu, Lys, Phe, Pro, Ser, Thr, Trp, Tyr or Val;
$X_{10}$ is Ala, Arg, Asn, Asp, Glu, Gln, Gly, His, Ile, Leu, Lys, Phe, Pro, Ser, Thr, Trp, Tyr or Val;
$X_{11}$ is Ala, Arg, Asn, Asp, Glu, Gln, Gly, His, Ile, Leu, Lys, Phe, Pro, Ser, Thr, Trp, Tyr or Val;
$X_{12}$ is Ala, Arg, Asn, Asp, Glu, Gln, Gly, His, Ile, Leu, Lys, Phe, Pro, Ser, Thr, Trp, Tyr or Val;
$X_{13}$ is Ala, Arg, Asn, Asp, Glu, Gln, Gly, His, Ile, Leu, Lys, Phe, Pro, Ser, Thr, Trp, Tyr or Val;
$X_{14}$ is Ala, Arg, Asn, Asp, Glu, Gln, Gly, His, Ile, Leu, Lys, Phe, Pro, Ser, Thr, Trp, Tyr or Val;
and
$X_{15}$ is Ala, Arg, Asn, Asp, Glu, Gln, Gly, His, Ile, Leu, Lys, Phe, Pro, Ser, Thr, Trp, Tyr or Val.

SEQ ID No. 4 = Stabilized Tencon (Tencon 27)
LPAPKNLVVSRVTEDSARLSWTAPDAAFDSFLIQYQESEKVGEAIVLTVP

GSERSYDLTGLKPGTEYTVSIYGVKGGHRSNPLSAIFTT

SEQ ID No. 5 = TCL7 (FG and BC loops)
LPAPKNLVVSRVTEDSARLSW$X_1X_2X_3X_4X_5X_6X_7X_8X_9$FDSFLIQYQES

EKVGEAIVLTVPGSERSYDLTGLKPGTEYTVSIYGV$X_{10}X_{11}X_{12}X_{13}$ $X_{14}X_{15}X_{16}X_{17}X_{18}X_{19}$SNPLSAIFTT;

wherein
$X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ are A, D, E, F, G, H, I, K, L, N, P, Q, R, S, T, V, W or Y; and
$X_7$, $X_8$, $X_9$, $X_{17}$, $X_{18}$ and $X_{19}$, are A, D, E, F, G, H, I, K, L, N, P, Q, R, S, T, V, W, Y or deleted SEQ ID No. 6 = TCL9 (FG loop)
LPAPKNLVVSRVTEDSARLSWTAPDAAFDSFLIQYQESEKVGEAIVLTVP

GSERSYDLTGLKPGTEYTVSIYGV$X_1X_2X_3X_4X_5X_6X_7X_8X_9X_{10}X_{11}$ $X_{12}$SNPLSAIFTT;

wherein
$X_1$, $X_2$, $X_3$, $X_4$, $X_5$, $X_6$ and $X_7$, is A, D, E, F, G, H, I, K, L, N, P, Q, R, S, T, V, W or Y; and
$X_8$, $X_9$, $X_{10}$, $X_{11}$ and $X_{12}$ is A, D, E, F, G, H, I, K, L, N, P, Q, R, S, T, V, W, Y or deleted.

SEQ ID No. 7 = TCL14 library
LPAPKNLVVSRVTEDSARLSWTAPDAAFDSF$X_1$I$X_2$Y$X_3$E$X_4X_5X_6X_7$GE

AIVLTVPGSERSYDLTGLKPGTEY$X_8$V$X_9$I$X_{10}$GVKGG$X_{11}X_{12}$S$X_{13}$PL

SAIFTT;

wherein
$X_1$, $X_2$, $X_3$, $X_4$, $X_5$, $X_6$, $X_{10}$, $X_{11}$, $X_{12}$ and $X_{13}$ are A, D, E, F, G, H, I, K, L, N, P, Q, R, S, T, V, W, Y, or M.

SEQ ID No. 8 = TCL24 Library
TCL24 Library
(SEQ ID NO: 8)
LPAPKNLVVSRVTEDSARLSWTAPDAAFDSF$X_1$I$X_2$Y$X_3$E$X_4X_5X_6X_7$GE

AI$X_8$L$X_9$VPGSERSYDLTGLKPGTEY$X_{10}$V$X_{11}$I$X_{12}$GVKGG$X_{13}X_{14}$S $X_{15}$PL$X_{16}$A$X_{17}$FTT;

wherein
$X_1$, $X_2$, $X_3$, $X_4$, $X_5$, $X_6$, $X_{10}$, $X_{11}$, $X_{12}$ and $X_{13}$ are A, D, E, F, G, H, I, K, L, N, P, Q, R, S, T, V or W.

SEQ ID No. 9 = Sloning-FOR
GTGACACGGCGGTTAGAAC

SEQ ID No. 10 = Sloning-REV
GCCTTTGGGAAGCTTCTAAG

SEQ ID No. 11 = POP2250
CGGCGGTTAGAACGCGGCTACAATTAATAC

SEQ ID No. 12 = DigLigRev
CATGATTACGCCAAGCTCAGAA

SEQ ID No. 13 = BC9
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTGAAGTTACCGAAGACTCTCTGCGTCTGTCTTGGNNN

NNNNNNNNNNNNNNNNNNNNNNNNNTTYGACTCTTTCCTGATCCAGTACCA

GGAATCTGAAAAAGTTGGTGAAGCGATCAACCTGACCGTTCCGGGTTCTG

AACGTTCTTACGACCTGACCGGTCTGAAACCGGGTACCGAATACACCGTT

TCTATCTACGGTGTTCTTAGAAGCTTCCCAAAGGC

SEQ ID No. 14 = BC8
GTGACACGGCGGTTAGAACGCGGCTACAATTAATACATAACCCCATCCCC

CTGTTGACAATTAATCATCGGCTCGTATAATGTGTGGAATTGTGAGCGGA

-continued

TAACAATTTCACACAGGAAACAGGATCTACCATGCTGCCGGCGCCGAAAA

ACCTGGTTGTTTCTGAAGTTACCGAAGACTCTCTGCGTCTGTCTTGGNNN

NNNNNNNNNNNNNNNNNNNNNTTYGACTCTTTCCTGATCCAGTACCAGGA

ATCTGAAAAAGTTGGTGAAGCGATCAACCTGACCGTTCCGGGTTCTGAAC

GTTCTTACGACCTGACCGGTCTGAAACCGGGTACCGAATACACCGTTTCT

ATCTACGGTGTTCTTAGAAGCTTCCCAAAGGC

SEQ ID No. 15 = BC7
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTGAAGTTACCGAAGACTCTCTGCGTCTGTCTTGGNNN

NNNNNNNNNNNNNNNNNNTTYGACTCTTTCCTGATCCAGTACCAGGAATC

TGAAAAAGTTGGTGAAGCGATCAACCTGACCGTTCCGGGTTCTGAACGTT

CTTACGACCTGACCGGTCTGAAACCGGGTACCGAATACACCGTTTCTATC

TACGGTGTTCTTAGAAGCTTCCCAAAGGC

SEQ ID No. 16 = BC6
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTGAAGTTACCGAAGACTCTCTGCGTCTGTCTTGGNNN

NNNNNNNNNNNNNNNTTYGACTCTTTCCTGATCCAGTACCAGGAATCTGA

AAAAGTTGGTGAAGCGATCAACCTGACCGTTCCGGGTTCTGAACGTTCTT

ACGACCTGACCGGTCTGAAACCGGGTACCGAATACACCGTTTCTATCTAC

GGTGTTCTTAGAAGCTTCCCAAAGGC

SEQ ID No. 17 = 130mer-L17A
CGGCGGTTAGAACGCGGCTACAATTAATACATAACCCCATCCCCCTGTTG

ACAATTAATCATCGGCTCGTATAATGTGTGGAATTGTGAGCGGATAACAA

TTTCACACAGGAAACAGGATCTACCATGCTG

SEQ ID No. 18 = POP222ext
CGG CGG TTA GAA CGC GGC TAC AAT TAA TAC

SEQ ID No. 19 = LS1114
CCA AGA CAG ACG GGC AGA GTC TTC GGT AAC GCG AGA

AAC AAC CAG GTT TTT CGG CGC CGG CAG CAT GGT AGA

TCC TGT TTC

SEQ ID No. 20 = LS1115
CCG AAG ACT CTG CCC GTC TGT CTT GG

SEQ ID No. 21 = LS1117
CAG TGG TCT CAC GGA TTC CTG GTA CTG GAT CAG GAA

AGA GTC GAA

SEQ ID No. 22 = SDG10
CATGCGGTCTCTTCCGAAAAAGTTGGTGAAGCGATCGTCCTGACCGTTCC

GGGT

SEQ ID No. 23 = SDG24
GGTGGTGAAGATCGCAGACAGCGGGTTAG

SEQ ID No. 24 = POP2222
CGGCGGTTAGAACGCGGCTAC

-continued

SEQ ID No. 25 = SDG28
AAGATCAGTTGCGGCCGCTAGACTAGAACCGCTGCCACCGCCGGTGGTGA

AGATCGCAGAC

SEQ ID No. 26 = FG12
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTCGCGTTACCGAAGACTCTGCGCGTCTGTCTTGGACC

GCGCCGGACGCGGCGTTCGACTCTTTCCTGATCCAGTACCAGGAATCTGA

AAAAGTTGGTGAAGCGATCGTGCTGACCGTTCCGGGTTCTGAACGTTCTT

ACGACCTGACCGGTCTGAAACCGGGTACCGAATACACCGTTTCTATCTAC

GGTGTTNNNNNNNNNNNNNNNNNNNNNNNNNNNNNNNNNNNNTCTAACCC

GCTGTCTGCGATCTTCACCACCGGCGGTCACCATCACCATCACCATGGCA

GCGGTTCTAGTCTAGCGGCCGCAACTGATCTTGGC

SEQ ID No. 27 = FG11
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTCGCGTTACCGAAGACTCTGCGCGTCTGTCTTGGACC

GCGCCGGACGCGGCGTTCGACTCTTTCCTGATCCAGTACCAGGAATCTGA

AAAAGTTGGTGAAGCGATCGTGCTGACCGTTCCGGGTTCTGAACGTTCTT

ACGACCTGACCGGTCTGAAACCGGGTACCGAATACACCGTTTCTATCTAC

GGTGTTNNNNNNNNNNNNNNNNNNNNNNNNNNNNNNNNNTCTAACCCGCT

GTCTGCGATCTTCACCACCGGCGGTCACCATCACCATCACCATGGCAGCG

GTTCTAGTCTAGCGGCCGCAACTGATCTTGGC

SEQ ID No. 28 = FG10
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTCGCGTTACCGAAGACTCTGCGCGTCTGTCTTGGACC

GCGCCGGACGCGGCGTTCGACTCTTTCCTGATCCAGTACCAGGAATCTGA

AAAAGTTGGTGAAGCGATCGTGCTGACCGTTCCGGGTTCTGAACGTTCTT

ACGACCTGACCGGTCTGAAACCGGGTACCGAATACACCGTTTCTATCTAC

GGTGTTNNNNNNNNNNNNNNNNNNNNNNNNNNNNNNTCTAACCCGCTGTC

TGCGATCTTCACCACCGGCGGTCACCATCACCATCACCATGGCAGCGGTT

CTAGTCTAGCGGCCGCAACTGATCTTGGC

SEQ ID No. 29 = FG9
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTCGCGTTACCGAAGACTCTGCGCGTCTGTCTTGGACC

GCGCCGGACGCGGCGTTCGACTCTTTCCTGATCCAGTACCAGGAATCTGA

AAAAGTTGGTGAAGCGATCGTGCTGACCGTTCCGGGTTCTGAACGTTCTT

-continued

ACGACCTGACCGGTCTGAAACCGGGTACCGAATACACCGTTTCTATCTAC

GGTGTTNNNNNNNNNNNNNNNNNNNNNNNNNNNNNTCTAACCCGCTGTCTGC

GATCTTCACCACCGGCGGTCACCATCACCATCACCATGGCAGCGGTTCTA

GTCTAGCGGCCGCAACTGATCTTGGC

SEQ ID No. 30 = FG8
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTCGCGTTACCGAAGACTCTGCGCGTCTGTCTTGGACC

GCGCCGGACGCGGCGTTCGACTCTTTCCTGATCCAGTACCAGGAATCTGA

AAAAGTTGGTGAAGCGATCGTGCTGACCGTTCCGGGTTCTGAACGTTCTT

ACGACCTGACCGGTCTGAAACCGGGTACCGAATACACCGTTTCTATCTAC

GGTGTTNNNNNNNNNNNNNNNNNNNNNNNNNNTCTAACCCGCTGTCTGCGAT

CTTCACCACCGGCGGTCACCATCACCATCACCATGGCAGCGGTTCTAGTC

TAGCGGCCGCAACTGATCTTGGC

SEQ ID No. 31 = FG7
GTGACACGGCGGTTAGAACGCGGCTACAATTAATACATAACCCCATCCCC

CTGTTGACAATTAATCATCGGCTCGTATAATGTGTGGAATTGTGAGCGGA

TAACAATTTCACACAGGAAACAGGATCTACCATGCTGCCGGCGCCGAAAA

ACCTGGTTGTTTCTCGCGTTACCGAAGACTCTGCGCGTCTGTCTTGGACC

GCGCCGGACGCGGCGTTCGACTCTTTCCTGATCCAGTACCAGGAATCTGA

AAAAGTTGGTGAAGCGATCGTGCTGACCGTTCCGGGTTCTGAACGTTCTT

ACGACCTGACCGGTCTGAAACCGGGTACCGAATACACCGTTTCTATCTAC

GGTGTTNNNNNNNNNNNNNNNNNNNNNNNTCTAACCCGCTGTCTGCGATCTT

CACCACCGGCGGTCACCATCACCATCACCATGGCAGCGGTTCTAGTCTAG

CGGCCGCAACTGATCTTGGC

SEQ ID NO: 32 FG loop of Tencon
KGGHRSN

SEQ ID No. 33 = Tcon 6
AAGAAGGAGAACCGGTATGCTGCCGGCGCCGAAAAAC

-continued

SEQ ID No. 34 = Tcon5E86Ishort
GAG CCG CCG CCA CCG GTT TAA TGG TGA TGG TGA TGG

TGA CCA CCG GTG GTG AAG ATC GCA GAC AG

>SEQ ID No. 35: CD8W7
SQFRVSPLDRTWNLGETVELKCQVLLSNPTSGCSWLFQPRGAAASPTFLL

YLSQNKPKAAEGLDTQRFSGKRLGDTFVLTLSDFRRENEGYYFCSALSNS

IMYFSHFVPVFLPAKPTTTPAPRPPTPAPTIASQPLSLRPEACRPAGSGS

GSDYKDDDDKDKTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTK

NQVSLTCLVKGFYPSDIAVEWESNGQPENNYKTTPPVLDSDGSFFLYSKL

TVDKSRWQQGNVFSCSVMHEALHNHYTQKSLSLSPGK

>SEQ ID No 36: CD8W13
SQFRVSPLDRTWNLGETVELKCQVLLSNPTSGCSWLFQPRGAAASPTFLL

YLSQNKPKAAEGLDTQRFSGKRLGDTFVLTLSDFRRENEGYYFCSALSNS

IMYFSHFVPVFLPAKPTTTPAPRPPTPAPTIASQPLSLRPEACRPAAGGA

VHTRGLDFACDGGGGSDYKDDDDKGGGGSHHHHHHDKTHTCPPCPAPELL

GGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNH

YTQKSLSLSPGK

>SEQ ID No. 37: mIgGK signal peptide
Metdtlllwvlllwvpgstg

>SEQ ID No. 38: Human Fc
Dkthtcppcpapellggpsvflfppkpkdtlmisrtpevtcvvvdvshed pevkfnwyvdgvevhnaktkpreeqynstyrvvsvltvlhqdwlngkeyk ckvsnkalpapiektiskakgqprepqvytlppsrdeltknqvsltclvk gfypsdiavewesngqpennykttppvldsdgsfflyskltvdksrwqqg nvfscsvmhealhnhytqkslslspgk >SEQ ID No. 39: linker sequence
Ggggsdykddddkggggshhhhhh

| Clone ID | SEQ ID No | Amino Acid Sequence |
|---|---|---|
| P282AR9P1356_A10 | 40 | LPAPKNLVVSRVTEDSARLSWHTATNSFDSFLIQYQESEKVGEAIVLTVPGSERSYDLTGLKPGTEYTVSIYGVDVDYNPTGRPVSSNPLSAIFTT |
| P282AR9P1356_A4 | 41 | LPAPKNLVVSRVTEDSARLSWVKRPNSFDSFLIQYQESEKVGEAIVLTVPGSERSYDLTGLKPGTEYTVSIYGVDVVDYEGRPRWSNPLSAIFTT |
| P282AR9P1356_A6 | 42 | LPAPKNLVVSRVTEDSARLSWSKTDSSFDSFLIQYQESEKVGEAIVLTVPGSERSYDLTGLKPGTEYTVSIYGVDVVYIEGNPVFSNPLSAIFTT |
| P282AR9P1356_B9 | 43 | LPAPKNLVVSRVTEDSARLSWPEGDRPFFDSFLIQYQESEKVGEAIVLTVPGSERSYDLTGLKPGTEYTVSIYGVDVKWEGNRPVASNPLSAIFTT |

-continued

| | | |
|---|---|---|
| P282AR9P1356_D3 | 44 | LPAPKNLVVSRVTEDSARLSWTRHETSFDSFLIQYRESEKVGEAIVLTVPGSERSYDLTGLKPGTEYTVSIYGVVVEYDAAGNPKYSNPLSAIFTT |
| P282AR9P1356_H1 | 45 | LPAPKNLVVSRVTEDSARLSWIPNPSSFDSFLIQYQESEKVGEAIVLTVPGSERSYDLTGLKPGTEYTVSIYGVDVVFDPVGFPSHSNPLSAIFTT |
| P282AR9P1356_H6 | 46 | LPAPKNLVVSRVTEDSARLSWRKRANSFDSFLIQYQESEKVGEAIVLTVPGSERSYDLTGLKPGTEYTVSIYGVHVEYDQHGRPRWSNPLSAIFTT |
| P282BR9P1357_A9 | 47 | LPAPKNLVVSRVTEDSARLSWKANRTTDLHFDSFLIQYQESEKVGEAIVLTVPGSERSYDLTGLKPGTEYTVSIYGVDVQYDGQQPLYSNPLSAIFTT |
| P282BR9P1357_B2 | 48 | LPAPKNLVVSRVTEDSARLSWNPSEDPQRFDSFLIQYQESEKVGEAIVLTVPGSERSYDLTGLKPGTEYTVSIYGVDVKWEGNRPVASNPLSAIFTT |
| P282BR9P1357_C10 | 49 | LPAPKNLVVSRVTEDSARLSWWSNDNRPIFDSFLIQYQESEKVGEAIVLTVPGSERSYDLTGLKPGTEYTVSIYGVDVKWEGNRPVASNPLSAIFTT |
| P282BR9P1357_C4 | 50 | LPAPNNLVVSRVTEDSARLSWPFVSQNKPHFDSFLIQYQESEKVGEAIVLTVPGSERSYDLTGLKPGTEYTVSIYGVDVKWEGNRPVASNPLSAIFTT |
| P282BR9P1357_D12 | 51 | LPAPKNLVVSRVTEDSARLSWGQYITAFSFDSFLIQYQESEKVGEAIVLTVPGSERSYDLTGLKPGTEYTVSIYGVDVAWFQGKPTWSNPLSAIFTT |
| P282BR9P1357_D2 | 52 | LPAPKNLVVSRVTEDSARLSWIKDGHPRHFDSFLIQYQESEKVGEAIVLTVPGSERSYDLTGLKPGTEYTVSIYGVDVVYDRGQLISSNPLSAIFTT |
| P282BR9P1357_E5 | 53 | LPAPKNLVVSRVTEDSARLSWWPRKYQRPFDSFLIQYQESEKVGEAIVLTVPGSERSYDLTGLKPGTEYTVSIYGVDIEWIGNRPIASNPLSAIFTT |
| P282BR9P1357_G9 | 54 | LPAPKNLVVSRVTEDSARLSWPIASQIHSPFDSFLIQYQESEKVGEAIVLTVPGSERSYDLTGLKPGTEYTVSIYGVDVKYDIDSRPISSNPLSAIFTT |
| P282BR9P1357_H3 | 55 | LPAPKNLVVSRVTEDSARLSWKKREYQDPGFDSFLIQYQESEKVGEAIVLTVPGSERSYDLTGLKPGTEYTVSIYGVDVKWEGNRPVASNPLSAIFTT |
| P282CR9P1358_C2 | 56 | LPAPKNLVVSRVTEDSARLSWTAPDAAFDSFKIAYPEWPSNGEAIVLTVPGSERSYDLTGLKPGTEYAVFIWGVKGGAFSNPLSAIFTT |
| P282CR9P1358_C5 | 57 | LPAPKNLVVSRVTEDSARLSWTAPDAAFDSFLIAYPEWPDSGEAIVLTVPGSERSYDLTGLKPGTEYAVFIWGVKGGPLSHPLSAIFTT |
| P282CR9P1358_D10 | 58 | LPAPKNLVVSRVTEDSARLSWTAPDAAFDSFLISYPEYPPPGEAIVLTVPGSERSYDLTGLKPGTEYFVIIFGVKGGDTSWPLSAIFTT |
| P282CR9P1358_F11 | 59 | LPAPKNLVVSRVTEDSARLSWTAPDAAFDSFLIAYPEWPIFEGEAIVLTVPGSERSYDLTGLKPGTEYFVVIYGVKGGEQSSPLSAIFTT |
| P282CR9P1358_F5 | 60 | LPAPKNLVVSRVTEDSARLSWTAPDAAFDSFWISYPEWPPDGEAIVLTVPGSERSYDLTGLKPGTEYFVIIWGVKGGETSAPLSAIFTT |
| P282DR9P1359_A12 | 61 | LPAPKNLVVSRVTEDSARLSWTAPEAAFDSFQIAYPEWPPPREAIVLTVPGSERSYDLTGLKPGTEYFVVIQGVKGGEISWPLSAIFTT |
| P282DR9P1359_A7 | 62 | LPAPKNLVVSRVTEDSARLSWTAPDAAFDSFRIGYPELEKLGYGEAIVLTVPGSERSYDLTGLKPGTEYWVIIWGVKGGENSWPLSAIFTT |
| P282DR9P1359_A8 | 63 | LPAPKNLVVSRVTEDSARLSWTAPDAAFDSFRIAYPEWPVQGEAIVLTVPGSERSYDLTGLKPGTEYFVIIYGVKGGELSPPLSAIFTT |
| P282DR9P1359_B2 | 64 | LPAPKNLVVSRVTEDSARLSWTAPDAAFDSFWIAYTEWPIPYEEAGQEGEAIVLTVPGSERSYDLTGLKPGTEYWVSIYGVKGGPNSQPLSAIFTT |
| P282DR9P1359_C10 | 65 | LPAPKNLVVSRVTEDSARLSWTAPDAAFDSFAIVYPEWPTDGEAIVLTVPGSERSYDLTGLKPGTEYAVFIWGVKGGNQSWPLSAIFTT |

-continued

| | | |
|---|---|---|
| P282DR9P1359_C11 | 66 | LPAPKNLVVSRVTEDSARLSWTAPDAAFDSFKIAYPEFPPPGEAIVL<br>TVPGSERSYDLTGLKPGTEYYVIIIGVKGGTDSWPLSAIFTT |
| P282DR9P1359_C12 | 67 | LPAPKNLVVSRVTEDSARLSWTAPDAAFDSFYISYPEWPVPGEAIVL<br>TVPGSERSYDLTGLKPGTEYWVVIYGVKGGALSVPLSAIFTT |
| P282DR9P1359_C5 | 68 | LPAPKNLVVSRVTEDSARLSWTAPDAAFDSFWITYPEWPDPGGEAIV<br>LTVPGSERSYDLTGLKPGTEYFVVIYGVKGGEIYSPLSAIFTT |
| P282DR9P1359_D12 | 69 | LPAPKNLVVSRVTEDSARLSWTAPDAAFDSFRIAYPETATWGEAIVL<br>TVPGSERSYDLTGLKPGTEYFVIIYGVKGGFESAPLSAIFTT |
| P282DR9P1359_E11 | 70 | LPAPKNLVVSRVTEDSARLSWTAPDAAFDSFYISYPEWPPVGEAIVL<br>TVPGSERSYDLTGLKPGTEYWVIIYGVKGGAISTPLSAIFTT |
| P282DR9P1359_E2 | 71 | LPAPKNLVVSRVTEDSARLSWTAPDAAFDSFNIFYPEIVTWGEAIVL<br>TVPGSERSYDLTGLKPGTEYWVNIVGVKGGDNSWPLSAIFTT |
| P282DR9P1359_E3 | 72 | LPAPKNLVVSRVTEDSARLSWTAPDAAFDSFAIAYPELPLGGEAIVL<br>TVPGSERSYDLTGLKPGTEYFVIIYGVKGGVESFPLSAIFTT |
| P282DR9P1359_E5 | 73 | LPAPKNLVVSRVTEDSARLSWTAPDAAFDSFAISYPEWPVPGEAIVL<br>TVPGSERSYDLTGLKPGTEYFVIIYGVKGGLYSAPLSAIFTT |
| P282DR9P1359_E6 | 74 | LPAPKNLVVSRVTEDSARLSWTAPDAAFDSFWIAYPEWPVQGEAIVL<br>TVPGSERSYDLTGLKPGTEYFVVIQGVKGGTPSWPLSAIFTT |
| P282DR9P1359_E8 | 75 | LPAPKNLVVSRVTEDSARLSWTAPDAAFDSFQIAYPEWPVIGEAIVL<br>TVPGSERSYDLTGLKPGTEYWVIIQGVKGGYTSWPLSAIFTT |
| P282DR9P1359_F11 | 76 | LPAPKNLVVSRVTEDSARLSWTAPDAAFDSFDIFYPELPIHGEAIVL<br>TVPGSERSYDLTGLKPGTEYWVNITGVKGGDFSWPLSAIFTT |
| P282DR9P1359_F2 | 77 | LPAPKNLVVSRVTEDSARLSWTAPDAAFDSFNIAYPEALHPGYGEAI<br>VLTVPGSERSYDLTGLKPGTEYWVIIGGVKGGQKSWPLSAIFTTGGH<br>HHDHH |
| P282DR9P1359_F3 | 78 | LPAPKNLVVSRVTEDSARLSWTAPDAAFDSFYITYPEWPVQGEAIVL<br>TVPGSERSYDLTGLKPGTEYWVIIYGVKGGTESEPLSAIFTT |
| P282DR9P1359_F5 | 79 | LPAPKNLVVSRVTEDSARLSWTAPDAAFDSFQIAYPEWPPPGEAIVL<br>TVPGSERSYDLTGLKPGTEYFVIIQGVKGGVESWPLSAIFTT |
| P282DR9P1359_F6 | 80 | LPAPKNLVVSRVTEDSARLSWTAPDAAFDSFDIAYPEWPTTGEAIVL<br>TVPGSERSYDLTGLKPGTEYFVVIWGVKGGDHSAPLSAIFTT |
| P282DR9P1359_F7 | 81 | LPAPKNLVVSRVTEDSARLSWTAPDAAFDSFAIAYPEWPPQGEAIVL<br>TVPGSERSYDLTGLKPGTEYFVVIYGVKGGSYSAPLSAIFTT |
| P282DR9P1359_G4 | 82 | LPAPKNLVVSRVTEDSARLSWTAPDAAFDSFEIAYPEWPPPGEAIVL<br>TVPGSERSYDLTGLKPGPEYFVVIQGVKGGDPSFPLSAIFTTGGNHH<br>HHH |
| P282DR9P1359_G7 | 83 | LPAPKNLVVSRVTEDSARLSWTAPDAAFDSFAITYIEKEHIEDGEAI<br>VLTVPGSERSYDLTGLKPGTEYWVPIWGVKGGANSWPLSAIFTT |
| P282DR9P1359_H5 | 84 | LPAPKNLVVSRVTEDSARLSWTAPDAAFDSFNIAYPEALHPGYGEAI<br>VLTVPGSERSYDLTGLKPGTEYFVVIYGVKGGTNSEPLSAIFTT |
| P282ER9P1360_A9 | 85 | LPAPKNLVVSRVTEDSARLSWTAPDAAFDSFGILYYEPVDSGEAITL<br>PIPGSERSYDLTGLKPGTEYWVVITGVKGGAPSTPLGAIFTT |
| P282ER9P1360_C1 | 86 | LPAPKNLVVSRVTEDSARLSWTTPDAAFDSFGILYYEPVDSGEAITL<br>PVPGSERSYDLTGLKPGTEYWVVITGVKGGAPSTPLGAIFTT |
| P282ER9P1360_C4 | 87 | LPAPKNLVVSRVTEDSARLSWTAPDAAFDSFGITYYEPNHGGEAISL<br>SVPGSERSYDPTGLKPGTEYWVVITGVKGGAPSTPLGAIFTT |
| P282ER9P1360_C6 | 88 | LSAPKNLVVSRVTEDSARLSWTAPDAAFDSFGILYYEPVDSGEAITL<br>PIPGSERSYDLTGLKPGTEYWVVITGVKGGAPSTPLGAIFTT |
| P282ER9P1360_C8 | 89 | LPAPKNLVVSRVTEDSARLSWTAPDAAFDSFGILYYEPVDSGEAITL<br>PVPGSERSYDLTGLKPGTEYWVVITGVKGGAPSTPLGTIFTT |
| P282ER9P1360_D11 | 90 | LPAPKNLVVSRVTEDSARLSWTAPDAAFDSFGILYYEPVDSGEAITL<br>PVPGSERSYDLTGLKPGTEYFVIIVGVKGGYPSIPLGAAFTT |

-continued

| | | |
|---|---|---|
| P282ER9P1360_E4 | 91 | LPAPKNLVVSRVTEDSARLSWTAPDAAFDSFGILYYEPVDSGEAITL PVLGSERSYDLTGLKPGTEYWVVITGVKGGAPSTPLGAIFTT |
| P282ER9P1360_F11 | 92 | LPAPKNLVVSRVTEDSARLSWIAPDAAFDSFSIAYVEAELVGEAIQL VVPGSERSYDLTGLKPGTEYWVVILGVKGGNPSNPLGASFTT |
| P282ER9P1360_G10 | 93 | LPAPKNLVVSRVTEDSARLSWTAPDAAFDSFAIWYVEQHPFGEAIPL FVPGSERSYDLTGLKPGTEYTVGIRGVKGGNFSTPLIAHFTT |
| P282ER9P1360_G7 | 94 | LPAPKNLVVSRVTEDSARLSWTAPDAAFDSFGILYYEPVDSGEAITL PVPGSERSYDLTGLKPGTEYWVVITGVKGGAPSTPLGAILTT |
| P282ER9P1360_H10 | 95 | LPAPKNLVVSRVTEDSARLSWTAPDAAFDSFEIYYPEWPFAGEAIGL PVPGSERSYDLTGLKPGTEYFVVIYGVKGGELSEPLTAQFTT |
| P282ER9P1360_H2 | 96 | LPAPKNLVVSRVTEDSARLSWTAPDAAFDSFSIAYVEAELVGEAIQL VVPGSERSYDLTGLKPGTEYWVVILGVKGGNPSNPLGASFTTT |
| P282ER9P1360_H3 | 97 | LPAPKNLVVSRVTEDSARLSWTAPDAAFDSFSIAYVEAELVGEAIQL VVPGSERSYDLTGLKPGTEYWVVILGVKGGNPSNPLGASFTT |
| P282FR9P1361_A3 | 98 | LPAPKNLVVSRVTEDSARLSWTAPDAAFDSFDIWYAEYGYPGEAIVL TVPGSERSYDLTGLKPGTEYDVAIVGVKGGNRSYPLSAIFTT |
| P282FR9P1361_A5 | 99 | LPAPKNLVVSRVTEDSARLSWTAPDAAFDSFGILYYEPVDSGEAITL PVPGSERSYDLTGLKPGTEYWVVITGVKGGAPSTPLGAIFTT |
| P282FR9P1361_C7 | 100 | LPAPKNLVVSRVTEDSARLSWTAPDAAFDSFGIWYHEYGGDGEAIVL TVPGSERSYDLTGLKPGTEYDVAIWGVKGGDVSYPLSAIFTT |
| P282FR9P1361_D3 | 101 | LPAPKNLVVSRVTEDSARLSWTAPDAAFDSFDIWYAEYGYPGEAIVL TVPGSERSYDLTGLNPGTEYDVAISGVKGGPRSYPLSAIFTT |
| P282FR9P1361_E12 | 102 | LPAPKNLVVSRVTEDSARLSWTAPDAAFDSLGITYWESPYAGEAIVL TVPGSERSYDLTGLKPGTEYGVFILGVKGGYPSAPLSAIFTT |
| P282FR9P1361_F1 | 103 | LPAPKNLVVSRVTEDSARLSWTAPDAAFDSFGIWYAEYGYSGEAIVL TVPGSERSYDLTGLKPGTEYDVAIWGVKGGVRSYPLSAIFTT |
| P282FR9P1361_F11 | 104 | LPAPKNLVVSRVTEDSARLSWTAPDAAFDSFGIWYREYGGSGEAIVL TVPGSERSYDLTGLKPGTEYDVAIWGVKGGVRSYPLSAIFTT |
| P282FR9P1361_F2 | 105 | LPAPKNLVVSRVTEDSARLSWTAPDAAFDSFDIWYAEYGYPGEAIVL TVPGSERSYDLTGLKPGTEYDVAISGIKGGPRSYPLSAIFTT |
| P282FR9P1361_F3 | 106 | LPAPKNLVVSRVTEDSARLSWTAPDAAFDSFDIWYAEYGYPGEAIVL TVPGSERSYDLTGLKPGTEYDVAISGAKGGPRSYPLSAIFTT |
| P282FR9P1361_F7 | 107 | LPAPKNLVVSRVTEDSARLSWTAPDAAFDSFPIWYREYATGEAIVLT VPGSERSYDLTGLKPGTEYDVVITGVKGGYPSYPLSAIFTT |
| P282FR9P1361_G9 | 108 | LPAPKNLVVSRVTEDSARLSWTAPDAAFDSFGITYWESPYAGEAIVL TVPGSERSYDLTGLKPGTEYGVFILGVKGGYPSAPLSAIFTT |
| P282FR9P1361_H4 | 109 | LPAPKNLVVSRVTEDSARLSWTAPDAAFDSFGIWYAEYGYSGEAIVL TVPGSERSYDLTGLKPGTEYDVAIYGVKGGSPSYPLSAIFTT |
| P282FR9P1361_H5 | 110 | LPAPKNLVVSRVTEDSARLSWTAPDAAFDSFDIWYAEYGYPGEAIVL TVPGSERSYDLTGLKPGTEYDVAISGVKGGPRSYPLSAIFTT |
| P283AR9P1362_A3 | 111 | LPAPKNLVVSRVTEDSARLSWKRIDSPFDSFLIQYQESEKVGEAIVL TVPGSERSYDLTGLKPGTEYTVSIYGVDVKYDIDSRPISSNPLSAIF TT |
| P283AR9P1362_A4 | 112 | LPAPKNLVVSRVTEDSARLSWIGHDSGFDSFLIQYQESEKVGEAIVL TVPGSERSYDLTGLKPGTEYTVSIYGVDVKYDIDSRPISSNPLSAIF TT |
| P283AR9P1362_B10 | 113 | LPAPKNLVVSRVTEDSARLSWKRRWDSFDSFLIQYQESEKVGEAIVL TVPGSERSYDLTGLKPGTEYTVSIYGVDVEWFNGLPHHSNPLSAIFT T |
| P283AR9P1362_B2 | 114 | LPAPKNLVVSRVTEDSARLSWAKHPNSFDSFLIQYQESEKVGEAIVL TVPGSERSYDLTGLKPGTEYTVSIYGVDVVVNELNNPLFSNPLSAIF TT |

-continued

| | | |
|---|---|---|
| P283AR9P1362_B8 | 115 | LPAPKNLVVSRVTEDSARLSWWTSPLPFDSFLIQYQESEKVGEAIVL TVPGSERSYDLTGLKPGTEYTVSIYGVDVKYDIDSRPISSNPLSAIF TT |
| P283AR9P1362_C12 | 116 | LPAPKNLVVSRVTEDSARLSWAKNLHSFDSFLIQYQESEKVGEAIVL TVPGSERSYDLTGLKPGTEYTVSIYGVDVKYDIDSRPISSNPLSAIF TT |
| P283AR9P1362_C6 | 117 | LPAPKNLVVSRVTEDSARLSWYPSDPPFDSFLIQYQESEKVGEAIVL TVPGSERSYDLTGLKPGTEYTVSIYGVPNYHSRRSYYYSNPLSAIFT T |
| P283AR9P1362_C7 | 118 | LPAPKNLVVSRVTEDSARLSWVKRATSFDSFLIQYQESEKVGEAIVL TVPGSERSYDLTGLKPGTEYTVSIYGVDVRYNEGQPIWSNPLSAIFT T |
| P283AR9P1362_D2 | 119 | LPAPKNLVVSRVTEDSARLSWQRPKSGFFDSFLIQYQESEKVGEAIV LTVPGSERSYDLTGLKPGTEYTVSIYGVDVKYDIDSRPISSNPLSAI FTT |
| P283AR9P1362_D3 | 120 | LPAPKNLVVSRVTEDSARLSWPVESNAFDSFLIQYQESEKVGEAIVL TVPGSERSYDLTGLKPGTEYTVSIYGVDVEYDQHGRPRWSNPLSAIF TT |
| P283AR9P1362_D4 | 121 | LPAPKNLVVSRVTEDSARLSWVREHDSFDSFLIQYQESEKVGEAIVL TVPGSERSYDLTGLKPGTEYTVSIYGVDVKYDIDSRPISSNPLSAIF TT |
| P283AR9P1362_D6 | 122 | LPAPKNLVVSRVTEDSARLSWAKRPGAFDSFLIQYQESEKVGEAIVL TVPGSERSYDLTGLKPGTEYTVSIYGVDVKYDIDSRPISSNPLSAIF TT |
| P283AR9P1362_D7 | 123 | LPAPKNLVVSRVTEDSARLSWVKRATSFDSFLIQYQESEKVGEAIVL TVPGSERSYDLTGLKPGTEYTVSIYGVDVKYDIDSRPISSNPLSAIF TT |
| P283AR9P1362_E9 | 124 | LPAPKNLVVSRVTEDSARLSWVPSPWGFDSFLIQYQESEKVGEAIVL TVPGSERSYDLTGLKPGTEYTVSIYGVDVKYDIDSRPISSNPLSAIF TT |
| P283AR9P1362_F12 | 125 | LPAPKNLVVSRVTEDSARLSWARNITSFDSFLIQYQESEKVGEAIVL TVPGSERSYDLTGLKPGTEYTVSIYGVDVKYDIDSRPISSNPLSAIF TT |
| P283AR9P1362_F2 | 126 | LPAPKNLVVSRVTEDSARLSWRKKDHPFDSFLIQYQESEKVGEAIVL TVPGSERSYDLTGLKPGTEYTVSIYGVDVKYDIDSRPISSNPLSAIF TT |
| P283AR9P1362_F8 | 127 | LPAPKNLVVSRVTEDSARLSWGYYHGHFDSFLIQYQESEKVGEAIVL TVPGSERSYDLTGLKPGTEYTVSIYGVDVKWEGNRPVASNPLSAIFT T |
| P283AR9P1362_G11 | 128 | LPAPKNLVVSRVTEDSARLSWRKEATSFDSFLIQYQESEKVGEAIVL TVPGSERSYDLTGLKPGTEYTVSIYGVDVKYDIDSRPISSNPLSAIF TT |
| P283AR9P1362_G3 | 129 | LPAPKNLVVSRVTEDSARLSWVKRATSFDSFLIQYQESEKVGEAIVL TVPGSERSYDLTGLKPGTEYTVSIYGVDVKWEGNRPVASNPLSAIFT T |
| P283AR9P1362_H11 | 130 | LPAPKNLVVSRVTEDSARLSWPKIQGQHFDSFLIQYQESEKVGEAIV LTVPGSERSYDLTGLKPGTEYTVSIYGVDVKYDIDSRPISSNPLSAI FTT |
| P283BR9P1363_A10 | 131 | LPAPKNLVVSRVTEDSARLSWQRADDILPYFDSFLIQYQESEKVGEA IVLTVPGSERSYDLTGLKPGTEYTVSIYGVDVKYDIDSRPISSNPLS AIFTT |
| P283BR9P1363_A8 | 132 | LPAPKNLVVSRVTEDSARLSWVRSDTARFFDSFLIQYQESEKVGEAI VLTVPGSERSYDLTGLKPGTEYTVSIYGVDVKYDIDSRPISSNPLSA IFTT |
| P283BR9P1363_B2 | 133 | LPAPKNLVVSRVTEDSARLSWASTVDPHPRFDSFLIQYQESEKVGEA IVLTVPGSERSYDLTGLKPGTEYTVSIYGVDVKYDIDSRPISSNPLS AIFTT |

-continued

| | | |
|---|---|---|
| P283BR9P1363_B6 | 134 | LPAPKNLVVSRVTEDSARLSWQRHSDAHPLFDSFLIQYQESEKVGEA IVLTVPGSERSYDLTGLKPGTEYTVSIYGVDVKWEGNRPVASNPLSA IFTT |
| P283BR9P1363_C4 | 135 | LPAPKNLVVSRVTEDSARLSWPIVNTPLHFDSFLIQYQESEKVGEAI VLTVPGSERSYDLTGLKPGTEYTVSIYGVDVQYTATGQPERSNPLSA IFTT |
| P283BR9P1363_C8 | 136 | LPAPKNLVVSRVTEDSARLSWAKTSDLHPLFDSFLIQYQESEKVGEA IVLTVPGSERSYDLTGLKPGTEYTVSIYGVDVKWEGNRPVASNPLSA IFTT |
| P283BR9P1363_D11 | 137 | LPAPKNLVVSRVTEDSARLSWNKKHDGQPTFDSFLIQYQESEKVGEA IVLTVPGSERSYDLTGLKPGTEYTVSIYGVDVVYEGSYPASSNPLSA IFTT |
| P283BR9P1363_E4 | 138 | LPAPKNLVVSRVTEDSARLSWIKSETSQPAFDSFLIQYQESEKVGEA IVLTVPGSERSYDLTGLKPGTEYTVSIYGVDVKWEGNRPVASNPLSA IFTT |
| P283BR9P1363_E6 | 139 | LPAPKNLVVSRVTEDSARLSWYARKFISPFDSFLIQYQESEKVGEAI VLTVPGSERSYDLTGLKPGTEYTVSIYGVDVKWEGNRPVASNPLSAI FTT |
| P283BR9P1363_F2 | 140 | LPAPKNLVVSRVTEDSARLSWYRPDNRAGAFDSFLIQYQESEKVGEA IVLTVPGSERSYDLTGLKPGTEYTVSIYGVDVKYDIDSRPISSNPLS AIFTT |
| P283BR9P1363_F4 | 141 | LPAPKNLVVSRVTEDSARLSWERIVQ.TPHFDSFLIQYQESEKVGEA IVLTVPGSERSYDLTGLKPGTEYTVSIYGVDVKWEGNRPVASNPLSA IFTT |
| P283BR9P1363_F6 | 142 | LPAPKNLVVSRVTEDSARLSWPEEAVTATSFDSFLIQYQESEKVGEA IVLTVPGSERSYDLTGLKPGTEYTVSIYGVDVKWEGNRPVASNPLSA IFTT |
| P283BR9P1363_G2 | 143 | LPAPKNLVVSRVTEDSARLSWPKNQTNRHFDSFLIQYQESEKVGEAI VLTVPGSERSYDLTGLKPGTEYTVSIYGVDVKWEGNRPVASNPLSAI FTT |
| P283BR9P1363_G5 | 144 | LPAPKNLVVSRVTEDSARLSWYRATTPAPHFDSFLIQYQESEKVGEA IVLTVPGSERSYDLTGLKPGTEYTVSIYGVDVKWEGNRPVASNPLSA IFTT |
| P283BR9P1363_G7 | 145 | LPAPKNLVVSRVTEDSARLSWSAKKFPRHFDSFLIQYQESEKVGEAI VLTVPGSERSYDLTGLKPGTEYTVSIYGVDVKWEGNRPVASNPLSAI FTT |
| P283DR9P1364_A4 | 146 | LPAPKNLVVSRVTEDSARLSWTAPDAAFDSFYIAYPEWPVQGEAIVL TVPGSERSYDLTGLKPGTEYFVIIYGVKGGDWSEPLSAIFTT |
| P283DR9P1364_A7 | 147 | LPAPKNLVVSRVTEDSARLSWTAPDAAFDSFRIAYPEWPVRGDAIVL TVPGSERSYDLTGLKPGTEYWVIIQGVKGGTDSFPLSAIFTT |
| P283DR9P1364_B1 | 148 | LPAPKNLVVSRVTEDSARLSWTAPDAAFDSFYITYPEIPLGGEAIVL TVPGSERSYDLTGLKPGTEYFVVIYGVKGGLLSSPLSAIFTT |
| P283DR9P1364_B11 | 149 | LPAPKNLVVSRVTEDSARLSWTAPDAAFDSFYISYPEWEQLGEAIVL TVPGSERSYDLTGLKPGTEYFVVIYGVKGGALSAPLSAIFTT |
| P283DR9P1364_B4 | 150 | LPAPKNLVVSRVTEDSARLSWTAPDAAFDSFAISYPEWPPPGEAIVL TVPGSERSYDLTGLKPGTEYWVIILGVKGGDQSWPLSAIFTT |
| P283DR9P1364_C10 | 151 | LPAPKNLVVSRVTEDSARLSWTAPDAAFDSFQIAYPEWPKDGEAIVL TVPGSERSYDLTGLKPGTEYAVFIWGVKGGVYSNPLSAIFTT |
| P283DR9P1364_D11 | 152 | LPAPKNLVVSRVTEDSARLSWTAPDAAFDSFDIAYPEWPPKGEAIVL TVPGSERSYDLTGLKPGTEYFVVIYGVKGGIHSAPLSAIFTT |
| P283DR9P1364_D8 | 153 | LPAPKNLVVSRVTEDSARLSWTAPDAAFDSFQIAYPETPIQGEAIVL TVPGSERSYDLTGLKPGTEYFVIIHGVKGGITSFPLSAIFTT |
| P283DR9P1364_D9 | 154 | LPAPKNLVVSRVTEDSARLSWTAPDAAFDSFGISYPEWPPLGEAIVL TVPGSERSYDLTGLKPGTEYWVIIFGVKGGERSWPLSAIFTT |
| P283DR9P1364_E3 | 155 | LPAPKNLVVSRVTEDSARLSWTAPDAAFDSFGIAYPELPIGGEAIVL TVPGSERSYDLTGLKPGTEYFVIIRGVKGGTLSPPLSAIFTT |

-continued

| | | |
|---|---|---|
| P283DR9P1364_E5 | 156 | LPAPKNLVVSRVTEDSARLSWTAPDAAFDSFWISYPEWPVPGEAIVL TVPGSERSYDLTGLKPGTEYWVIIQGVKGGKLSWPLSAIFTT |
| P283DR9P1364_E7 | 157 | LPAPKNLVVSRVTEDSARLSWTAPDAAFDSFNIAYPEWPVRGEAIVL TVPGSERSYDLTGLKPGTEYWVIIYGVKGGDRSNPLSAIFTT |
| P283DR9P1364_E8 | 158 | LPAPKNLVVSRVTEDSARLSWTAPDAAFDSFSIAYPEWPVHGEAIVL TVPGSERSYDLTGLKPGTEYFVIIYGVKGGVLSEPLSAIFTT |
| P283DR9P1364_E9 | 159 | LPAPKNLVVSRVTEDSARLSWTAPDAAFDSFDIAYPEWPTKGEAIVL TVPGSERSYDLTGLKPGTEYFVVINGVKGGWRSFPLSAIFTT |
| P283DR9P1364_F2 | 160 | LPAPKNLVVSRVTEDSARLSWTAPDAAFDSFWIAYPEWPVPGEAIVL TVPGSERSYDLTGLKPGTEYFVIIQGVKGGFGSFPLSAIFTT |
| P283DR9P1364_F6 | 161 | LPAPKNLVVSRVTEDSARLSWTAPDAAFDSFTIAYPEREQDKWGEAI VLTVPGSERSYDLTGLKPGTEYWVIIQGVKGGRPSTPLSAILTT |
| P283DR9P1364_F8 | 162 | LPAPKNLVVSRVTEDSARLSWTAPDAAFDSFAIAYPEWPPGEAIVLT VPGSERSYDLTGLKPGTEYFVIIYGVKGGWTSPPLSAIFTT |
| P283DR9P1364_G10 | 163 | LPAPKNLVVSRVTEDSARLSWTAPDAAFDSFSIAYPEWPGSGEAIVL TVPGSERSYDLTGLKPGTEYFVVIFGVKGGSQSWPLSAIFTT |
| P283DR9P1364_G9 | 164 | LPAPKNLVVSRVTEDSARLSWTAPDAAFDSFGIWYPEWPVGGEAIVL TVPGSERSYDLTGLKPGTEYWVNISGVKGGEYSFPLSAIFTT |
| P283DR9P1364_H1 | 165 | LPAPKNLVVSRVTEDSARLSWTAPDAAFDSFQISYPEWPVHGEAIVL TVPGSERSYDLTGLKPGTEYWVIIWGVKGGRQSWPLSAIFTT |
| P283DR9P1364_H11 | 166 | LPAPKNLVVSRVTEDSARLSWTAPDAAFDSFDIAYPELPLGGEAIVL TVPGSERSYDLTGLKPGTEYFVIIWGVKGGDRSEPLSAIFTT |
| P283DR9P1364_H6 | 167 | LPAPKNLVVSRVTEDSARLSWTAPDAAFDSFIIAYPETPVRGEAIVL TVPGSERSYDLTGLKPGTEYFVIIIGVKGGQESFPLSAIFTT |
| P283DR9P1364_H9 | 168 | LPAPKNLVVSRVTEDSARLSWTAPDAAFDSFSISYIEYPEIPGGEAI VLTVPGSERSYDLTGLKPGTEYWVPIWGVKGGIQSWPLSAIFTT |
| P283ER9P1365_A1 | 169 | LPAPKNLVVSRVTEDSARLSWTAPDAAFDSFGIAYVEWWHRGEAISL PVPGSERSYDLTGLKPGTEYNVIITGVKGGIPSHPLGAIFTT |
| P283ER9P1365_A7 | 170 | LPAPKNLVVSRVTEDSARLSWTAPDAAFDSFYIPYWESEVYGEAIAL PVPGSERSYDLTGLKPGTEYQVSIIGVKGGVYSQPLAAIFTT |
| P283ER9P1365_B6 | 171 | LPAPKNLVVSRVTEDSARLSWTAPDAAFDSFGIGYAEPVVTGEAISL SVPGSERSYDLTGLKPGTEYWVVIIGVKGGINSYPLGAIFTT |
| P283ER9P1365_C1 | 172 | LPAPKNLVVSRVTEDSARLSWTAPDAAFDSFYIPYWESEVYGEAIAL PVTGSERSYDLTGLKPGTEYQVSIIGVKGGVYSQPLAAIFTT |
| P283ER9P1365_E2 | 173 | LPAPKNLVVSRVTEDSARLSWTAPDAAFDSFYIPYRESEFRGEAIAL PVPGSERSYDLTGLKPGTKYRVIIIGVKGGEFSQPLAAIFTT |
| P283ER9P1365_F4 | 174 | LPAPKNLVVSRVTEDSARLSWTAPDAAFDSFYIPYRESEFRGEAIAL PVPGSERSYDLTGLKPGTKYSVIIIGVKGGEFSQPLGAIFTT |
| P283ER9P1365_G1 | 175 | LPAPKNLVVSRVTEDSARLSWTAPDAAFDSFYIPYRESEFRGEAIAL SVPGSERSYDLTGLKPGTKYRVIIIGVKGGEFSQPLGAIFTT |
| P283ER9P1365_G3 | 176 | LPAPKNLVVSRVTEDSARLSWTAPDAAFDSFGISYYEWAPNGEAIQL SVPGSERSYDLTGLKPGTEYHVVIIGVKGGEPSHPLGAIFTT |
| P283ER9P1365_H3 | 177 | LPAPKNLVVSRVTEDSARLSWTAPDAAFDSFYIPYRESEFRGEAIAL PVPGSERSYDLTGLKPGTKYRVIIIGVKGGEFSQPLSAIFTT |
| P283FR9P1366_A1 | 178 | LPAPKNLVVSRVTEDSARLSWTAPDAAFDSFWITYPEWPVPGEAIVL TVPGSERSYDLTGLKPGTEYAVFIWGVKGGDASEPLSAIFTT |
| P283FR9P1366_A5 | 179 | LPAPKNLVVSRVTEDSARLSWTAPDAAFDSFWIAYPEWPTRGEAIVL TVPGSERSYDLTGLKPGTEYFVVIYGVKGGSPSPPLSAIFTT |
| P283FR9P1366_A9 | 180 | LPAPKNLVVSRVTEDSARLSWTAPDAAFDSFNIAYGEYPGPGEAIVL TVPGSERSYDLTGLKPGTEYWVPIWGVKGGELSEPLSAIFTT |
| P283FR9P1366_B7 | 181 | LPAPKNLVVSRVTEDSARLSWTAPDAAFDSFWITYPEWPVNGEAIVL TVPGSERSYDLTGLKPGTEYWVVIWGVKGGVESPPLSAIFTT |

-continued

| | | |
|---|---|---|
| P283FR9P1366_C2 | 182 | LPAPKNLVVSRVTEDSARLSWTAPDAAFDSFKISYPEWPPEGEAIVL TVPGSERSYDLTGLKPGTEYAVFIWCVKGGEHSWPLSAIFTT |
| P283FR9P1366_C3 | 183 | LPAPKNLVVSRVTEDSARLSWTAPDAAFDSFKIAYPEWPDGGEAIVL TVPGSERSYDLTGLKPGTEYFVIIYGVKGGILSPPLSAIFTT |
| P283FR9P1366_C4 | 184 | LPAPKNLVVSRVTEDSARLSWTAPDAAFDSFNIAYPEWPVRGEAIVL TVPGSERSYDLTGLKPGTEYWVIIIGVKGGEDSWPLSAIFTT |
| P283FR9P1366_C6 | 185 | LPAPKNLVVSRVTEDSARLSWTAPDAAFDSFSIAYPEWPVYGEAIVL TVPGSERSYDLTGLKPGTEYFVVIYGVKGGNYSDPLSAIFTT |
| P283FR9P1366_D12 | 186 | LPAPKNLVVSRVTEDSARLSWTAPDAAFDSFDIAYPEWPLGGEAIVL TVPGSERSYDLTGLKPGTEYWVIILGVKGGDQSWPLSAIFTT |
| P283FR9P1366_D6 | 187 | LPAPKNLVVSRVTEDSARLSWTAPDAAFDSFNIFYPELVFPGEAIVL TVPGSERSYDLTGLKPGTEYWVNISGVKGGEHSWPLSAIFTT |
| P283FR9P1366_D7 | 188 | LPAPKNLVVSRVTEDSARLSWTAPDAAFDSFSIAYPELPVKGEAIVL TVPGSERSYDLTGLKPGTEYFVVIWGVKGGTYSGPLSAIFTT |
| P283FR9P1366_D8 | 189 | LPAPKNLVVSRVTEDSARLSWTAPDAAFDSFEIAYPEIPIAGEAIVL TVPGSERSYDLTGLKPGTEYFVIIYGVKGGDWSDPLSAIFTT |
| P283FR9P1366_E11 | 190 | LPAPKNLVVSRVTEDSARLSWTAPDAAFDSFDIAYPEWPVPGEAIVL TVPGSERSYDLTGLKPGTEYWVIIKGVKGGNISWPLSAIFTT |
| P283FR9P1366_F5 | 191 | LPAPKNLVVSRVTEDSARLSWTAPDAAFDSFDIGYPEWPIKGEAIVL TVPGSERSYDLTGLKPGTEYWVIIWGVKGGDRSEPLSAIFTT |
| P283FR9P1366_F8 | 192 | LPAPKNLVVSRVTEDSARLSWTAPDAAFDSFAIAYPEIAKWGEAIVL TVPGSERSYDLTGLKPGTEYFVIIYGVKGGVHSFPLSAIFTT |
| P283FR9P1366_F9 | 193 | LPAPKNLVVSRVTEDSARLSWTAPDAAFDSFHIFYPELPIAGEAIVL TVPGSERSYDLTGLKPGTEYWVNISGVKGGYESWPLSAIFTT |
| P283FR9P1366_G1 | 194 | LPAPKNLVVSRVTEDSARLSWTAPDAAFDSFYISYPELPVEGEAIVL TVPGSERSYDLTGLKPGTEYWVIIWGVKGGATSEPLSAIFTT |
| P283FR9P1366_G5 | 195 | LPAPKNLVVSRVTEDSARLSWTAPDAAFDSFQIAYPEYPALGEAIVL TVPGSERSYDLTGLKPGTEYFVIIIGVKGGDESFPLSAIFTT |
| P283FR9P1366_G8 | 196 | LPAPKNLVVSRVTEDSARLSWTAPDAAFDSFDIAYPELPIGGEAIVL TVPGSERSYDLTGLKPGTEYFVVIYGVKGGIHSAPLSAIFTT |
| P283FR9P1366_H10 | 197 | LPAPKNLVVSRVTEDSARLSWTAPDAAFDSFNIAYPEWPPEGEAIVL TVPGSERSYDLTGLKPGTEYFVVIYGVKGGHLSDPLSAIFTT |
| P283FR9P1366_H11 | 198 | LPAPKNLVVSRVTEDSARLSWTAPDAAFDSFQIQYLETAPDGEAIVL TVPGSERSYDLTGLKPGTEYYVWIPGVKGGAFSPLSAIFTT |
| P283FR9P1366_H3 | 199 | LPAPKNLVVSRVTEDSARLSWTAPDAAFDSFAIAYPEWPIKGEAIVL TVPGSERSYDLTGLKPGTEYWVVIYGVKGGVFSEPLSAIFTT |
| P283FR9P1366_H5 | 200 | LPAPKNLVVSRVTEDSARLSWTAPDAAFDSFIYIENKVNGEAIVLTV PGSERSYDLTGLKPGTEYHVTIGGVKGGTESNTLSAIFTT |
| P283FR9P1366_H6 | 201 | LPAPKNLVVSRVTEDSARLSWTAPDAAFDSFDIAYPEWPVTGEAIVL TVPGSERSYDLTGLKPGTEYWVIIFGVKGGERSWPLSAIFTT |
| P283FR9P1366_H7 | 202 | LPAPKNLVVSRVTEDSARLSWTAPDAAFDSFQIAYPEYPALGEAIVL TVPGSERSYDLTGLKPGTEYFVIIAGVKGGIQSWPLSAIFTT |
| P283FR9P1366_H8 | 203 | LPAPKNLVVSRVTEDSARLSWTAPDAAFDSFYISYPEWPGSGEAIVL TVPGSERSYDLTGLKPGTEYAVFIWCVKGGWLSDPLSAIFTT |
| P283FR9P1366_H9 | 204 | LPAPKNLVVSRVTEDSARLSWTAPDAAFDSFEIAYPEWPVNGEAIVL TVPGSERSYDLTGLKPGTEYWVVIWGVKGGVNSYPLSAIFTT |
| P283GR7P1367_A11 | 205 | LPAPKNLVVSRVTEDSARLSWTAPDAAFDSFDIAYPEWPTDGEAIVL TVPGSERSYDLTGLKPGTEYFVIIYGVKGGSYSEPLSAIFTT |
| P283GR7P1367_B4 | 206 | LPAPKNLVVSRVTEDSARLSWTAPDAAFDSFSILYYELPPSGEAIVL TVPGSERSYDLTGLKPGTEYTVSIFGVKGGDNSFPLSAIFTT |
| P283GR7P1367_B7 | 207 | LPAPKNLVVSRVTEDSARLSWTAPDAAFDSFDIAYPEWPTDGEAIVL TVPGSERSYDLTGLKPGTEYFVVIYGVKGGHWSYPLSAIFTT |

-continued

| | | |
|---|---|---|
| P283GR7P1367_B9 | 208 | LPAPKNLVVSRVTEDSARLSWTAPDAAFDSFEIWYHEYHPRGEAIVL TVPSSERSYDLTGLKPGTEYDVVISGVKGGHWSYPLSAIFTT |
| P283GR7P1367_C9 | 209 | LPAPKNLVVSRVTEDSARLSWTAPDAAFDSFLIGYPEWPLGGEAIVL TVPGSERSYDLTGLKPGTEYWVIIYGVKGGEYSDPLSAIFTT |
| P283GR7P1367_E5 | 210 | LPAPKNLVVSRVTEDSARLSWTAPDAAFDSFEIWYHEYHPRGEAIVL TVPGSERSYDLTGLKPGTEYDVVISGVKGGHWSYPLSAIFTT |
| P283GR7P1367_F5 | 211 | LPAPKNLVVSRVTEDSARLSWTAPDAAFDSFDIAYPEWPTDGEAIVL TVPGSERSYDLTGLKPGTEYFVIIYGVKGGALSRPLSAIFTT |
| P283GR7P1367_G8 | 212 | LPAPKNLVVSRVTEDSARLSWTAPDAAFDSFYIAYPEYVWGGEATSL GEAIVLTVPGSERSYDLTGLKPGTEYFVVITGVKGGLGSYPLSAIFT T |
| P283GR7P1367_H2 | 213 | LPAPKNLVVSRVTEDSARLSWTAPDAAFDSFDIAYPEWPTDGEAIVL TVPGSERSYDLTGLKPGTEYFVVIYGVKGGGRSYPLSAIFTT |
| P283GR7P1367_H8 | 214 | LPAPKNLVVSRVTEDSARLSWTAPDAAFDSFSINYWEEDPAGEAIVL TVPGSERSYDLTGLKPGTEYRVLIGGVKGGHGSLPLSAIFTT |
| P283GR7P1367_H9 | 215 | LPAPKNLVVSRVTEDSARLSWTAPDAAFDSFDIAYPEWPTDGEAIVL TVPGSERSYDLTGLKPGTEYFVVIYGVKGGGRSAPLSAIFTT |
| P283HR7P1368_A10 | 216 | LPAPKNLVVSRVTEDSARLSWTAPDAAFDSFWIFYLEPFPRGEAIPL EVPGSERSYDLTGLKPGTEYSVDIRGVKGGDHSDPLWAYFTT |
| P283HR7P1368_B12 | 217 | LPAPKNLVVSRVTEDSARLSWTAPDAAFDSFGIGYVEFTRAGEAISL SVPGSERSYDLTGLKPGTEYHVVIIGVKGGEPSHPLGAPFTT |
| P283HR7P1368_C3 | 218 | LPAPKNLVVSRVTEDSARLSWTAPDAAFDSFGIGYAEPAVTGEAISL SVPGSKRSYDLTGLKPGTEYWVVIIGVKGGINSYPLGASFTT |
| P283HR7P1368_D1 | 219 | LPAPKNLVVSRVTEDSARLSWTAPDAAFDSFGISYYEWAPNGEAIQL SVPGSERSYDLTGLKPGTEYHVVIIGVKGGEPSHPLGAPFTT |
| P283HR7P1368_D2 | 220 | LPAPKNLVVSRVTEDSARLSWTAPDAAFNSFGIGYAEPAVTGEAISL SVPGSERSYDLTGLKPGTEYWVVIIGVKGGINSYPLGASFTT |
| P283HR7P1368_D4 | 221 | LPAPKNLVVSRVTEDSARLSWTAPDAAFDSFAIWCVEPIPEGEAIPL FVPGSERSYDLTGLKPGTEYRVGIRGVKGGTFSSPLAAPFTT |
| P283HR7P1368_F10 | 222 | LPAPKNLVVSRVTEDSARLSWTAPDAAFDSFYIPYRESEFRGEAIAL PVPGSERSYDLTGLKPGTKYRVIIIGVKGGEFSQPLGAIFTT |
| P283HR7P1368_F6 | 223 | LPAPKNLVVSRVTEDSARLSWTAPDAAFDSFGIGYIEWVHRGEAISL HVPGSERSYDLTGLKPGTEYVVAIVGVKGGEPSTPLGAPFTT |
| P283HR7P1368_G1 | 224 | LPAPKNLVVSRVTEDSARLSWTAPDAAFDSFLITYWEIEPEGEAIFL GVPGSERSYDLTGLKPGTEYRVQINGVKGGTISYPLFAGFTT |
| P283HR7P1368_G10 | 225 | LPAPKNLVVSRVTEDSARLSWTAPDAAFDSFGIAYVEWWHRGEAISL PVPGSERSYDLTGLKPGTEYWVTILGVKGGIISTPLGASFTT |
| P283HR7P1368_G11 | 226 | LPAPKNLVVSRVTEDSARLSWTAPDAAFDSFGIGYAEPAVTGEAISL SVPGSERSYDLTGLKPGTEYWVVIIGVKGGINSYPLGASFTT |
| P283HR7P1368_H1 | 227 | LPAPKNLVVSRVTEDSARLSWTAPDAAFDSFGIAYIETARWGEAISL TVPGSERSYDLTGLKPGTEYNVVIIGVKGGTPSHPLGAPFTT |
| P283HR7P1368_H8 | 228 | LPAPKNLVVSRVTEDSARLSWTAPDAAFDSFGITYLDPRNGEAISLN VPGSERSYDLTGLKPGTEYWVVIIGVKGGINSYPLGASFTT |
| CD8S368 | 229 | LPAPKNLVVSRVTEDSARLSWTAPDAAFDSFQIAYPEWPPPGEAIVL TVPGSCRSYDLTGLKPGTEYFVIIQGVKGGVESWPLSAIFTT |
| CD8S367 | 230 | LPAPKNLVVSRVTEDSARLSWTAPDAAFDSFAIAYPEWPPQGEAIVL TVPGSCRSYDLTGLKPGTEYFVVIYGVKGGSYSAPLSAIFTT |
| CD8S370 | 231 | LPAPKNLVVSRVTEDSARLSWTAPDAAFDSFAITYIEKEHIEDGEAI VLTVPGSCRSYDLTGLKPGTEYWVPIWGVKGGANSWPLSAIFTT |
| CD8S365 | 232 | LPAPKNLVVSRVTEDSARLSWTAPDAAFDSFGILYYEPVDSGEAITL PVPGSCRSYDLTGLKPGTEYWVVITGVKGGAPSTPLGTIFTT |
| CD8S369 | 233 | LPAPKNLVVSRVTEDSARLSWAKRPGAFDSFLIQYQESEKVGEAIVL TVPGSCRSYDLTGLKPGTEYTVSIYGVDVKYDIDSRPISSNPLSAIF TT |

-continued

| Clone | SEQ ID No | Parent | Sequence |
|---|---|---|---|
| CD8S366 | 234 | | LPAPKNLWSRVTEDSARLSWTAPDAAFDSFWITYPEWPDPGGEAIVL<br>TVPGSCRSYDLTGLKPGTEYFVVIYGVKGGEIYSPLSAIFTT |
| CD8S371 | 235 | P282DR9P1359_F5 | LPAPKNLVVSRVTEDSARLSWTA<br>PDAAFDSFQIAYPEYPPPGEAIV<br>LTVPGSERSYDLTGLKPGTEYFV<br>IIQGVKGGVESWPLSAIFTT |
| CD8S372 | 236 | P282DR9P1359_F5 | LPAPKNLVVSRVTEDSARLSWTA<br>PDAAFDSFQIAYPELPPPGEAIV<br>LTVPGSERSYDLTGLKPGTEYFV<br>IIQGVKGGVESWPLSAIFTT |
| CD8S373 | 237 | P282DR9P1359_F5 | LPAPKNLVVSRVTEDSARLSWTA<br>PDAAFDSFQIAYPEIPPPGEAIV<br>LTVPGSERSYDLTGLKPGTEYFV<br>IIQGVKGGVESWPLSAIFTT |
| CD8S374 | 238 | P282DR9P1359_F5 | LPAPKNLVVSRVTEDSARLSWTA<br>PDAAFDSFQIAYPEWPPPGEAIV<br>LTVPGSERSYDLTGLKPGTEYFV<br>IIQGVKGGVESYPLSAIFTT |
| CD8S375 | 239 | P282DR9P1359_F5 | LPAPKNLVVSRVTEDSARLSWTA<br>PDAAFDSFQIAYPEWPPPGEAIV<br>LTVPGSERSYDLTGLKPGTEYFV<br>IIQGVKGGVESLPLSAIFTT |
| CD8S376 | 240 | P282DR9P1359_F5 | LPAPKNLVVSRVTEDSARLSWTA<br>PDAAFDSFQIAYPEWPPPGEAIV<br>LTVPGSERSYDLTGLKPGTEYFV<br>IIQGVKGGVESSPLSAIFTT |
| CD8S377 | 241 | P282DR9P1359_F5 | LPAPKNLVVSRVTEDSARLSWTA<br>PDAAFDSFQIAYPEWPPPGEAIV<br>LTVPGSERSYDLTGLKPGTEYFV<br>IIQGVKGGVESEPLSAIFTT |
| CD8S378 | 242 | P282DR9P1359_G7 | LPAPKNLVVSRVTEDSARLSWTA<br>PDAAFDSFAITYIEKEHIEEGEA<br>IVLTVPGSERSYDLTGLKPGTEY<br>WVPIWGVKGGANSWPLSAIFTT |
| CD8S379 | 243 | P282DR9P1359_G7 | LPAPKNLVVSRVTEDSARLSWTA<br>PDAAFDSFAITYIEKEHIESGEA<br>IVLTVPGSERSYDLTGLKPGTEY<br>WVPIWGVKGGANSWPLSAIFTT |
| CD8S380 | 244 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>YVPIWGVKGGANSWPLSAIFTT |
| CD8S381 | 245 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>FVPIWGVKGGANSWPLSAIFTT |
| CD8S382 | 246 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>SVPIWGVKGGANSWPLSAIFTT |
| CD8S383 | 247 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>WVPIYGVKGGANSWPLSAIFTT |
| CD8S384 | 248 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>WVPIFGVKGGANSWPLSAIFTT |
| CD8S385 | 249 | P282DR9P1359_G7 | LPAPKNLVVSRVTEDSARLSWTA<br>PDAAFDSFAITYIEKEHIEDGEA |

-continued

| | | | |
|---|---|---|---|
| | | | IVLTVPGSERSYDLTGLKPGTEY<br>WVPISGVKGGANSWPLSAIFTT |
| CD8S386 | 250 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>WVPIWGVKGGANSYPLSAIFTT |
| CD8S387 | 251 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>WVPIWGVKGGANSEPLSAIFTT |
| CD8S388 | 252 | P282DR9P1359_G7 | LPAPKNLVVSRVTEDSARLSWTA<br>PDAAFDSFAITYIEKEHIEDGEA<br>IVLTVPGSERSYDLTGLKPGTEY<br>WVPIWGVKGGAQSWPLSAIFTT |
| CD8S389 | 253 | P282ER9P1360_C8 | LPAPKNLVVSRVTEDSARLSWTA<br>PDAAFDSFGILYYEPVDSGEAIT<br>LPVPGSERSYDLTGLKPGTEYFV<br>VITGVKGGAPSTPLGTIFTT |
| CD8S390 | 254 | P282ER9P1360_C8 | LPAPKNLVVSRVTEDSARLSWTA<br>PDAAFDSFGILYYEPVDSGEAIT<br>LPVPGSERSYDLTGLKPGTEYYV<br>VITGVKGGAPSTPLGTIFTT |
| CD8S391 | 255 | P282ER9P1360_C8 | LPAPKNLVVSRVTEDSARLSWTA<br>PDAAFDSFGILYYEPVDSGEAIT<br>LPVPGSERSYDLTGLKPGTEYHV<br>VITGVKGGAPSTPLGTIFTT |
| CD8S392 | 256 | P282DR9P1359_F7 | LPAPKNLVVSRVTEDSARLSWTA<br>PDAAFDSFAIAYPEYPPQGEAIV<br>LTVPGSERSYDLTGLKPGTEYFV<br>VIYGVKGGSYSAPLSAIFTT |
| CD8S393 | 257 | P282DR9P1359_F7 | LPAPKNLVVSRVTEDSARLSWTA<br>PDAAFDSFAIAYPELPPQGEAIV<br>LTVPGSERSYDLTGLKPGTEYFV<br>VIYGVKGGSYSAPLSAIFTT |
| CD8S394 | 258 | P282DR9P1359_F7 | LPAPKNLVVSRVTEDSARLSWTA<br>PDAAFDSFAIAYPEIPPQGEAIV<br>LTVPGSERSYDLTGLKPGTEYFV<br>VIYGVKGGSYSAPLSAIFTT |
| CD8S395 | 259 | P282DR9P1359_F7 | LPAPKNLVVSRVTEDSARLSWTA<br>PDAAFDSFAIAYPEHPPQGEAIV<br>LTVPGSERSYDLTGLKPGTEYFV<br>VIYGVKGGSYSAPLSAIFTT |
| CD8S396 | 260 | P282DR9P1359_C5 | LPAPKNLVVSRVTEDSARLSWTA<br>PDAAFDSFYITYPEWPDPGGEAI<br>VLTVPGSERSYDLTGLKPGTEYF<br>VVIYGVKGGEIYSPLSAIFTT |
| CD8S397 | 261 | P282DR9P1359_C5 | LPAPKNLVVSRVTEDSARLSWTA<br>PDAAFDSFQITYPEWPDPGGEAI<br>VLTVPGSERSYDLTGLKPGTEYF<br>VVIYGVKGGEIYSPLSAIFTT |
| CD8S398 | 262 | P282DR9P1359_C5 | LPAPKNLVVSRVTEDSARLSWTA<br>PDAAFDSFSITYPEWPDPGGEAI<br>VLTVPGSERSYDLTGLKPGTEYF<br>VVIYGVKGGEIYSPLSAIFTT |
| CD8S399 | 263 | P282DR9P1359_C5 | LPAPKNLVVSRVTEDSARLSWTA<br>PDAAFDSFWITYPEYPDPGGEAI<br>VLTVPGSERSYDLTGLKPGTEYF<br>VVIYGVKGGEIYSPLSAIFTT |
| CD8S400 | 264 | P282DR9P1359_C5 | LPAPKNLVVSRVTEDSARLSWTA<br>PDAAFDSFWITYPELPDPGGEAI<br>VLTVPGSERSYDLTGLKPGTEYF<br>VVIYGVKGGEIYSPLSAIFTT |

-continued

| | | | |
|---|---|---|---|
| CD8S401 | 265 | P282DR9P1359_C5 | LPAPKNLVVSRVTEDSARLSWTA PDAAFDSFWITYPEIPDPGGEAI VLTVPGSERSYDLTGLKPGTEYF VVIYGVKGGEIYSPLSAIFTT |
| CD8S402 | 266 | P282DR9P1359_C5 | LPAPKNLVVSRVTEDSARLSWTA PDAAFDSFWITYPEWPPPGGEAI VLTVPGSERSYDLTGLKPGTEYF VVIYGVKGGEIYSPLSAIFTT |
| CD8S403 | 267 | P282DR9P1359_F7 | LPAPKNLVVSRVTEDSARLSWTA PDAAFDSFAIAYAEWPPQGEAIV LTVPGSERSYDLTGLKPGTEYFV VIYGVKGGSYSAPLSAIFTT |
| CD8S404 | 268 | P282DR9P1359_C5 | LPAPKNLVVSRVTEDSARLSWTA PDAAFDSFWITYAEWPDPGGEAI VLTVPGSERSYDLTGLKPGTEYF VVIYGVKGGEIYSPLSAIFTT |
| CD8S405 | 269 | P282ER9P1360_C8 | LPAPKNLVVSRVTEDSARLSWTA PDAAFDSFGILYYEPVDSGEAIT LTVPGSERSYDLTGLKPGTEYWV VITGVKGGAPSTPLGTIFTT |

Tencon25

SEQ ID. No. 270

LPAPKNLVVSEVTEDSARLSWTAPDAAFDSFLIQYQESEKVGEAIVLTVP

GSERSYDLTGLKPGTEYTVSIYGVKGGHRSNPLSAIFTT

Cyno CD8alpha

SEQ ID. NO: 271

MRNQAPGRPKGATSPPPLPTGSRAPPVAPELRAEPRPGERVMAPPVTALL

LPLVLLLHAARPNQFRVSPLGRTWNLGETVELKCQVLLSNPTSGCSWLFQ

PRGTAARPTFLLYLSQNKPKAAEGLDTQRFSGKRLGDTFVLTLRDFRQEN

EGYYFCSALSNSIMYFSHFVPVFLPAKPTTTPAPRPPTPAPTTASQPLSL

RPEACRPAAGGSVNTRGLDFACDIYIWAPLAGACGVLLLSLVITLYCNHR

NRRRVCKCPRPVVKSGGKPSLSDRYV

SEQUENCE LISTING

```
Sequence total quantity: 281
SEQ ID NO: 1            moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 1
LPAPKNLVVS EVTEDSLRLS WTAPDAAFDS FLIQYQESEK VGEAINLTVP GSERSYDLTG  60
LKPGTEYTVS IYGVKGGHRS NPLSAEFTT                                    89

SEQ ID NO: 2            moltype = AA  length = 94
FEATURE                 Location/Qualifiers
VARIANT                 75..81
                        note = X is any amino acid
VARIANT                 82..86
                        note = X is any amino acid or absent
source                  1..94
                        mol_type = protein
                        organism = synthetic construct
SEQUENCE: 2
LPAPKNLVVS EVTEDSLRLS WTAPDAAFDS FLIQYQESEK VGEAINLTVP GSERSYDLTG  60
LKPGTEYTVS IYGVXXXXXX XXXXXXPLSA EFTT                              94
```

```
SEQ ID NO: 3            moltype = AA  length = 89
FEATURE                 Location/Qualifiers
VARIANT                 22..27
                        note = X is Ala, Arg, Asn, Asp, Glu, Gln, Gly, His, Ile,
                         Leu, Lys, Phe, Pro, Ser, Thr, Trp, Tyr or Val
VARIANT                 28
                        note = X is Phe, Ile, Leu, Val or Tyr
VARIANT                 29
                        note = X is Asp, Glu or Thr
VARIANT                 75..79
                        note = X is Ala, Arg, Asn, Asp, Glu, Gln, Gly, His, Ile,
                         Leu, Lys, Phe, Pro, Ser, Thr, Trp, Tyr or Val
VARIANT                 81..82
                        note = X is Ala, Arg, Asn, Asp, Glu, Gln, Gly, His, Ile,
                         Leu, Lys, Phe, Pro, Ser, Thr, Trp, Tyr or Val
source                  1..89
                        mol_type = protein
                        organism = synthetic construct
SEQUENCE: 3
LPAPKNLVVS EVTEDSLRLS WXXXXXXXXS FLIQYQESEK VGEAINLTVP GSERSYDLTG  60
LKPGTEYTVS IYGVXXXXXS XXLSAEFTT                                    89

SEQ ID NO: 4            moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 4
LPAPKNLVVS RVTEDSARLS WTAPDAAFDS FLIQYQESEK VGEAIVLTVP GSERSYDLTG  60
LKPGTEYTVS IYGVKGGHRS NPLSAIFTT                                    89

SEQ ID NO: 5            moltype = AA  length = 97
FEATURE                 Location/Qualifiers
source                  1..97
                        mol_type = protein
                        organism = synthetic construct
VARIANT                 22..27
                        note = X is Ala, Asp, Glu, Phe, Gly, His, Ile, Lys, Leu,
                         Asn, Pro, Gln, Arg, Ser, Thr, Val, Trp or Tyr
VARIANT                 85..87
                        note = X is Ala, Asp, Glu, Phe, Gly, His, Ile, Lys, Leu,
                         Asn, Pro, Gln, Arg, Ser, Thr, Val, Trp, Tyr, or absent
VARIANT                 28..30
                        note = X is Ala, Asp, Glu, Phe, Gly, His, Ile, Lys, Leu,
                         Asn, Pro, Gln, Arg, Ser, Thr, Val, Trp, Tyr, or absent
VARIANT                 78..84
                        note = X is Ala, Asp, Glu, Phe, Gly, His, Ile, Lys, Leu,
                         Asn, Pro, Gln, Arg, Ser, Thr, Val, Trp or Tyr
SEQUENCE: 5
LPAPKNLVVS RVTEDSARLS WXXXXXXXXX FDSFLIQYQE SEKVGEAIVL TVPGSERSYD  60
LTGLKPGTEY TVSIYGVXXX XXXXXXXSNP LSAIFTT                           97

SEQ ID NO: 6            moltype = AA  length = 96
FEATURE                 Location/Qualifiers
VARIANT                 75..81
                        note = X is Ala, Asp, Glu, Phe, Gly, His, Ile, Lys, Leu,
                         Asn, Pro, Gln, Arg, Ser, Thr, Val, Trp or Tyr
VARIANT                 82..86
                        note = X is Ala, Asp, Glu, Phe, Gly, His, Ile, Lys, Leu,
                         Asn, Pro, Gln, Arg, Ser, Thr, Val, Trp, Tyr, or absent
source                  1..96
                        mol_type = protein
                        organism = synthetic construct
SEQUENCE: 6
LPAPKNLVVS RVTEDSARLS WTAPDAAFDS FLIQYQESEK VGEAIVLTVP GSERSYDLTG  60
LKPGTEYTVS IYGVXXXXXX XXXXXXSNPL SAIFTT                            96

SEQ ID NO: 7            moltype = AA  length = 89
FEATURE                 Location/Qualifiers
VARIANT                 32
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 34
                        note = X is Ala, Asp, Glu, Phe, Gly, His, Ile, Lys, Leu,
                         Asn, Pro, Gln, Arg, Ser, Thr, Val, Trp, Tyr, or Met
```

```
VARIANT                 36
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 38..41
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 68
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 70
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 72
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 78..79
                        note = X is Ala, Asp, Glu, Phe, Gly, His, Ile, Lys, Leu,
                         Asn, Pro, Gln, Arg, Ser, Thr, Val, Trp, Tyr, or Met
VARIANT                 81
                        note = X is Ala, Asp, Glu, Phe, Gly, His, Ile, Lys, Leu,
                         Asn, Pro, Gln, Arg, Ser, Thr, Val, Trp, Tyr, or Met
source                  1..89
                        mol_type = protein
                        organism = synthetic construct
SEQUENCE: 7
LPAPKNLVVS RVTEDSARLS WTAPDAAFDS FXIXYXEXXX XGEAIVLTVP GSERSYDLTG  60
LKPGTEYXVX IXGVKGGXXS XPLSAIFTT                                    89

SEQ ID NO: 8            moltype = AA  length = 89
FEATURE                 Location/Qualifiers
VARIANT                 32
                        note = X is Ala, Asp, Glu, Phe, Gly, His, Ile, Lys, Leu,
                         Asn, Pro, Gln, Arg, Ser, Thr, Val, or Trp
VARIANT                 34
                        note = X is Ala, Asp, Glu, Phe, Gly, His, Ile, Lys, Leu,
                         Asn, Pro, Gln, Arg, Ser, Thr, Val, or Trp
VARIANT                 36
                        note = X is Ala, Asp, Glu, Phe, Gly, His, Ile, Lys, Leu,
                         Asn, Pro, Gln, Arg, Ser, Thr, Val, or Trp
VARIANT                 38..41
                        note = X is Ala, Asp, Glu, Phe, Gly, His, Ile, Lys, Leu,
                         Asn, Pro, Gln, Arg, Ser, Thr, Val, or Trp
VARIANT                 46
                        note = X is Ala, Asp, Glu, Phe, Gly, His, Ile, Lys, Leu,
                         Asn, Pro, Gln, Arg, Ser, Thr, Val, or Trp
VARIANT                 48
                        note = X is Ala, Asp, Glu, Phe, Gly, His, Ile, Lys, Leu,
                         Asn, Pro, Gln, Arg, Ser, Thr, Val, or Trp
VARIANT                 68
                        note = X is Ala, Asp, Glu, Phe, Gly, His, Ile, Lys, Leu,
                         Asn, Pro, Gln, Arg, Ser, Thr, Val, or Trp
VARIANT                 70
                        note = X is Ala, Asp, Glu, Phe, Gly, His, Ile, Lys, Leu,
                         Asn, Pro, Gln, Arg, Ser, Thr, Val, or Trp
VARIANT                 72
                        note = X is Ala, Asp, Glu, Phe, Gly, His, Ile, Lys, Leu,
                         Asn, Pro, Gln, Arg, Ser, Thr, Val, or Trp
VARIANT                 78..79
                        note = X is Ala, Asp, Glu, Phe, Gly, His, Ile, Lys, Leu,
                         Asn, Pro, Gln, Arg, Ser, Thr, Val, or Trp
VARIANT                 81
                        note = X is Ala, Asp, Glu, Phe, Gly, His, Ile, Lys, Leu,
                         Asn, Pro, Gln, Arg, Ser, Thr, Val, or Trp
VARIANT                 84
                        note = X is Ala, Asp, Glu, Phe, Gly, His, Ile, Lys, Leu,
                         Asn, Pro, Gln, Arg, Ser, Thr, Val, or Trp
VARIANT                 86
                        note = X is Ala, Asp, Glu, Phe, Gly, His, Ile, Lys, Leu,
                         Asn, Pro, Gln, Arg, Ser, Thr, Val, or Trp
source                  1..89
                        mol_type = protein
                        organism = synthetic construct
SEQUENCE: 8
LPAPKNLVVS RVTEDSARLS WTAPDAAFDS FXIXYXEXXX XGEAIXLXVP GSERSYDLTG  60
LKPGTEYXVX IXGVKGGXXS XPLXAXFTT                                    89

SEQ ID NO: 9            moltype = DNA  length = 19
FEATURE                 Location/Qualifiers
misc_feature            1..19
```

```
                       note = Description of Artificial Sequence: Synthetic
                        oligonucleotide
source                 1..19
                       mol_type = other DNA
                       organism = synthetic construct
SEQUENCE: 9
gtgacacggc ggttagaac                                             19

SEQ ID NO: 10          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 10
gcctttggga agcttctaag                                            20

SEQ ID NO: 11          moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 11
cggcggttag aacgcggcta caattaatac                                 30

SEQ ID NO: 12          moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 12
catgattacg ccaagctcag aa                                         22

SEQ ID NO: 13          moltype = DNA  length = 385
FEATURE                Location/Qualifiers
variation              198..224
                       note = wherein n is a, c, t, g, unknown or other
source                 1..385
                       mol_type = other DNA
                       organism = synthetic construct
SEQUENCE: 13
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctgaagtt accgaagact  180
ctctgcgtct gtcttggnnn nnnnnnnnnn nnnnnnnnnn nnnnttygac tctttcctga  240
tccagtacca ggaatctgaa aaagttggtg aagcgatcaa cctgaccgtt ccgggttctg  300
aacgttctta cgacctgacc ggtctgaaac cgggtaccga atacaccgtt tctatctacg  360
gtgttcttag aagcttccca aaggc                                      385

SEQ ID NO: 14          moltype = DNA  length = 382
FEATURE                Location/Qualifiers
variation              198..221
                       note = wherein n is a, c, t, g, unknown or other
source                 1..382
                       mol_type = other DNA
                       organism = synthetic construct
SEQUENCE: 14
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctgaagtt accgaagact  180
ctctgcgtct gtcttggnnn nnnnnnnnnn nnnnnnnnnn nttygactct ttcctgatcc  240
agtaccagga atctgaaaaa gttggtgaag cgatcaacct gaccgttccg ggttctgaac  300
gttcttacga cctgaccggt ctgaaaccgg gtaccgaata caccgtttct atctacggtg  360
ttcttagaag cttcccaaag gc                                         382

SEQ ID NO: 15          moltype = DNA  length = 379
FEATURE                Location/Qualifiers
variation              198..218
                       note = wherein n is a, c, t, g, unknown or other
source                 1..379
                       mol_type = other DNA
```

```
                        organism = synthetic construct
SEQUENCE: 15
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctgaagtt accgaagact  180
ctctgcgtct gtcttggnnn nnnnnnnnnn nnnnnnnntt ygactctttc ctgatccagt  240
accaggaatc tgaaaaagtt ggtgaagcga tcaacctgac cgttccgggt tctgaacgtt  300
cttacgacct gaccggtctg aaaccgggta ccgaatacac cgtttctatc tacggtgttc  360
ttagaagctt cccaaaggc                                               379

SEQ ID NO: 16           moltype = DNA  length = 376
FEATURE                 Location/Qualifiers
variation               198..215
                        note = wherein n is a, c, t, g, unknown or other
source                  1..376
                        mol_type = other DNA
                        organism = synthetic construct
SEQUENCE: 16
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctgaagtt accgaagact  180
ctctgcgtct gtcttggnnn nnnnnnnnnn nnnnnnttyga ctctttcctg atccagtacc  240
aggaatctga aaaagttggt gaagcgatca acctgaccgt tccgggttct gaacgttctt  300
acgacctgac cggtctgaaa ccgggtaccg aatacaccgt ttctatctac ggtgttctta  360
gaagcttccc aaaggc                                                  376

SEQ ID NO: 17           moltype = DNA  length = 131
FEATURE                 Location/Qualifiers
misc_feature            1..131
                        note = Description of Artificial Sequence: Synthetic
                         polynucleotide
source                  1..131
                        mol_type = other DNA
                        organism = synthetic construct
SEQUENCE: 17
cggcggttag aacgcggcta caattaatac ataaccccat ccccctgttg acaattaatc  60
atcggctcgt ataatgtgtg gaattgtgag cggataacaa tttcacacag gaaacaggat  120
ctaccatgct g                                                       131

SEQ ID NO: 18           moltype = DNA  length = 30
FEATURE                 Location/Qualifiers
misc_feature            1..30
                        note = Description of Artificial Sequence: Synthetic
                         oligonucleotide
source                  1..30
                        mol_type = other DNA
                        organism = synthetic construct
SEQUENCE: 18
cggcggttag aacgcggcta caattaatac                                   30

SEQ ID NO: 19           moltype = DNA  length = 81
FEATURE                 Location/Qualifiers
misc_feature            1..81
                        note = Description of Artificial Sequence: Synthetic
                         oligonucleotide
source                  1..81
                        mol_type = other DNA
                        organism = synthetic construct
SEQUENCE: 19
ccaagacaga cgggcagagt cttcggtaac gcgagaaaca accaggtttt tcggcgccgg  60
cagcatggta gatcctgttt c                                            81

SEQ ID NO: 20           moltype = DNA  length = 26
FEATURE                 Location/Qualifiers
misc_feature            1..26
                        note = Description of Artificial Sequence: Synthetic
                         oligonucleotide
source                  1..26
                        mol_type = other DNA
                        organism = synthetic construct
SEQUENCE: 20
ccgaagactc tgcccgtctg tcttgg                                       26

SEQ ID NO: 21           moltype = DNA  length = 45
FEATURE                 Location/Qualifiers
misc_feature            1..45
                        note = Description of Artificial Sequence: Synthetic
                         oligonucleotide
source                  1..45
```

```
                       mol_type = other DNA
                       organism = synthetic construct
SEQUENCE: 21
cagtggtctc acggattcct ggtactggat caggaaagag tcgaa                  45

SEQ ID NO: 22          moltype = DNA  length = 54
FEATURE                Location/Qualifiers
misc_feature           1..54
                       note = Description of Artificial Sequence: Synthetic
                        oligonucleotide
source                 1..54
                       mol_type = other DNA
                       organism = synthetic construct
SEQUENCE: 22
catgcggtct cttccgaaaa agttggtgaa gcgatcgtcc tgaccgttcc gggt        54

SEQ ID NO: 23          moltype = DNA  length = 29
FEATURE                Location/Qualifiers
misc_feature           1..29
                       note = Description of Artificial Sequence: Synthetic
                        oligonucleotide
source                 1..29
                       mol_type = other DNA
                       organism = synthetic construct
SEQUENCE: 23
ggtggtgaag atcgcagaca gcgggttag                                    29

SEQ ID NO: 24          moltype = DNA  length = 21
FEATURE                Location/Qualifiers
misc_feature           1..21
                       note = Description of Artificial Sequence: Synthetic
                        oligonucleotide
source                 1..21
                       mol_type = other DNA
                       organism = synthetic construct
SEQUENCE: 24
cggcggttag aacgcggcta c                                            21

SEQ ID NO: 25          moltype = DNA  length = 61
FEATURE                Location/Qualifiers
misc_feature           1..61
                       note = Description of Artificial Sequence: Synthetic
                        oligonucleotide
source                 1..61
                       mol_type = other DNA
                       organism = synthetic construct
SEQUENCE: 25
aagatcagtt gcggccgcta gactagaacc gctgccaccg ccggtggtga agatcgcaga  60
c                                                                  61

SEQ ID NO: 26          moltype = DNA  length = 485
FEATURE                Location/Qualifiers
variation              357..392
                       note = wherein n is a, c, t, g, unknown or other
source                 1..485
                       mol_type = other DNA
                       organism = synthetic construct
SEQUENCE: 26
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnnnnnnn nntctaaccc gctgtctgcg atcttcacca  420
ccggcggtca ccatcaccat caccatggca gcggttctag tctagcggcc gcaactgatc  480
ttggc                                                              485

SEQ ID NO: 27          moltype = DNA  length = 482
FEATURE                Location/Qualifiers
source                 1..482
                       mol_type = other DNA
                       organism = synthetic construct
variation              357..389
                       note = n is a, c, t, g, unknown or other
SEQUENCE: 27
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
```

-continued

```
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnnnnnnt ctaacccgct gtctgcgatc ttcaccaccg  420
gcggtcacca tcaccatcac catggcagcg gttctagtct agcggccgca actgatcttg  480
gc                                                                  482

SEQ ID NO: 28          moltype = DNA  length = 479
FEATURE                Location/Qualifiers
variation              357..386
                       note = wherein n is a, c, t, g, unknown or other
source                 1..479
                       mol_type = other DNA
                       organism = synthetic construct
SEQUENCE: 28
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnnntcta acccgctgtc tgcgatcttc accaccggcg  420
gtcaccatca ccatcaccat ggcagcggtt ctagtctagc ggccgcaact gatcttggc   479

SEQ ID NO: 29          moltype = DNA  length = 476
FEATURE                Location/Qualifiers
variation              357..383
                       note = wherein n is a, c, t, g, unknown or other
source                 1..476
                       mol_type = other DNA
                       organism = synthetic construct
SEQUENCE: 29
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnntctaacc cgctgtctgc gatcttcacc accggcggtc  420
accatcacca tcaccatggc agcggttcta gtctagcggc cgcaactgat cttggc      476

SEQ ID NO: 30          moltype = DNA  length = 473
FEATURE                Location/Qualifiers
variation              357..380
                       note = wherein n is a, c, t, g, unknown or other
source                 1..473
                       mol_type = other DNA
                       organism = synthetic construct
SEQUENCE: 30
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn tctaacccgc tgtctgcgat cttcaccacc ggcggtcacc  420
atcaccatca ccatggcagc ggttctagtc tagcggccgc aactgatctt ggc         473

SEQ ID NO: 31          moltype = DNA  length = 470
FEATURE                Location/Qualifiers
variation              357..377
                       note = wherein n is a, c, t, g, unknown or other
source                 1..470
                       mol_type = other DNA
                       organism = synthetic construct
SEQUENCE: 31
gtgacacggc ggttagaacg cggctacaat taatacataa ccccatcccc ctgttgacaa  60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnntct aacccgctgt ctgcgatctt caccaccggc ggtcaccatc  420
accatcacca tggcagcggt tctagtctag cggccgcaac tgatcttggc             470

SEQ ID NO: 32          moltype = AA  length = 7
FEATURE                Location/Qualifiers
REGION                 1..7
                       note = Description of Artificial Sequence: Synthetic peptide
```

-continued

```
source                  1..7
                        mol_type = protein
                        organism = synthetic construct
SEQUENCE: 32
KGGHRSN                                                            7

SEQ ID NO: 33           moltype = DNA  length = 37
FEATURE                 Location/Qualifiers
misc_feature            1..37
                        note = Description of Artificial Sequence: Synthetic
                         oligonucleotide
source                  1..37
                        mol_type = other DNA
                        organism = synthetic construct
SEQUENCE: 33
aagaaggaga accggtatgc tgccggcgcc gaaaaac                           37

SEQ ID NO: 34           moltype = DNA  length = 65
FEATURE                 Location/Qualifiers
misc_feature            1..65
                        note = Description of Artificial Sequence: Synthetic
                         oligonucleotide
source                  1..65
                        mol_type = other DNA
                        organism = synthetic construct
SEQUENCE: 34
gagccgccgc caccggttta atggtgatgg tgatggtgac caccggtggt gaagatcgca  60
gacag                                                              65

SEQ ID NO: 35           moltype = AA  length = 387
FEATURE                 Location/Qualifiers
REGION                  1..387
                        note = Description of Artificial Sequence: Synthetic
                         polypeptide
source                  1..387
                        mol_type = protein
                        organism = synthetic construct
SEQUENCE: 35
SQFRVSPLDR TWNLGETVEL KCQVLLSNPT SGCSWLFQPR GAAASPTFLL YLSQNKPKAA  60
EGLDTQRFSG KRLGDTFVLT LSDFRRENEG YYFCSALSNS IMYFSHFVPV FLPAKPTTTP  120
APRPPTPAPT IASQPLSLRP EACRPAGSGS GSDYKDDDDK DKTHTCPPCP APELLGGPSV  180
FLFPPKPKDT LMISRTPEVT CVVVDVSHED PEVKFNWYVD GVEVHNAKTK PREEQYNSTY  240
RVVSVLTVLH QDWLNGKEYK CKVSNKALPA PIEKTISKAK GQPREPQVYT LPPSRDELTK  300
NQVSLTCLVK GFYPSDIAVE WESNGQPENN YKTTPPVLDS DGSFFLYSKL TVDKSRWQQG  360
NVFSCSVMHE ALHNHYTQKS LSLSPGK                                      387

SEQ ID NO: 36           moltype = AA  length = 412
FEATURE                 Location/Qualifiers
REGION                  1..412
                        note = Description of Artificial Sequence: Synthetic
                         polypeptide
source                  1..412
                        mol_type = protein
                        organism = synthetic construct
SEQUENCE: 36
SQFRVSPLDR TWNLGETVEL KCQVLLSNPT SGCSWLFQPR GAAASPTFLL YLSQNKPKAA  60
EGLDTQRFSG KRLGDTFVLT LSDFRRENEG YYFCSALSNS IMYFSHFVPV FLPAKPTTTP  120
APRPPTPAPT IASQPLSLRP EACRPAAGGA VHTRGLDFAC DGGGGSDYKD DDDKGGGGSH  180
HHHHHDKTHT CPPCPAPELL GGPSVFLFPP KPKDTLMISR TPEVTCVVVD VSHEDPEVKF  240
NWYVDGVEVH NAKTKPREEQ YNSTYRVVSV LTVLHQDWLN GKEYKCKVSN KALPAPIEKT  300
ISKAKGQPRE PQVYTLPPSR DELTKNQVSL TCLVKGFYPS DIAVEWESNG QPENNYKTTP  360
PVLDSDGSFF LYSKLTVDKS RWQQGNVFSC SVMHEALHNH YTQKSLSLSP GK          412

SEQ ID NO: 37           moltype = AA  length = 20
FEATURE                 Location/Qualifiers
REGION                  1..20
                        note = Description of Unknown: mIgGK signal peptide
source                  1..20
                        mol_type = protein
                        organism = unidentified
SEQUENCE: 37
METDTLLLWV LLLWVPGSTG                                              20

SEQ ID NO: 38           moltype = AA  length = 227
FEATURE                 Location/Qualifiers
source                  1..227
                        mol_type = protein
                        organism = Homo sapiens
SEQUENCE: 38
```

-continued

```
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 39           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 39
GGGGSDYKDD DDKGGGGSHH HHHH                                         24

SEQ ID NO: 40           moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 40
LPAPKNLVVS RVTEDSARLS WHTATNSFDS FLIQYQESEK VGEAIVLTVP GSERSYDLTG  60
LKPGTEYTVS IYGVDVDYNP TGRPVSSNPL SAIFTT                            96

SEQ ID NO: 41           moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 41
LPAPKNLVVS RVTEDSARLS WVKRPNSFDS FLIQYQESEK VGEAIVLTVP GSERSYDLTG  60
LKPGTEYTVS IYGVDVVDYE GRPRWSNPLS AIFTT                             95

SEQ ID NO: 42           moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 42
LPAPKNLVVS RVTEDSARLS WSKTDSSFDS FLIQYQESEK VGEAIVLTVP GSERSYDLTG  60
LKPGTEYTVS IYGVDVVYIE GNPVFSNPLS AIFTT                             95

SEQ ID NO: 43           moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 43
LPAPKNLVVS RVTEDSARLS WPEGDRPFFD SFLIQYQESE KVGEAIVLTV PGSERSYDLT  60
GLKPGTEYTV SIYGVDVKWE GNRPVASNPL SAIFTT                            96

SEQ ID NO: 44           moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 44
LPAPKNLVVS RVTEDSARLS WTRHETSFDS FLIQYRESEK VGEAIVLTVP GSERSYDLTG  60
LKPGTEYTVS IYGVVVEYDA AGNPKYSNPL SAIFTT                            96

SEQ ID NO: 45           moltype = AA  length = 96
FEATURE                 Location/Qualifiers
REGION                  1..96
                        note = Description of Artificial Sequence: Synthetic
```

```
                          polypeptide
source                   1..96
                         mol_type = protein
                         organism = synthetic construct
SEQUENCE: 45
LPAPKNLVVS RVTEDSARLS WIPNPSSFDS FLIQYQESEK VGEAIVLTVP GSERSYDLTG  60
LKPGTEYTVS IYGVDVVFDP VGFPSHSNPL SAIFTT                            96

SEQ ID NO: 46            moltype = AA  length = 96
FEATURE                  Location/Qualifiers
REGION                   1..96
                         note = Description of Artificial Sequence: Synthetic
                          polypeptide
source                   1..96
                         mol_type = protein
                         organism = synthetic construct
SEQUENCE: 46
LPAPKNLVVS RVTEDSARLS WRKRANSFDS FLIQYQESEK VGEAIVLTVP GSERSYDLTG  60
LKPGTEYTVS IYGVHVEYDQ HGRPRWSNPL SAIFTT                            96

SEQ ID NO: 47            moltype = AA  length = 98
FEATURE                  Location/Qualifiers
REGION                   1..98
                         note = Description of Artificial Sequence: Synthetic
                          polypeptide
source                   1..98
                         mol_type = protein
                         organism = synthetic construct
SEQUENCE: 47
LPAPKNLVVS RVTEDSARLS WKANRTTDLH FDSFLIQYQE SEKVGEAIVL TVPGSERSYD  60
LTGLKPGTEY TVSIYGVDVQ YDGQQPLYSN PLSAIFTT                          98

SEQ ID NO: 48            moltype = AA  length = 97
FEATURE                  Location/Qualifiers
REGION                   1..97
                         note = Description of Artificial Sequence: Synthetic
                          polypeptide
source                   1..97
                         mol_type = protein
                         organism = synthetic construct
SEQUENCE: 48
LPAPKNLVVS RVTEDSARLS WNPSEDPQRF DSFLIQYQES EKVGEAIVLT VPGSERSYDL  60
TGLKPGTEYT VSIYGVDVKW EGNRPVASNP LSAIFTT                           97

SEQ ID NO: 49            moltype = AA  length = 97
FEATURE                  Location/Qualifiers
REGION                   1..97
                         note = Description of Artificial Sequence: Synthetic
                          polypeptide
source                   1..97
                         mol_type = protein
                         organism = synthetic construct
SEQUENCE: 49
LPAPKNLVVS RVTEDSARLS WWSNDNRPIF DSFLIQYQES EKVGEAIVLT VPGSERSYDL  60
TGLKPGTEYT VSIYGVDVKW EGNRPVASNP LSAIFTT                           97

SEQ ID NO: 50            moltype = AA  length = 98
FEATURE                  Location/Qualifiers
REGION                   1..98
                         note = Description of Artificial Sequence: Synthetic
                          polypeptide
source                   1..98
                         mol_type = protein
                         organism = synthetic construct
SEQUENCE: 50
LPAPNNLVVS RVTEDSARLS WPFVSQNKPH FDSFLIQYQE SEKVGEAIVL TVPGSERSYD  60
LTGLKPGTEY TVSIYGVDVK WEGNRPVASN PLSAIFTT                          98

SEQ ID NO: 51            moltype = AA  length = 97
FEATURE                  Location/Qualifiers
REGION                   1..97
                         note = Description of Artificial Sequence: Synthetic
                          polypeptide
source                   1..97
                         mol_type = protein
                         organism = synthetic construct
SEQUENCE: 51
LPAPKNLVVS RVTEDSARLS WGQYITAFSF DSFLIQYQES EKVGEAIVLT VPGSERSYDL  60
TGLKPGTEYT VSIYGVDVAW FQGKPTWSNP LSAIFTT                           97
```

```
SEQ ID NO: 52          moltype = AA  length = 97
FEATURE                Location/Qualifiers
REGION                 1..97
                       note = Description of Artificial Sequence: Synthetic
                        polypeptide
source                 1..97
                       mol_type = protein
                       organism = synthetic construct
SEQUENCE: 52
LPAPKNLVVS RVTEDSARLS WIKDGHPRHF DSFLIQYQES EKVGEAIVLT VPGSERSYDL  60
TGLKPGTEYT VSIYGVDVVY DRGQLISSNP LSAIFTT                          97

SEQ ID NO: 53          moltype = AA  length = 97
FEATURE                Location/Qualifiers
REGION                 1..97
                       note = Description of Artificial Sequence: Synthetic
                        polypeptide
source                 1..97
                       mol_type = protein
                       organism = synthetic construct
SEQUENCE: 53
LPAPKNLVVS RVTEDSARLS WWPRKYQRPF DSFLIQYQES EKVGEAIVLT VPGSERSYDL  60
TGLKPGTEYT VSIYGVDIEW IGNRPIASNP LSAIFTT                          97

SEQ ID NO: 54          moltype = AA  length = 99
FEATURE                Location/Qualifiers
REGION                 1..99
                       note = Description of Artificial Sequence: Synthetic
                        polypeptide
source                 1..99
                       mol_type = protein
                       organism = synthetic construct
SEQUENCE: 54
LPAPKNLVVS RVTEDSARLS WPIASQIHSP FDSFLIQYQE SEKVGEAIVL TVPGSERSYD  60
LTGLKPGTEY TVSIYGVDVK YDIDSRPISS NPLSAIFTT                        99

SEQ ID NO: 55          moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 55
LPAPKNLVVS RVTEDSARLS WKKREYQDPG FDSFLIQYQE SEKVGEAIVL TVPGSERSYD  60
LTGLKPGTEY TVSIYGVDVK WEGNRPVASN PLSAIFTT                         98

SEQ ID NO: 56          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 56
LPAPKNLVVS RVTEDSARLS WTAPDAAFDS FKIAYPEWPS NGEAIVLTVP GSERSYDLTG  60
LKPGTEYAVF IWGVKGGAFS NPLSAIFTT                                   89

SEQ ID NO: 57          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 57
LPAPKNLVVS RVTEDSARLS WTAPDAAFDS FLIAYPEWPD SGEAIVLTVP GSERSYDLTG  60
LKPGTEYAVF IWGVKGGPLS HPLSAIFTT                                   89

SEQ ID NO: 58          moltype = AA  length = 89
FEATURE                Location/Qualifiers
REGION                 1..89
                       note = Description of Artificial Sequence: Synthetic
                        polypeptide
source                 1..89
```

```
                         mol_type = protein
                         organism = synthetic construct
SEQUENCE: 58
LPAPKNLVVS RVTEDSARLS WTAPDAAFDS FLISYPEYPP PGEAIVLTVP GSERSYDLTG  60
LKPGTEYFVI IFGVKGGDTS WPLSAIFTT                                    89

SEQ ID NO: 59            moltype = AA  length = 90
FEATURE                  Location/Qualifiers
REGION                   1..90
                         note = Description of Artificial Sequence: Synthetic
                          polypeptide
source                   1..90
                         mol_type = protein
                         organism = synthetic construct
SEQUENCE: 59
LPAPKNLVVS RVTEDSARLS WTAPDAAFDS FLIAYPEWPI FEGEAIVLTV PGSERSYDLT  60
GLKPGTEYFV VIYGVKGGEQ SSPLSAIFTT                                   90

SEQ ID NO: 60            moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 60
LPAPKNLVVS RVTEDSARLS WTAPDAAFDS FWISYPEWPP DGEAIVLTVP GSERSYDLTG  60
LKPGTEYFVI IWGVKGGETS APLSAIFTT                                    89

SEQ ID NO: 61            moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 61
LPAPKNLVVS RVTEDSARLS WTAPEAAFDS FQIAYPEWPP PREAIVLTVP GSERSYDLTG  60
LKPGTEYFVV IQGVKGGEIS WPLSAIFTT                                    89

SEQ ID NO: 62            moltype = AA  length = 91
FEATURE                  Location/Qualifiers
REGION                   1..91
                         note = Description of Artificial Sequence: Synthetic
                          polypeptide
source                   1..91
                         mol_type = protein
                         organism = synthetic construct
SEQUENCE: 62
LPAPKNLVVS RVTEDSARLS WTAPDAAFDS FRIGYPELEK LGYGEAIVLT VPGSERSYDL  60
TGLKPGTEYW VIIWGVKGGE NSWPLSAIFT T                                 91

SEQ ID NO: 63            moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 63
LPAPKNLVVS RVTEDSARLS WTAPDAAFDS FRIAYPEWPV QGEAIVLTVP GSERSYDLTG  60
LKPGTEYFVI IYGVKGGELS PPLSAIFTT                                    89

SEQ ID NO: 64            moltype = AA  length = 96
FEATURE                  Location/Qualifiers
REGION                   1..96
                         note = Description of Artificial Sequence: Synthetic
                          polypeptide
source                   1..96
                         mol_type = protein
                         organism = synthetic construct
SEQUENCE: 64
LPAPKNLVVS RVTEDSARLS WTAPDAAFDS FWIAYTEWPI PYEEAGQEGE AIVLTVPGSE  60
RSYDLTGLKP GTEYWVSIYG VKGGPNSQPL SAIFTT                            96

SEQ ID NO: 65            moltype = AA  length = 89
```

-continued

```
FEATURE               Location/Qualifiers
REGION                1..89
                      note = Description of Artificial Sequence: Synthetic
                       polypeptide
source                1..89
                      mol_type = protein
                      organism = synthetic construct
SEQUENCE: 65
LPAPKNLVVS RVTEDSARLS WTAPDAAFDS FAIVYPEWPT DGEAIVLTVP GSERSYDLTG  60
LKPGTEYAVF IWGVKGGNQS WPLSAIFTT                                    89

SEQ ID NO: 66         moltype = AA  length = 89
FEATURE               Location/Qualifiers
REGION                1..89
                      note = Description of Artificial Sequence: Synthetic
                       polypeptide
source                1..89
                      mol_type = protein
                      organism = synthetic construct
SEQUENCE: 66
LPAPKNLVVS RVTEDSARLS WTAPDAAFDS FKIAYPEFPP PGEAIVLTVP GSERSYDLTG  60
LKPGTEYYVI IIGVKGGTDS WPLSAIFTT                                    89

SEQ ID NO: 67         moltype = AA  length = 89
FEATURE               Location/Qualifiers
REGION                1..89
                      note = Description of Artificial Sequence: Synthetic
                       polypeptide
source                1..89
                      mol_type = protein
                      organism = synthetic construct
SEQUENCE: 67
LPAPKNLVVS RVTEDSARLS WTAPDAAFDS FYISYPEWPV PGEAIVLTVP GSERSYDLTG  60
LKPGTEYWVV IYGVKGGALS VPLSAIFTT                                    89

SEQ ID NO: 68         moltype = AA  length = 90
FEATURE               Location/Qualifiers
REGION                1..90
                      note = Description of Artificial Sequence: Synthetic
                       polypeptide
source                1..90
                      mol_type = protein
                      organism = synthetic construct
SEQUENCE: 68
LPAPKNLVVS RVTEDSARLS WTAPDAAFDS FWITYPEWPD PGGEAIVLTV PGSERSYDLT  60
GLKPGTEYFV VIYGVKGGEI YSPLSAIFTT                                   90

SEQ ID NO: 69         moltype = AA  length = 89
FEATURE               Location/Qualifiers
REGION                1..89
                      note = Description of Artificial Sequence: Synthetic
                       polypeptide
source                1..89
                      mol_type = protein
                      organism = synthetic construct
SEQUENCE: 69
LPAPKNLVVS RVTEDSARLS WTAPDAAFDS FRIAYPETAT WGEAIVLTVP GSERSYDLTG  60
LKPGTEYFVI IYGVKGGFES APLSAIFTT                                    89

SEQ ID NO: 70         moltype = AA  length = 89
FEATURE               Location/Qualifiers
REGION                1..89
                      note = Description of Artificial Sequence: Synthetic
                       polypeptide
source                1..89
                      mol_type = protein
                      organism = synthetic construct
SEQUENCE: 70
LPAPKNLVVS RVTEDSARLS WTAPDAAFDS FYISYPEWPP VGEAIVLTVP GSERSYDLTG  60
LKPGTEYWVI IYGVKGGAIS TPLSAIFTT                                    89

SEQ ID NO: 71         moltype = AA  length = 89
FEATURE               Location/Qualifiers
REGION                1..89
                      note = Description of Artificial Sequence: Synthetic
                       polypeptide
source                1..89
                      mol_type = protein
                      organism = synthetic construct
```

```
SEQUENCE: 71
LPAPKNLVVS RVTEDSARLS WTAPDAAFDS FNIFYPEIVT WGEAIVLTVP GSERSYDLTG  60
LKPGTEYWVN IVGVKGGDNS WPLSAIFTT                                   89

SEQ ID NO: 72          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 72
LPAPKNLVVS RVTEDSARLS WTAPDAAFDS FAIAYPELPL GGEAIVLTVP GSERSYDLTG  60
LKPGTEYFVI IYGVKGGVES FPLSAIFTT                                   89

SEQ ID NO: 73          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 73
LPAPKNLVVS RVTEDSARLS WTAPDAAFDS FAISYPEWPV PGEAIVLTVP GSERSYDLTG  60
LKPGTEYFVI IYGVKGGLYS APLSAIFTT                                   89

SEQ ID NO: 74          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 74
LPAPKNLVVS RVTEDSARLS WTAPDAAFDS FWIAYPEWPV QGEAIVLTVP GSERSYDLTG  60
LKPGTEYFVV IQGVKGGTPS WPLSAIFTT                                   89

SEQ ID NO: 75          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 75
LPAPKNLVVS RVTEDSARLS WTAPDAAFDS FQIAYPEWPV IGEAIVLTVP GSERSYDLTG  60
LKPGTEYWVI IQGVKGGYTS WPLSAIFTT                                   89

SEQ ID NO: 76          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 76
LPAPKNLVVS RVTEDSARLS WTAPDAAFDS FDIFYPELPI HGEAIVLTVP GSERSYDLTG  60
LKPGTEYWVN ITGVKGGDFS WPLSAIFTT                                   89

SEQ ID NO: 77          moltype = AA  length = 99
FEATURE                Location/Qualifiers
REGION                 1..99
                       note = Description of Artificial Sequence: Synthetic
                        polypeptide
source                 1..99
                       mol_type = protein
                       organism = synthetic construct
SEQUENCE: 77
LPAPKNLVVS RVTEDSARLS WTAPDAAFDS FNIAYPEALH PGYGEAIVLT VPGSERSYDL  60
TGLKPGTEYW VIIGGVKGGQ KSWPLSAIFT TGGHHHDHH                        99

SEQ ID NO: 78          moltype = AA  length = 89
FEATURE                Location/Qualifiers
REGION                 1..89
```

```
                        note = Description of Artificial Sequence: Synthetic
                         polypeptide
source                  1..89
                        mol_type = protein
                        organism = synthetic construct
SEQUENCE: 78
LPAPKNLVVS RVTEDSARLS WTAPDAAFDS FYITYPEWPV QGEAIVLTVP GSERSYDLTG  60
LKPGTEYWVI IYGVKGGTES EPLSAIFTT                                    89

SEQ ID NO: 79           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 79
LPAPKNLVVS RVTEDSARLS WTAPDAAFDS FQIAYPEWPP PGEAIVLTVP GSERSYDLTG  60
LKPGTEYFVI IQGVKGGVES WPLSAIFTT                                    89

SEQ ID NO: 80           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 80
LPAPKNLVVS RVTEDSARLS WTAPDAAFDS FDIAYPEWPT TGEAIVLTVP GSERSYDLTG  60
LKPGTEYFVV IWGVKGGDHS APLSAIFTT                                    89

SEQ ID NO: 81           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 81
LPAPKNLVVS RVTEDSARLS WTAPDAAFDS FAIAYPEWPP QGEAIVLTVP GSERSYDLTG  60
LKPGTEYFVV IYGVKGGSYS APLSAIFTT                                    89

SEQ ID NO: 82           moltype = AA  length = 97
FEATURE                 Location/Qualifiers
REGION                  1..97
                        note = Description of Artificial Sequence: Synthetic
                         polypeptide
source                  1..97
                        mol_type = protein
                        organism = synthetic construct
SEQUENCE: 82
LPAPKNLVVS RVTEDSARLS WTAPDAAFDS FEIAYPEWPP PGEAIVLTVP GSERSYDLTG  60
LKPGPEYFVV IQGVKGGDPS FPLSAIFTTG GNHHHHH                           97

SEQ ID NO: 83           moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 83
LPAPKNLVVS RVTEDSARLS WTAPDAAFDS FAITYIEKEH IEDGEAIVLT VPGSERSYDL  60
TGLKPGTEYW VPIWGVKGGA NSWPLSAIFT T                                 91

SEQ ID NO: 84           moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 84
LPAPKNLVVS RVTEDSARLS WTAPDAAFDS FNIAYPEALH PGYGEAIVLT VPGSERSYDL  60
```

```
TGLKPGTEYF VVIYGVKGGT NSEPLSAIFT T                              91

SEQ ID NO: 85           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 85
LPAPKNLVVS RVTEDSARLS WTAPDAAFDS FGILYYEPVD SGEAITLPIP GSERSYDLTG  60
LKPGTEYWVV ITGVKGGAPS TPLGAIFTT                                 89

SEQ ID NO: 86           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 86
LPAPKNLVVS RVTEDSARLS WTTPDAAFDS FGILYYEPVD SGEAITLPVP GSERSYDLTG  60
LKPGTEYWVV ITGVKGGAPS TPLGAIFTT                                 89

SEQ ID NO: 87           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 87
LPAPKNLVVS RVTEDSARLS WTAPDAAFDS FGITYYEPNH GGEAISLSVP GSERSYDPTG  60
LKPGTEYWVV ITGVKGGAPS TPLGAIFTT                                 89

SEQ ID NO: 88           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 88
LSAPKNLVVS RVTEDSARLS WTAPDAAFDS FGILYYEPVD SGEAITLPIP GSERSYDLTG  60
LKPGTEYWVV ITGVKGGAPS TPLGAIFTT                                 89

SEQ ID NO: 89           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 89
LPAPKNLVVS RVTEDSARLS WTAPDAAFDS FGILYYEPVD SGEAITLPVP GSERSYDLTG  60
LKPGTEYWVV ITGVKGGAPS TPLGTIFTT                                 89

SEQ ID NO: 90           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 90
LPAPKNLVVS RVTEDSARLS WTAPDAAFDS FGILYYEPVD SGEAITLPVP GSERSYDLTG  60
LKPGTEYFVI IVGVKGGYPS IPLGAAFTT                                 89

SEQ ID NO: 91           moltype = AA  length = 89
FEATURE                 Location/Qualifiers
REGION                  1..89
                        note = Description of Artificial Sequence: Synthetic
                         polypeptide
```

```
source                  1..89
                        mol_type = protein
                        organism = synthetic construct
SEQUENCE: 91
LPAPKNLVVS RVTEDSARLS WTAPDAAFDS FGILYYEPVD SGEAITLPVL GSERSYDLTG  60
LKPGTEYWVV ITGVKGGAPS TPLGAIFTT                                   89

SEQ ID NO: 92           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 92
LPAPKNLVVS RVTEDSARLS WIAPDAAFDS FSIAYVEAEL VGEAIQLVVP GSERSYDLTG  60
LKPGTEYWVV ILGVKGGNPS NPLGASFTT                                   89

SEQ ID NO: 93           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 93
LPAPKNLVVS RVTEDSARLS WTAPDAAFDS FAIWYVEQHP FGEAIPLFVP GSERSYDLTG  60
LKPGTEYTVG IRGVKGGNFS TPLIAHFTT                                   89

SEQ ID NO: 94           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 94
LPAPKNLVVS RVTEDSARLS WTAPDAAFDS FGILYYEPVD SGEAITLPVP GSERSYDLTG  60
LKPGTEYWVV ITGVKGGAPS TPLGAILTT                                   89

SEQ ID NO: 95           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 95
LPAPKNLVVS RVTEDSARLS WTAPDAAFDS FEIYYPEWPF AGEAIGLPVP GSERSYDLTG  60
LKPGTEYFVV IYGVKGGELS EPLTAQFTT                                   89

SEQ ID NO: 96           moltype = AA  length = 90
FEATURE                 Location/Qualifiers
REGION                  1..90
                        note = Description of Artificial Sequence: Synthetic
                         polypeptide
source                  1..90
                        mol_type = protein
                        organism = synthetic construct
SEQUENCE: 96
LPAPKNLVVS RVTEDSARLS WTAPDAAFDS FSIAYVEAEL VGEAIQLVVP GSERSYDLTG  60
LKPGTEYWVV ILGVKGGNPS NPLGASFTTT                                  90

SEQ ID NO: 97           moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 97
LPAPKNLVVS RVTEDSARLS WTAPDAAFDS FSIAYVEAEL VGEAIQLVVP GSERSYDLTG  60
LKPGTEYWVV ILGVKGGNPS NPLGASFTT                                   89
```

-continued

```
SEQ ID NO: 98          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 98
LPAPKNLVVS RVTEDSARLS WTAPDAAFDS FDIWYAEYGY PGEAIVLTVP GSERSYDLTG  60
LKPGTEYDVA IVGVKGGNRS YPLSAIFTT                                    89

SEQ ID NO: 99          moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 99
LPAPKNLVVS RVTEDSARLS WTAPDAAFDS FGILYYEPVD SGEAITLPVP GSERSYDLTG  60
LKPGTEYWVV ITGVKGGAPS TPLGAIFTT                                    89

SEQ ID NO: 100         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 100
LPAPKNLVVS RVTEDSARLS WTAPDAAFDS FGIWYHEYGG DGEAIVLTVP GSERSYDLTG  60
LKPGTEYDVA IWGVKGGDVS YPLSAIFTT                                    89

SEQ ID NO: 101         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 101
LPAPKNLVVS RVTEDSARLS WTAPDAAFDS FDIWYAEYGY PGEAIVLTVP GSERSYDLTG  60
LNPGTEYDVA ISGVKGGPRS YPLSAIFTT                                    89

SEQ ID NO: 102         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 102
LPAPKNLVVS RVTEDSARLS WTAPDAAFDS LGITYWESPY AGEAIVLTVP GSERSYDLTG  60
LKPGTEYGVF ILGVKGGYPS APLSAIFTT                                    89

SEQ ID NO: 103         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 103
LPAPKNLVVS RVTEDSARLS WTAPDAAFDS FGIWYAEYGY SGEAIVLTVP GSERSYDLTG  60
LKPGTEYDVA IWGVKGGVRS YPLSAIFTT                                    89

SEQ ID NO: 104         moltype = AA  length = 89
FEATURE                Location/Qualifiers
REGION                 1..89
                       note = Description of Artificial Sequence: Synthetic
                        polypeptide
source                 1..89
                       mol_type = protein
```

```
                        organism = synthetic construct
SEQUENCE: 104
LPAPKNLVVS RVTEDSARLS WTAPDAAFDS FGIWYREYGG SGEAIVLTVP GSERSYDLTG  60
LKPGTEYDVA IWGVKGGVRS YPLSAIFTT                                   89

SEQ ID NO: 105          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 105
LPAPKNLVVS RVTEDSARLS WTAPDAAFDS FDIWYAEYGY PGEAIVLTVP GSERSYDLTG  60
LKPGTEYDVA ISGIKGGPRS YPLSAIFTT                                   89

SEQ ID NO: 106          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 106
LPAPKNLVVS RVTEDSARLS WTAPDAAFDS FDIWYAEYGY PGEAIVLTVP GSERSYDLTG  60
LKPGTEYDVA ISGAKGGPRS YPLSAIFTT                                   89

SEQ ID NO: 107          moltype = AA  length = 88
FEATURE                 Location/Qualifiers
REGION                  1..88
                        note = Description of Artificial Sequence: Synthetic
                         polypeptide
source                  1..88
                        mol_type = protein
                        organism = synthetic construct
SEQUENCE: 107
LPAPKNLVVS RVTEDSARLS WTAPDAAFDS FPIWYREYAT GEAIVLTVPG SERSYDLTGL  60
KPGTEYDVVI TGVKGGYPSY PLSAIFTT                                    88

SEQ ID NO: 108          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 108
LPAPKNLVVS RVTEDSARLS WTAPDAAFDS FGITYWESPY AGEAIVLTVP GSERSYDLTG  60
LKPGTEYGVF ILGVKGGYPS APLSAIFTT                                   89

SEQ ID NO: 109          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 109
LPAPKNLVVS RVTEDSARLS WTAPDAAFDS FGIWYAEYGY SGEAIVLTVP GSERSYDLTG  60
LKPGTEYDVA IYGVKGGSPS YPLSAIFTT                                   89

SEQ ID NO: 110          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 110
LPAPKNLVVS RVTEDSARLS WTAPDAAFDS FDIWYAEYGY PGEAIVLTVP GSERSYDLTG  60
LKPGTEYDVA ISGVKGGPRS YPLSAIFTT                                   89

SEQ ID NO: 111          moltype = AA  length = 96
FEATURE                 Location/Qualifiers
```

```
REGION                  1..96
                        note = Description of Artificial Sequence: Synthetic
                         polypeptide
source                  1..96
                        mol_type = protein
                        organism = synthetic construct
SEQUENCE: 111
LPAPKNLVVS RVTEDSARLS WKRIDSPFDS FLIQYQESEK VGEAIVLTVP GSERSYDLTG  60
LKPGTEYTVS IYGVDVKYDI DSRPISSNPL SAIFTT                            96

SEQ ID NO: 112          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 112
LPAPKNLVVS RVTEDSARLS WIGHDSGFDS FLIQYQESEK VGEAIVLTVP GSERSYDLTG  60
LKPGTEYTVS IYGVDVKYDI DSRPISSNPL SAIFTT                            96

SEQ ID NO: 113          moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 113
LPAPKNLVVS RVTEDSARLS WKRRWDSFDS FLIQYQESEK VGEAIVLTVP GSERSYDLTG  60
LKPGTEYTVS IYGVDVEWFN GLPHHSNPLS AIFTT                             95

SEQ ID NO: 114          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 114
LPAPKNLVVS RVTEDSARLS WAKHPNSFDS FLIQYQESEK VGEAIVLTVP GSERSYDLTG  60
LKPGTEYTVS IYGVDVVVNE LNNPLFSNPL SAIFTT                            96

SEQ ID NO: 115          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 115
LPAPKNLVVS RVTEDSARLS WWTSPLPFDS FLIQYQESEK VGEAIVLTVP GSERSYDLTG  60
LKPGTEYTVS IYGVDVKYDI DSRPISSNPL SAIFTT                            96

SEQ ID NO: 116          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 116
LPAPKNLVVS RVTEDSARLS WAKNLHSFDS FLIQYQESEK VGEAIVLTVP GSERSYDLTG  60
LKPGTEYTVS IYGVDVKYDI DSRPISSNPL SAIFTT                            96

SEQ ID NO: 117          moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 117
```

-continued

```
LPAPKNLVVS RVTEDSARLS WYPSDPPFDS FLIQYQESEK VGEAIVLTVP GSERSYDLTG  60
LKPGTEYTVS IYGVPNYHSR RSYYYSNPLS AIFTT                             95

SEQ ID NO: 118         moltype = AA  length = 95
FEATURE                Location/Qualifiers
REGION                 1..95
                       note = Description of Artificial Sequence: Synthetic
                        polypeptide
source                 1..95
                       mol_type = protein
                       organism = synthetic construct
SEQUENCE: 118
LPAPKNLVVS RVTEDSARLS WVKRATSFDS FLIQYQESEK VGEAIVLTVP GSERSYDLTG  60
LKPGTEYTVS IYGVDVRYNE GQPIWSNPLS AIFTT                             95

SEQ ID NO: 119         moltype = AA  length = 97
FEATURE                Location/Qualifiers
REGION                 1..97
                       note = Description of Artificial Sequence: Synthetic
                        polypeptide
source                 1..97
                       mol_type = protein
                       organism = synthetic construct
SEQUENCE: 119
LPAPKNLVVS RVTEDSARLS WQRPKSGFFD SFLIQYQESE KVGEAIVLTV PGSERSYDLT  60
GLKPGTEYTV SIYGVDVKYD IDSRPISSNP LSAIFTT                           97

SEQ ID NO: 120         moltype = AA  length = 96
FEATURE                Location/Qualifiers
REGION                 1..96
                       note = Description of Artificial Sequence: Synthetic
                        polypeptide
source                 1..96
                       mol_type = protein
                       organism = synthetic construct
SEQUENCE: 120
LPAPKNLVVS RVTEDSARLS WPVESNAFDS FLIQYQESEK VGEAIVLTVP GSERSYDLTG  60
LKPGTEYTVS IYGVDVEYDQ HGRPRWSNPL SAIFTT                            96

SEQ ID NO: 121         moltype = AA  length = 96
FEATURE                Location/Qualifiers
REGION                 1..96
                       note = Description of Artificial Sequence: Synthetic
                        polypeptide
source                 1..96
                       mol_type = protein
                       organism = synthetic construct
SEQUENCE: 121
LPAPKNLVVS RVTEDSARLS WVREHDSFDS FLIQYQESEK VGEAIVLTVP GSERSYDLTG  60
LKPGTEYTVS IYGVDVKYDI DSRPISSNPL SAIFTT                            96

SEQ ID NO: 122         moltype = AA  length = 96
FEATURE                Location/Qualifiers
REGION                 1..96
                       note = Description of Artificial Sequence: Synthetic
                        polypeptide
source                 1..96
                       mol_type = protein
                       organism = synthetic construct
SEQUENCE: 122
LPAPKNLVVS RVTEDSARLS WAKRPGAFDS FLIQYQESEK VGEAIVLTVP GSERSYDLTG  60
LKPGTEYTVS IYGVDVKYDI DSRPISSNPL SAIFTT                            96

SEQ ID NO: 123         moltype = AA  length = 96
FEATURE                Location/Qualifiers
REGION                 1..96
                       note = Description of Artificial Sequence: Synthetic
                        polypeptide
source                 1..96
                       mol_type = protein
                       organism = synthetic construct
SEQUENCE: 123
LPAPKNLVVS RVTEDSARLS WVKRATSFDS FLIQYQESEK VGEAIVLTVP GSERSYDLTG  60
LKPGTEYTVS IYGVDVKYDI DSRPISSNPL SAIFTT                            96

SEQ ID NO: 124         moltype = AA  length = 96
FEATURE                Location/Qualifiers
REGION                 1..96
                       note = Description of Artificial Sequence: Synthetic
```

```
                         polypeptide
source                  1..96
                        mol_type = protein
                        organism = synthetic construct
SEQUENCE: 124
LPAPKNLVVS RVTEDSARLS WVPSPWGFDS FLIQYQESEK VGEAIVLTVP GSERSYDLTG  60
LKPGTEYTVS IYGVDVKYDI DSRPISSNPL SAIFTT                            96

SEQ ID NO: 125          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 125
LPAPKNLVVS RVTEDSARLS WARNITSFDS FLIQYQESEK VGEAIVLTVP GSERSYDLTG  60
LKPGTEYTVS IYGVDVKYDI DSRPISSNPL SAIFTT                            96

SEQ ID NO: 126          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 126
LPAPKNLVVS RVTEDSARLS WRKKDHPFDS FLIQYQESEK VGEAIVLTVP GSERSYDLTG  60
LKPGTEYTVS IYGVDVKYDI DSRPISSNPL SAIFTT                            96

SEQ ID NO: 127          moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 127
LPAPKNLVVS RVTEDSARLS WGYYHGHFDS FLIQYQESEK VGEAIVLTVP GSERSYDLTG  60
LKPGTEYTVS IYGVDVKWEG NRPVASNPLS AIFTT                             95

SEQ ID NO: 128          moltype = AA  length = 96
FEATURE                 Location/Qualifiers
REGION                  1..96
                        note = Description of Artificial Sequence: Synthetic
                         polypeptide
source                  1..96
                        mol_type = protein
                        organism = synthetic construct
SEQUENCE: 128
LPAPKNLVVS RVTEDSARLS WRKEATSFDS FLIQYQESEK VGEAIVLTVP GSERSYDLTG  60
LKPGTEYTVS IYGVDVKYDI DSRPISSNPL SAIFTT                            96

SEQ ID NO: 129          moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 129
LPAPKNLVVS RVTEDSARLS WVKRATSFDS FLIQYQESEK VGEAIVLTVP GSERSYDLTG  60
LKPGTEYTVS IYGVDVKWEG NRPVASNPLS AIFTT                             95

SEQ ID NO: 130          moltype = AA  length = 97
FEATURE                 Location/Qualifiers
REGION                  1..97
                        note = Description of Artificial Sequence: Synthetic
                         polypeptide
source                  1..97
                        mol_type = protein
                        organism = synthetic construct
SEQUENCE: 130
LPAPKNLVVS RVTEDSARLS WPKIQGQHFD SFLIQYQESE KVGEAIVLTV PGSERSYDLT  60
GLKPGTEYTV SIYGVDVKYD IDSRPISSNP LSAIFTT                           97
```

```
SEQ ID NO: 131         moltype = AA  length = 99
FEATURE                Location/Qualifiers
REGION                 1..99
                       note = Description of Artificial Sequence: Synthetic
                        polypeptide
source                 1..99
                       mol_type = protein
                       organism = synthetic construct
SEQUENCE: 131
LPAPKNLVVS RVTEDSARLS WQRADDILPY FDSFLIQYQE SEKVGEAIVL TVPGSERSYD  60
LTGLKPGTEY TVSIYGVDVK YDIDSRPISS NPLSAIFTT                        99

SEQ ID NO: 132         moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 132
LPAPKNLVVS RVTEDSARLS WVRSDTARFF DSFLIQYQES EKVGEAIVLT VPGSERSYDL  60
TGLKPGTEYT VSIYGVDVKY DIDSRPISSN PLSAIFTT                         98

SEQ ID NO: 133         moltype = AA  length = 99
FEATURE                Location/Qualifiers
REGION                 1..99
                       note = Description of Artificial Sequence: Synthetic
                        polypeptide
source                 1..99
                       mol_type = protein
                       organism = synthetic construct
SEQUENCE: 133
LPAPKNLVVS RVTEDSARLS WASTVDPHPR FDSFLIQYQE SEKVGEAIVL TVPGSERSYD  60
LTGLKPGTEY TVSIYGVDVK YDIDSRPISS NPLSAIFTT                        99

SEQ ID NO: 134         moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 134
LPAPKNLVVS RVTEDSARLS WQRHSDAHPL FDSFLIQYQE SEKVGEAIVL TVPGSERSYD  60
LTGLKPGTEY TVSIYGVDVK WEGNRPVASN PLSAIFTT                         98

SEQ ID NO: 135         moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 135
LPAPKNLVVS RVTEDSARLS WPIVNTPLHF DSFLIQYQES EKVGEAIVLT VPGSERSYDL  60
TGLKPGTEYT VSIYGVDVQY TATGQPERSN PLSAIFTT                         98

SEQ ID NO: 136         moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 136
LPAPKNLVVS RVTEDSARLS WAKTSDLHPL FDSFLIQYQE SEKVGEAIVL TVPGSERSYD  60
LTGLKPGTEY TVSIYGVDVK WEGNRPVASN PLSAIFTT                         98

SEQ ID NO: 137         moltype = AA  length = 98
FEATURE                Location/Qualifiers
REGION                 1..98
                       note = Description of Artificial Sequence: Synthetic
                        polypeptide
source                 1..98
```

```
                         mol_type = protein
                         organism = synthetic construct
SEQUENCE: 137
LPAPKNLVVS RVTEDSARLS WNKKHDGQPT FDSFLIQYQE SEKVGEAIVL TVPGSERSYD  60
LTGLKPGTEY TVSIYGVDVV YEGSYPASSN PLSAIFTT                          98

SEQ ID NO: 138           moltype = AA  length = 98
FEATURE                  Location/Qualifiers
REGION                   1..98
                         note = Description of Artificial Sequence: Synthetic
                          polypeptide
source                   1..98
                         mol_type = protein
                         organism = synthetic construct
SEQUENCE: 138
LPAPKNLVVS RVTEDSARLS WIKSETSQPA FDSFLIQYQE SEKVGEAIVL TVPGSERSYD  60
LTGLKPGTEY TVSIYGVDVK WEGNRPVASN PLSAIFTT                          98

SEQ ID NO: 139           moltype = AA  length = 97
FEATURE                  Location/Qualifiers
REGION                   1..97
                         note = Description of Artificial Sequence: Synthetic
                          polypeptide
source                   1..97
                         mol_type = protein
                         organism = synthetic construct
SEQUENCE: 139
LPAPKNLVVS RVTEDSARLS WYARKFISPF DSFLIQYQES EKVGEAIVLT VPGSERSYDL  60
TGLKPGTEYT VSIYGVDVKW EGNRPVASNP LSAIFTT                           97

SEQ ID NO: 140           moltype = AA  length = 99
FEATURE                  Location/Qualifiers
REGION                   1..99
                         note = Description of Artificial Sequence: Synthetic
                          polypeptide
source                   1..99
                         mol_type = protein
                         organism = synthetic construct
SEQUENCE: 140
LPAPKNLVVS RVTEDSARLS WYRPDNRAGA FDSFLIQYQE SEKVGEAIVL TVPGSERSYD  60
LTGLKPGTEY TVSIYGVDVK YDIDSRPISS NPLSAIFTT                         99

SEQ ID NO: 141           moltype = AA  length = 97
FEATURE                  Location/Qualifiers
REGION                   1..97
                         note = Description of Artificial Sequence: Synthetic
                          polypeptide
source                   1..97
                         mol_type = protein
                         organism = synthetic construct
SEQUENCE: 141
LPAPKNLVVS RVTEDSARLS WERIVQTPHF DSFLIQYQES EKVGEAIVLT VPGSERSYDL  60
TGLKPGTEYT VSIYGVDVKW EGNRPVASNP LSAIFTT                           97

SEQ ID NO: 142           moltype = AA  length = 98
FEATURE                  Location/Qualifiers
REGION                   1..98
                         note = Description of Artificial Sequence: Synthetic
                          polypeptide
source                   1..98
                         mol_type = protein
                         organism = synthetic construct
SEQUENCE: 142
LPAPKNLVVS RVTEDSARLS WPEEAVTATS FDSFLIQYQE SEKVGEAIVL TVPGSERSYD  60
LTGLKPGTEY TVSIYGVDVK WEGNRPVASN PLSAIFTT                          98

SEQ ID NO: 143           moltype = AA  length = 97
FEATURE                  Location/Qualifiers
REGION                   1..97
                         note = Description of Artificial Sequence: Synthetic
                          polypeptide
source                   1..97
                         mol_type = protein
                         organism = synthetic construct
SEQUENCE: 143
LPAPKNLVVS RVTEDSARLS WPKNQTNRHF DSFLIQYQES EKVGEAIVLT VPGSERSYDL  60
TGLKPGTEYT VSIYGVDVKW EGNRPVASNP LSAIFTT                           97

SEQ ID NO: 144           moltype = AA  length = 98
```

-continued

```
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 144
LPAPKNLVVS RVTEDSARLS WYRATTPAPH FDSFLIQYQE SEKVGEAIVL TVPGSERSYD  60
LTGLKPGTEY TVSIYGVDVK WEGNRPVASN PLSAIFTT                          98

SEQ ID NO: 145         moltype = AA  length = 97
FEATURE                Location/Qualifiers
REGION                 1..97
                       note = Description of Artificial Sequence: Synthetic
                        polypeptide
source                 1..97
                       mol_type = protein
                       organism = synthetic construct
SEQUENCE: 145
LPAPKNLVVS RVTEDSARLS WSAKKFPRHF DSFLIQYQES EKVGEAIVLT VPGSERSYDL  60
TGLKPGTEYT VSIYGVDVKW EGNRPVASNP LSAIFTT                           97

SEQ ID NO: 146         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 146
LPAPKNLVVS RVTEDSARLS WTAPDAAFDS FYIAYPEWPV QGEAIVLTVP GSERSYDLTG  60
LKPGTEYFVI IYGVKGGDWS EPLSAIFTT                                    89

SEQ ID NO: 147         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 147
LPAPKNLVVS RVTEDSARLS WTAPDAAFDS FRIAYPEWPV RGDAIVLTVP GSERSYDLTG  60
LKPGTEYWVI IQGVKGGTDS FPLSAIFTT                                    89

SEQ ID NO: 148         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 148
LPAPKNLVVS RVTEDSARLS WTAPDAAFDS FYITYPEIPL GGEAIVLTVP GSERSYDLTG  60
LKPGTEYFVV IYGVKGGLLS SPLSAIFTT                                    89

SEQ ID NO: 149         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 149
LPAPKNLVVS RVTEDSARLS WTAPDAAFDS FYISYPEWEQ LGEAIVLTVP GSERSYDLTG  60
LKPGTEYFVV IYGVKGGALS APLSAIFTT                                    89

SEQ ID NO: 150         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
```

```
SEQUENCE: 150
LPAPKNLVVS RVTEDSARLS WTAPDAAFDS FAISYPEWPP PGEAIVLTVP GSERSYDLTG  60
LKPGTEYWVI ILGVKGGDQS WPLSAIFTT                                   89

SEQ ID NO: 151         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 151
LPAPKNLVVS RVTEDSARLS WTAPDAAFDS FQIAYPEWPK DGEAIVLTVP GSERSYDLTG  60
LKPGTEYAVF IWGVKGGVYS NPLSAIFTT                                   89

SEQ ID NO: 152         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 152
LPAPKNLVVS RVTEDSARLS WTAPDAAFDS FDIAYPEWPP KGEAIVLTVP GSERSYDLTG  60
LKPGTEYFVV IYGVKGGIHS APLSAIFTT                                   89

SEQ ID NO: 153         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 153
LPAPKNLVVS RVTEDSARLS WTAPDAAFDS FQIAYPETPI QGEAIVLTVP GSERSYDLTG  60
LKPGTEYFVI IHGVKGGITS FPLSAIFTT                                   89

SEQ ID NO: 154         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 154
LPAPKNLVVS RVTEDSARLS WTAPDAAFDS FGISYPEWPP LGEAIVLTVP GSERSYDLTG  60
LKPGTEYWVI IFGVKGGERS WPLSAIFTT                                   89

SEQ ID NO: 155         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 155
LPAPKNLVVS RVTEDSARLS WTAPDAAFDS FGIAYPELPI GGEAIVLTVP GSERSYDLTG  60
LKPGTEYFVI IRGVKGGTLS PPLSAIFTT                                   89

SEQ ID NO: 156         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 156
LPAPKNLVVS RVTEDSARLS WTAPDAAFDS FWISYPEWPV PGEAIVLTVP GSERSYDLTG  60
LKPGTEYWVI IQGVKGGKLS WPLSAIFTT                                   89

SEQ ID NO: 157         moltype = AA  length = 89
FEATURE                Location/Qualifiers
REGION                 1..89
```

```
                        note = Description of Artificial Sequence: Synthetic
                         polypeptide
source                  1..89
                        mol_type = protein
                        organism = synthetic construct
SEQUENCE: 157
LPAPKNLVVS RVTEDSARLS WTAPDAAFDS FNIAYPEWPV RGEAIVLTVP GSERSYDLTG  60
LKPGTEYWVI IYGVKGGDRS NPLSAIFTT                                    89

SEQ ID NO: 158          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 158
LPAPKNLVVS RVTEDSARLS WTAPDAAFDS FSIAYPEWPV HGEAIVLTVP GSERSYDLTG  60
LKPGTEYFVI IYGVKGGVLS EPLSAIFTT                                    89

SEQ ID NO: 159          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 159
LPAPKNLVVS RVTEDSARLS WTAPDAAFDS FDIAYPEWPT KGEAIVLTVP GSERSYDLTG  60
LKPGTEYFVV INGVKGGWRS FPLSAIFTT                                    89

SEQ ID NO: 160          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 160
LPAPKNLVVS RVTEDSARLS WTAPDAAFDS FWIAYPEWPV PGEAIVLTVP GSERSYDLTG  60
LKPGTEYFVI IQGVKGGFGS FPLSAIFTT                                    89

SEQ ID NO: 161          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 161
LPAPKNLVVS RVTEDSARLS WTAPDAAFDS FTIAYPEREQ DKWGEAIVLT VPGSERSYDL  60
TGLKPGTEYW VIIQGVKGGR PSTPLSAILT T                                 91

SEQ ID NO: 162          moltype = AA  length = 88
FEATURE                 Location/Qualifiers
REGION                  1..88
                        note = Description of Artificial Sequence: Synthetic
                         polypeptide
source                  1..88
                        mol_type = protein
                        organism = synthetic construct
SEQUENCE: 162
LPAPKNLVVS RVTEDSARLS WTAPDAAFDS FAIAYPEWPP GEAIVLTVPG SERSYDLTGL  60
KPGTEYFVII YGVKGGWTSP PLSAIFTT                                     88

SEQ ID NO: 163          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 163
LPAPKNLVVS RVTEDSARLS WTAPDAAFDS FSIAYPEWPG SGEAIVLTVP GSERSYDLTG  60
```

```
LKPGTEYFVV IFGVKGGSQS WPLSAIFTT                                    89

SEQ ID NO: 164          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 164
LPAPKNLVVS RVTEDSARLS WTAPDAAFDS FGIWYPEWPV GGEAIVLTVP GSERSYDLTG  60
LKPGTEYWVN ISGVKGGEYS FPLSAIFTT                                    89

SEQ ID NO: 165          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 165
LPAPKNLVVS RVTEDSARLS WTAPDAAFDS FQISYPEWPV HGEAIVLTVP GSERSYDLTG  60
LKPGTEYWVI IWGVKGGRQS WPLSAIFTT                                    89

SEQ ID NO: 166          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 166
LPAPKNLVVS RVTEDSARLS WTAPDAAFDS FDIAYPELPL GGEAIVLTVP GSERSYDLTG  60
LKPGTEYFVI IWGVKGGDRS EPLSAIFTT                                    89

SEQ ID NO: 167          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 167
LPAPKNLVVS RVTEDSARLS WTAPDAAFDS FIIAYPETPV RGEAIVLTVP GSERSYDLTG  60
LKPGTEYFVI IIGVKGGQES FPLSAIFTT                                    89

SEQ ID NO: 168          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 168
LPAPKNLVVS RVTEDSARLS WTAPDAAFDS FSISYIEYPE IPGGEAIVLT VPGSERSYDL  60
TGLKPGTEYW VPIWGVKGGI QSWPLSAIFT T                                 91

SEQ ID NO: 169          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 169
LPAPKNLVVS RVTEDSARLS WTAPDAAFDS FGIAYVEWWH RGEAISLPVP GSERSYDLTG  60
LKPGTEYNVI ITGVKGGIPS HPLGAIFTT                                    89

SEQ ID NO: 170          moltype = AA  length = 89
FEATURE                 Location/Qualifiers
REGION                  1..89
                        note = Description of Artificial Sequence: Synthetic
                         polypeptide
```

```
source                  1..89
                        mol_type = protein
                        organism = synthetic construct
SEQUENCE: 170
LPAPKNLVVS RVTEDSARLS WTAPDAAFDS FYIPYWESEV YGEAIALPVP GSERSYDLTG  60
LKPGTEYQVS IIGVKGGVYS QPLAAIFTT                                    89

SEQ ID NO: 171          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 171
LPAPKNLVVS RVTEDSARLS WTAPDAAFDS FGIGYAEPVV TGEAISLSVP GSERSYDLTG  60
LKPGTEYWVV IIGVKGGINS YPLGAIFTT                                    89

SEQ ID NO: 172          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 172
LPAPKNLVVS RVTEDSARLS WTAPDAAFDS FYIPYWESEV YGEAIALPVT GSERSYDLTG  60
LKPGTEYQVS IIGVKGGVYS QPLAAIFTT                                    89

SEQ ID NO: 173          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 173
LPAPKNLVVS RVTEDSARLS WTAPDAAFDS FYIPYRESEF RGEAIALPVP GSERSYDLTG  60
LKPGTKYRVI IIGVKGGEFS QPLAAIFTT                                    89

SEQ ID NO: 174          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 174
LPAPKNLVVS RVTEDSARLS WTAPDAAFDS FYIPYRESEF RGEAIALPVP GSERSYDLTG  60
LKPGTKYSVI IIGVKGGEFS QPLGAIFTT                                    89

SEQ ID NO: 175          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 175
LPAPKNLVVS RVTEDSARLS WTAPDAAFDS FYIPYRESEF RGEAIALSVP GSERSYDLTG  60
LKPGTKYRVI IIGVKGGEFS QPLGAIFTT                                    89

SEQ ID NO: 176          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 176
LPAPKNLVVS RVTEDSARLS WTAPDAAFDS FGISYYEWAP NGEAIQLSVP GSERSYDLTG  60
LKPGTEYHVV IIGVKGGEPS HPLGAIFTT                                    89
```

```
SEQ ID NO: 177          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 177
LPAPKNLVVS RVTEDSARLS WTAPDAAFDS FYIPYRESEF RGEAIALPVP GSERSYDLTG  60
LKPGTKYRVI IIGVKGGEFS QPLSAIFTT                                    89

SEQ ID NO: 178          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 178
LPAPKNLVVS RVTEDSARLS WTAPDAAFDS FWITYPEWPV PGEAIVLTVP GSERSYDLTG  60
LKPGTEYAVF IWGVKGGDAS EPLSAIFTT                                    89

SEQ ID NO: 179          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 179
LPAPKNLVVS RVTEDSARLS WTAPDAAFDS FWIAYPEWPT RGEAIVLTVP GSERSYDLTG  60
LKPGTEYFVV IYGVKGGSPS PPLSAIFTT                                    89

SEQ ID NO: 180          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 180
LPAPKNLVVS RVTEDSARLS WTAPDAAFDS FNIAYGEYPG PGEAIVLTVP GSERSYDLTG  60
LKPGTEYWVP IWGVKGGELS EPLSAIFTT                                    89

SEQ ID NO: 181          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 181
LPAPKNLVVS RVTEDSARLS WTAPDAAFDS FWITYPEWPV NGEAIVLTVP GSERSYDLTG  60
LKPGTEYWVV IWGVKGGVES PPLSAIFTT                                    89

SEQ ID NO: 182          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 182
LPAPKNLVVS RVTEDSARLS WTAPDAAFDS FKISYPEWPP EGEAIVLTVP GSERSYDLTG  60
LKPGTEYAVF IWCVKGGEHS WPLSAIFTT                                    89

SEQ ID NO: 183          moltype = AA  length = 89
FEATURE                 Location/Qualifiers
REGION                  1..89
                        note = Description of Artificial Sequence: Synthetic
                         polypeptide
source                  1..89
                        mol_type = protein
```

```
                         organism = synthetic construct
SEQUENCE: 183
LPAPKNLVVS RVTEDSARLS WTAPDAAFDS FKIAYPEWPD GGEAIVLTVP GSERSYDLTG  60
LKPGTEYFVI IYGVKGGILS PPLSAIFTT                                   89

SEQ ID NO: 184           moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 184
LPAPKNLVVS RVTEDSARLS WTAPDAAFDS FNIAYPEWPV RGEAIVLTVP GSERSYDLTG  60
LKPGTEYWVI IIGVKGGEDS WPLSAIFTT                                   89

SEQ ID NO: 185           moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 185
LPAPKNLVVS RVTEDSARLS WTAPDAAFDS FSIAYPEWPV YGEAIVLTVP GSERSYDLTG  60
LKPGTEYFVV IYGVKGGNYS DPLSAIFTT                                   89

SEQ ID NO: 186           moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 186
LPAPKNLVVS RVTEDSARLS WTAPDAAFDS FDIAYPEWPL GGEAIVLTVP GSERSYDLTG  60
LKPGTEYWVI ILGVKGGDQS WPLSAIFTT                                   89

SEQ ID NO: 187           moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 187
LPAPKNLVVS RVTEDSARLS WTAPDAAFDS FNIFYPELVF PGEAIVLTVP GSERSYDLTG  60
LKPGTEYWVN ISGVKGGEHS WPLSAIFTT                                   89

SEQ ID NO: 188           moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 188
LPAPKNLVVS RVTEDSARLS WTAPDAAFDS FSIAYPELPV KGEAIVLTVP GSERSYDLTG  60
LKPGTEYFVV IWGVKGGTYS GPLSAIFTT                                   89

SEQ ID NO: 189           moltype = AA  length = 89
FEATURE                  Location/Qualifiers
REGION                   1..89
                         note = Description of Artificial Sequence: Synthetic
                          polypeptide
source                   1..89
                         mol_type = protein
                         organism = synthetic construct
SEQUENCE: 189
LPAPKNLVVS RVTEDSARLS WTAPDAAFDS FEIAYPEIPI AGEAIVLTVP GSERSYDLTG  60
LKPGTEYFVI IYGVKGGDWS DPLSAIFTT                                   89

SEQ ID NO: 190           moltype = AA  length = 89
FEATURE                  Location/Qualifiers
```

```
REGION                  1..89
                        note = Description of Artificial Sequence: Synthetic
                         polypeptide
source                  1..89
                        mol_type = protein
                        organism = synthetic construct
SEQUENCE: 190
LPAPKNLVVS RVTEDSARLS WTAPDAAFDS FDIAYPEWPV PGEAIVLTVP GSERSYDLTG  60
LKPGTEYWVI IKGVKGGNIS WPLSAIFTT                                    89

SEQ ID NO: 191          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 191
LPAPKNLVVS RVTEDSARLS WTAPDAAFDS FDIGYPEWPI KGEAIVLTVP GSERSYDLTG  60
LKPGTEYWVI IWGVKGGDRS EPLSAIFTT                                    89

SEQ ID NO: 192          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 192
LPAPKNLVVS RVTEDSARLS WTAPDAAFDS FAIAYPEIAK WGEAIVLTVP GSERSYDLTG  60
LKPGTEYFVI IYGVKGGVHS FPLSAIFTT                                    89

SEQ ID NO: 193          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 193
LPAPKNLVVS RVTEDSARLS WTAPDAAFDS FHIFYPELPI AGEAIVLTVP GSERSYDLTG  60
LKPGTEYWVN ISGVKGGYES WPLSAIFTT                                    89

SEQ ID NO: 194          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 194
LPAPKNLVVS RVTEDSARLS WTAPDAAFDS FYISYPELPV EGEAIVLTVP GSERSYDLTG  60
LKPGTEYWVI IWGVKGGATS EPLSAIFTT                                    89

SEQ ID NO: 195          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 195
LPAPKNLVVS RVTEDSARLS WTAPDAAFDS FQIAYPEYPA LGEAIVLTVP GSERSYDLTG  60
LKPGTEYFVI IIGVKGGDES FPLSAIFTT                                    89

SEQ ID NO: 196          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 196
```

-continued

```
LPAPKNLVVS RVTEDSARLS WTAPDAAFDS FDIAYPELPI GGEAIVLTVP GSERSYDLTG  60
LKPGTEYFVV IYGVKGGIHS APLSAIFTT                                    89

SEQ ID NO: 197         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 197
LPAPKNLVVS RVTEDSARLS WTAPDAAFDS FNIAYPEWPP EGEAIVLTVP GSERSYDLTG  60
LKPGTEYFVV IYGVKGGHLS DPLSAIFTT                                    89

SEQ ID NO: 198         moltype = AA  length = 88
FEATURE                Location/Qualifiers
REGION                 1..88
                       note = Description of Artificial Sequence: Synthetic
                        polypeptide
source                 1..88
                       mol_type = protein
                       organism = synthetic construct
SEQUENCE: 198
LPAPKNLVVS RVTEDSARLS WTAPDAAFDS FQIQYLETAP DGEAIVLTVP GSERSYDLTG  60
LKPGTEYYVW IPGVKGGAFS PLSAIFTT                                     88

SEQ ID NO: 199         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 199
LPAPKNLVVS RVTEDSARLS WTAPDAAFDS FAIAYPEWPI KGEAIVLTVP GSERSYDLTG  60
LKPGTEYWVV IYGVKGGVFS EPLSAIFTT                                    89

SEQ ID NO: 200         moltype = AA  length = 87
FEATURE                Location/Qualifiers
REGION                 1..87
                       note = Description of Artificial Sequence: Synthetic
                        polypeptide
source                 1..87
                       mol_type = protein
                       organism = synthetic construct
SEQUENCE: 200
LPAPKNLVVS RVTEDSARLS WTAPDAAFDS FIYIENKVNG EAIVLTVPGS ERSYDLTGLK  60
PGTEYHVTIG GVKGGTESNT LSAIFTT                                      87

SEQ ID NO: 201         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 201
LPAPKNLVVS RVTEDSARLS WTAPDAAFDS FDIAYPEWPV TGEAIVLTVP GSERSYDLTG  60
LKPGTEYWVI IFGVKGGERS WPLSAIFTT                                    89

SEQ ID NO: 202         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 202
LPAPKNLVVS RVTEDSARLS WTAPDAAFDS FQIAYPEYPA LGEAIVLTVP GSERSYDLTG  60
LKPGTEYFVI IAGVKGGIQS WPLSAIFTT                                    89

SEQ ID NO: 203         moltype = AA  length = 89
FEATURE                Location/Qualifiers
REGION                 1..89
                       note = Description of Artificial Sequence: Synthetic
```

```
                         polypeptide
source                  1..89
                        mol_type = protein
                        organism = synthetic construct
SEQUENCE: 203
LPAPKNLVVS RVTEDSARLS WTAPDAAFDS FYISYPEWPG SGEAIVLTVP GSERSYDLTG  60
LKPGTEYAVF IWCVKGGWLS DPLSAIFTT                                    89

SEQ ID NO: 204          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 204
LPAPKNLVVS RVTEDSARLS WTAPDAAFDS FEIAYPEWPV NGEAIVLTVP GSERSYDLTG  60
LKPGTEYWVV IWGVKGGVNS YPLSAIFTT                                    89

SEQ ID NO: 205          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 205
LPAPKNLVVS RVTEDSARLS WTAPDAAFDS FDIAYPEWPT DGEAIVLTVP GSERSYDLTG  60
LKPGTEYFVI IYGVKGGSYS EPLSAIFTT                                    89

SEQ ID NO: 206          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 206
LPAPKNLVVS RVTEDSARLS WTAPDAAFDS FSILYYELPP SGEAIVLTVP GSERSYDLTG  60
LKPGTEYTVS IFGVKGGDNS FPLSAIFTT                                    89

SEQ ID NO: 207          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 207
LPAPKNLVVS RVTEDSARLS WTAPDAAFDS FDIAYPEWPT DGEAIVLTVP GSERSYDLTG  60
LKPGTEYFVV IYGVKGGHWS YPLSAIFTT                                    89

SEQ ID NO: 208          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 208
LPAPKNLVVS RVTEDSARLS WTAPDAAFDS FEIWYHEYHP RGEAIVLTVP SSERSYDLTG  60
LKPGTEYDVV ISGVKGGHWS YPLSAIFTT                                    89

SEQ ID NO: 209          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 209
LPAPKNLVVS RVTEDSARLS WTAPDAAFDS FLIGYPEWPL GGEAIVLTVP GSERSYDLTG  60
LKPGTEYWVI IYGVKGGEYS DPLSAIFTT                                    89
```

```
SEQ ID NO: 210          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 210
LPAPKNLVVS RVTEDSARLS WTAPDAAFDS FEIWYHEYHP RGEAIVLTVP GSERSYDLTG  60
LKPGTEYDVV ISGVKGGHWS YPLSAIFTT                                   89

SEQ ID NO: 211          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 211
LPAPKNLVVS RVTEDSARLS WTAPDAAFDS FDIAYPEWPT DGEAIVLTVP GSERSYDLTG  60
LKPGTEYFVI IYGVKGGALS RPLSAIFTT                                   89

SEQ ID NO: 212          moltype = AA  length = 95
FEATURE                 Location/Qualifiers
REGION                  1..95
                        note = Description of Artificial Sequence: Synthetic
                         polypeptide
source                  1..95
                        mol_type = protein
                        organism = synthetic construct
SEQUENCE: 212
LPAPKNLVVS RVTEDSARLS WTAPDAAFDS FYIAYPEYVW GGEATSLGEA IVLTVPGSER  60
SYDLTGLKPG TEYFVVITGV KGGLGSYPLS AIFTT                             95

SEQ ID NO: 213          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 213
LPAPKNLVVS RVTEDSARLS WTAPDAAFDS FDIAYPEWPT DGEAIVLTVP GSERSYDLTG  60
LKPGTEYFVV IYGVKGGGRS YPLSAIFTT                                   89

SEQ ID NO: 214          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 214
LPAPKNLVVS RVTEDSARLS WTAPDAAFDS FSINYWEEDP AGEAIVLTVP GSERSYDLTG  60
LKPGTEYRVL IGGVKGGHGS LPLSAIFTT                                   89

SEQ ID NO: 215          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 215
LPAPKNLVVS RVTEDSARLS WTAPDAAFDS FDIAYPEWPT DGEAIVLTVP GSERSYDLTG  60
LKPGTEYFVV IYGVKGGGRS APLSAIFTT                                   89

SEQ ID NO: 216          moltype = AA  length = 89
FEATURE                 Location/Qualifiers
REGION                  1..89
                        note = Description of Artificial Sequence: Synthetic
                         polypeptide
source                  1..89
```

```
                        mol_type = protein
                        organism = synthetic construct
SEQUENCE: 216
LPAPKNLVVS RVTEDSARLS WTAPDAAFDS FWIFYLEPFP RGEAIPLEVP GSERSYDLTG  60
LKPGTEYSVD IRGVKGGDHS DPLWAYFTT                                    89

SEQ ID NO: 217          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 217
LPAPKNLVVS RVTEDSARLS WTAPDAAFDS FGIGYVEFTR AGEAISLSVP GSERSYDLTG  60
LKPGTEYHVV IIGVKGGEPS HPLGAPFTT                                    89

SEQ ID NO: 218          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 218
LPAPKNLVVS RVTEDSARLS WTAPDAAFDS FGIGYAEPAV TGEAISLSVP GSKRSYDLTG  60
LKPGTEYWVV IIGVKGGINS YPLGASFTT                                    89

SEQ ID NO: 219          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 219
LPAPKNLVVS RVTEDSARLS WTAPDAAFDS FGISYYEWAP NGEAIQLSVP GSERSYDLTG  60
LKPGTEYHVV IIGVKGGEPS HPLGAPFTT                                    89

SEQ ID NO: 220          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 220
LPAPKNLVVS RVTEDSARLS WTAPDAAFNS FGIGYAEPAV TGEAISLSVP GSERSYDLTG  60
LKPGTEYWVV IIGVKGGINS YPLGASFTT                                    89

SEQ ID NO: 221          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 221
LPAPKNLVVS RVTEDSARLS WTAPDAAFDS FAIWCVEPIP EGEAIPLFVP GSERSYDLTG  60
LKPGTEYRVG IRGVKGGTFS SPLAAPFTT                                    89

SEQ ID NO: 222          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 222
LPAPKNLVVS RVTEDSARLS WTAPDAAFDS FYIPYRESEF RGEAIALPVP GSERSYDLTG  60
LKPGTKYRVI IIGVKGGEFS QPLGAIFTT                                    89

SEQ ID NO: 223          moltype = AA  length = 89
```

-continued

```
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 223
LPAPKNLVVS RVTEDSARLS WTAPDAAFDS FGIGYIEWVH RGEAISLHVP GSERSYDLTG  60
LKPGTEYVVA IVGVKGGEPS TPLGAPFTT                                   89

SEQ ID NO: 224         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 224
LPAPKNLVVS RVTEDSARLS WTAPDAAFDS FLITYWEIEP EGEAIFLGVP GSERSYDLTG  60
LKPGTEYRVQ INGVKGGTIS YPLFAGFTT                                   89

SEQ ID NO: 225         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 225
LPAPKNLVVS RVTEDSARLS WTAPDAAFDS FGIAYVEWWH RGEAISLPVP GSERSYDLTG  60
LKPGTEYWVT ILGVKGGIIS TPLGASFTT                                   89

SEQ ID NO: 226         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 226
LPAPKNLVVS RVTEDSARLS WTAPDAAFDS FGIGYAEPAV TGEAISLSVP GSERSYDLTG  60
LKPGTEYWVV IIGVKGGINS YPLGASFTT                                   89

SEQ ID NO: 227         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 227
LPAPKNLVVS RVTEDSARLS WTAPDAAFDS FGIAYIETAR WGEAISLTVP GSERSYDLTG  60
LKPGTEYNVV IIGVKGGTPS HPLGAPFTT                                   89

SEQ ID NO: 228         moltype = AA  length = 88
FEATURE                Location/Qualifiers
REGION                 1..88
                       note = Description of Artificial Sequence: Synthetic
                        polypeptide
source                 1..88
                       mol_type = protein
                       organism = synthetic construct
SEQUENCE: 228
LPAPKNLVVS RVTEDSARLS WTAPDAAFDS FGITYLDPRN GEAISLNVPG SERSYDLTGL  60
KPGTEYWVVI IGVKGGINSY PLGASFTT                                    88

SEQ ID NO: 229         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
```

```
SEQUENCE: 229
LPAPKNLVVS RVTEDSARLS WTAPDAAFDS FQIAYPEWPP PGEAIVLTVP GSCRSYDLTG  60
LKPGTEYFVI IQGVKGGVES WPLSAIFTT                                    89

SEQ ID NO: 230         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 230
LPAPKNLVVS RVTEDSARLS WTAPDAAFDS FAIAYPEWPP QGEAIVLTVP GSCRSYDLTG  60
LKPGTEYFVV IYGVKGGSYS APLSAIFTT                                    89

SEQ ID NO: 231         moltype = AA  length = 91
FEATURE                Location/Qualifiers
REGION                 1..91
                       note = Description of Artificial Sequence: Synthetic
                        polypeptide
source                 1..91
                       mol_type = protein
                       organism = synthetic construct
SEQUENCE: 231
LPAPKNLVVS RVTEDSARLS WTAPDAAFDS FAITYIEKEH IEDGEAIVLT VPGSCRSYDL  60
TGLKPGTEYW VPIWGVKGGA NSWPLSAIFT T                                 91

SEQ ID NO: 232         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 232
LPAPKNLVVS RVTEDSARLS WTAPDAAFDS FGILYYEPVD SGEAITLPVP GSCRSYDLTG  60
LKPGTEYWVV ITGVKGGAPS TPLGTIFTT                                    89

SEQ ID NO: 233         moltype = AA  length = 96
FEATURE                Location/Qualifiers
REGION                 1..96
                       note = Description of Artificial Sequence: Synthetic
                        polypeptide
source                 1..96
                       mol_type = protein
                       organism = synthetic construct
SEQUENCE: 233
LPAPKNLVVS RVTEDSARLS WAKRPGAFDS FLIQYQESEK VGEAIVLTVP GSCRSYDLTG  60
LKPGTEYTVS IYGVDVKYDI DSRPISSNPL SAIFTT                             96

SEQ ID NO: 234         moltype = AA  length = 90
FEATURE                Location/Qualifiers
REGION                 1..90
                       note = Description of Artificial Sequence: Synthetic
                        polypeptide
source                 1..90
                       mol_type = protein
                       organism = synthetic construct
SEQUENCE: 234
LPAPKNLVVS RVTEDSARLS WTAPDAAFDS FWITYPEWPD PGGEAIVLTV PGSCRSYDLT  60
GLKPGTEYFV VIYGVKGGEI YSPLSAIFTT                                   90

SEQ ID NO: 235         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 235
LPAPKNLVVS RVTEDSARLS WTAPDAAFDS FQIAYPEYPP PGEAIVLTVP GSERSYDLTG  60
LKPGTEYFVI IQGVKGGVES WPLSAIFTT                                    89

SEQ ID NO: 236         moltype = AA  length = 89
FEATURE                Location/Qualifiers
REGION                 1..89
```

-continued

```
                        note = Description of Artificial Sequence: Synthetic
                         polypeptide
source                  1..89
                        mol_type = protein
                        organism = synthetic construct
SEQUENCE: 236
LPAPKNLVVS RVTEDSARLS WTAPDAAFDS FQIAYPELPP PGEAIVLTVP GSERSYDLTG  60
LKPGTEYFVI IQGVKGGVES WPLSAIFTT                                    89

SEQ ID NO: 237          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 237
LPAPKNLVVS RVTEDSARLS WTAPDAAFDS FQIAYPEIPP PGEAIVLTVP GSERSYDLTG  60
LKPGTEYFVI IQGVKGGVES WPLSAIFTT                                    89

SEQ ID NO: 238          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 238
LPAPKNLVVS RVTEDSARLS WTAPDAAFDS FQIAYPEWPP PGEAIVLTVP GSERSYDLTG  60
LKPGTEYFVI IQGVKGGVES YPLSAIFTT                                    89

SEQ ID NO: 239          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 239
LPAPKNLVVS RVTEDSARLS WTAPDAAFDS FQIAYPEWPP PGEAIVLTVP GSERSYDLTG  60
LKPGTEYFVI IQGVKGGVES LPLSAIFTT                                    89

SEQ ID NO: 240          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 240
LPAPKNLVVS RVTEDSARLS WTAPDAAFDS FQIAYPEWPP PGEAIVLTVP GSERSYDLTG  60
LKPGTEYFVI IQGVKGGVES SPLSAIFTT                                    89

SEQ ID NO: 241          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 241
LPAPKNLVVS RVTEDSARLS WTAPDAAFDS FQIAYPEWPP PGEAIVLTVP GSERSYDLTG  60
LKPGTEYFVI IQGVKGGVES EPLSAIFTT                                    89

SEQ ID NO: 242          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 242
LPAPKNLVVS RVTEDSARLS WTAPDAAFDS FAITYIEKEH IEEGEAIVLT VPGSERSYDL  60
```

-continued

```
TGLKPGTEYW VPIWGVKGGA NSWPLSAIFT T                                  91

SEQ ID NO: 243          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 243
LPAPKNLVVS RVTEDSARLS WTAPDAAFDS FAITYIEKEH IESGEAIVLT VPGSERSYDL  60
TGLKPGTEYW VPIWGVKGGA NSWPLSAIFT T                                  91

SEQ ID NO: 244          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 244
LPAPKNLVVS RVTEDSARLS WTAPDAAFDS FAITYIEKEH IEDGEAIVLT VPGSERSYDL  60
TGLKPGTEYY VPIWGVKGGA NSWPLSAIFT T                                  91

SEQ ID NO: 245          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 245
LPAPKNLVVS RVTEDSARLS WTAPDAAFDS FAITYIEKEH IEDGEAIVLT VPGSERSYDL  60
TGLKPGTEYF VPIWGVKGGA NSWPLSAIFT T                                  91

SEQ ID NO: 246          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 246
LPAPKNLVVS RVTEDSARLS WTAPDAAFDS FAITYIEKEH IEDGEAIVLT VPGSERSYDL  60
TGLKPGTEYS VPIWGVKGGA NSWPLSAIFT T                                  91

SEQ ID NO: 247          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 247
LPAPKNLVVS RVTEDSARLS WTAPDAAFDS FAITYIEKEH IEDGEAIVLT VPGSERSYDL  60
TGLKPGTEYW VPIYGVKGGA NSWPLSAIFT T                                  91

SEQ ID NO: 248          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 248
LPAPKNLVVS RVTEDSARLS WTAPDAAFDS FAITYIEKEH IEDGEAIVLT VPGSERSYDL  60
TGLKPGTEYW VPIFGVKGGA NSWPLSAIFT T                                  91

SEQ ID NO: 249          moltype = AA  length = 91
FEATURE                 Location/Qualifiers
REGION                  1..91
                        note = Description of Artificial Sequence: Synthetic
                         polypeptide
```

-continued

```
source                  1..91
                        mol_type = protein
                        organism = synthetic construct
SEQUENCE: 249
LPAPKNLVVS RVTEDSARLS WTAPDAAFDS FAITYIEKEH IEDGEAIVLT VPGSERSYDL  60
TGLKPGTEYW VPISGVKGGA NSWPLSAIFT T                                 91

SEQ ID NO: 250          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 250
LPAPKNLVVS RVTEDSARLS WTAPDAAFDS FAITYIEKEH IEDGEAIVLT VPGSERSYDL  60
TGLKPGTEYW VPIWGVKGGA NSYPLSAIFT T                                 91

SEQ ID NO: 251          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 251
LPAPKNLVVS RVTEDSARLS WTAPDAAFDS FAITYIEKEH IEDGEAIVLT VPGSERSYDL  60
TGLKPGTEYW VPIWGVKGGA NSEPLSAIFT T                                 91

SEQ ID NO: 252          moltype = AA  length = 91
FEATURE                 Location/Qualifiers
REGION                  1..91
                        note = Description of Artificial Sequence: Synthetic
                         polypeptide
source                  1..91
                        mol_type = protein
                        organism = synthetic construct
SEQUENCE: 252
LPAPKNLVVS RVTEDSARLS WTAPDAAFDS FAITYIEKEH IEDGEAIVLT VPGSERSYDL  60
TGLKPGTEYW VPIWGVKGGA QSWPLSAIFT T                                 91

SEQ ID NO: 253          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 253
LPAPKNLVVS RVTEDSARLS WTAPDAAFDS FGILYYEPVD SGEAITLPVP GSERSYDLTG  60
LKPGTEYFVV ITGVKGGAPS TPLGTIFTT                                   89

SEQ ID NO: 254          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 254
LPAPKNLVVS RVTEDSARLS WTAPDAAFDS FGILYYEPVD SGEAITLPVP GSERSYDLTG  60
LKPGTEYYVV ITGVKGGAPS TPLGTIFTT                                   89

SEQ ID NO: 255          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 255
LPAPKNLVVS RVTEDSARLS WTAPDAAFDS FGILYYEPVD SGEAITLPVP GSERSYDLTG  60
LKPGTEYHVV ITGVKGGAPS TPLGTIFTT                                   89
```

```
SEQ ID NO: 256         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 256
LPAPKNLVVS RVTEDSARLS WTAPDAAFDS FAIAYPEYPP QGEAIVLTVP GSERSYDLTG  60
LKPGTEYFVV IYGVKGGSYS APLSAIFTT                                    89

SEQ ID NO: 257         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 257
LPAPKNLVVS RVTEDSARLS WTAPDAAFDS FAIAYPELPP QGEAIVLTVP GSERSYDLTG  60
LKPGTEYFVV IYGVKGGSYS APLSAIFTT                                    89

SEQ ID NO: 258         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 258
LPAPKNLVVS RVTEDSARLS WTAPDAAFDS FAIAYPEIPP QGEAIVLTVP GSERSYDLTG  60
LKPGTEYFVV IYGVKGGSYS APLSAIFTT                                    89

SEQ ID NO: 259         moltype = AA  length = 89
FEATURE                Location/Qualifiers
REGION                 1..89
                       note = Description of Artificial Sequence: Synthetic
                        polypeptide
source                 1..89
                       mol_type = protein
                       organism = synthetic construct
SEQUENCE: 259
LPAPKNLVVS RVTEDSARLS WTAPDAAFDS FAIAYPEHPP QGEAIVLTVP GSERSYDLTG  60
LKPGTEYFVV IYGVKGGSYS APLSAIFTT                                    89

SEQ ID NO: 260         moltype = AA  length = 90
FEATURE                Location/Qualifiers
REGION                 1..90
                       note = Description of Artificial Sequence: Synthetic
                        polypeptide
source                 1..90
                       mol_type = protein
                       organism = synthetic construct
SEQUENCE: 260
LPAPKNLVVS RVTEDSARLS WTAPDAAFDS FYITYPEWPD PGGEAIVLTV PGSERSYDLT  60
GLKPGTEYFV VIYGVKGGEI YSPLSAIFTT                                   90

SEQ ID NO: 261         moltype = AA  length = 90
FEATURE                Location/Qualifiers
REGION                 1..90
                       note = Description of Artificial Sequence: Synthetic
                        polypeptide
source                 1..90
                       mol_type = protein
                       organism = synthetic construct
SEQUENCE: 261
LPAPKNLVVS RVTEDSARLS WTAPDAAFDS FQITYPEWPD PGGEAIVLTV PGSERSYDLT  60
GLKPGTEYFV VIYGVKGGEI YSPLSAIFTT                                   90

SEQ ID NO: 262         moltype = AA  length = 90
FEATURE                Location/Qualifiers
REGION                 1..90
                       note = Description of Artificial Sequence: Synthetic
                        polypeptide
source                 1..90
                       mol_type = protein
```

```
                        organism = synthetic construct
SEQUENCE: 262
LPAPKNLVVS RVTEDSARLS WTAPDAAFDS FSITYPEWPD PGGEAIVLTV PGSERSYDLT  60
GLKPGTEYFV VIYGVKGGEI YSPLSAIFTT                                  90

SEQ ID NO: 263          moltype = AA  length = 90
FEATURE                 Location/Qualifiers
REGION                  1..90
                        note = Description of Artificial Sequence: Synthetic
                         polypeptide
source                  1..90
                        mol_type = protein
                        organism = synthetic construct
SEQUENCE: 263
LPAPKNLVVS RVTEDSARLS WTAPDAAFDS FWITYPEYPD PGGEAIVLTV PGSERSYDLT  60
GLKPGTEYFV VIYGVKGGEI YSPLSAIFTT                                  90

SEQ ID NO: 264          moltype = AA  length = 90
FEATURE                 Location/Qualifiers
REGION                  1..90
                        note = Description of Artificial Sequence: Synthetic
                         polypeptide
source                  1..90
                        mol_type = protein
                        organism = synthetic construct
SEQUENCE: 264
LPAPKNLVVS RVTEDSARLS WTAPDAAFDS FWITYPELPD PGGEAIVLTV PGSERSYDLT  60
GLKPGTEYFV VIYGVKGGEI YSPLSAIFTT                                  90

SEQ ID NO: 265          moltype = AA  length = 90
FEATURE                 Location/Qualifiers
REGION                  1..90
                        note = Description of Artificial Sequence: Synthetic
                         polypeptide
source                  1..90
                        mol_type = protein
                        organism = synthetic construct
SEQUENCE: 265
LPAPKNLVVS RVTEDSARLS WTAPDAAFDS FWITYPEIPD PGGEAIVLTV PGSERSYDLT  60
GLKPGTEYFV VIYGVKGGEI YSPLSAIFTT                                  90

SEQ ID NO: 266          moltype = AA  length = 90
FEATURE                 Location/Qualifiers
REGION                  1..90
                        note = Description of Artificial Sequence: Synthetic
                         polypeptide
source                  1..90
                        mol_type = protein
                        organism = synthetic construct
SEQUENCE: 266
LPAPKNLVVS RVTEDSARLS WTAPDAAFDS FWITYPEWPP PGGEAIVLTV PGSERSYDLT  60
GLKPGTEYFV VIYGVKGGEI YSPLSAIFTT                                  90

SEQ ID NO: 267          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 267
LPAPKNLVVS RVTEDSARLS WTAPDAAFDS FAIAYAEWPP QGEAIVLTVP GSERSYDLTG  60
LKPGTEYFVV IYGVKGGSYS APLSAIFTT                                   89

SEQ ID NO: 268          moltype = AA  length = 90
FEATURE                 Location/Qualifiers
REGION                  1..90
                        note = Description of Artificial Sequence: Synthetic
                         polypeptide
source                  1..90
                        mol_type = protein
                        organism = synthetic construct
SEQUENCE: 268
LPAPKNLVVS RVTEDSARLS WTAPDAAFDS FWITYAEWPD PGGEAIVLTV PGSERSYDLT  60
GLKPGTEYFV VIYGVKGGEI YSPLSAIFTT                                  90

SEQ ID NO: 269          moltype = AA  length = 89
FEATURE                 Location/Qualifiers
```

```
REGION                  1..89
                        note = Description of Artificial Sequence: Synthetic
                         polypeptide
source                  1..89
                        mol_type = protein
                        organism = synthetic construct
SEQUENCE: 269
LPAPKNLVVS RVTEDSARLS WTAPDAAFDS FGILYYEPVD SGEAITLTVP GSERSYDLTG  60
LKPGTEYWVV ITGVKGGAPS TPLGTIFTT                                    89

SEQ ID NO: 270          moltype = AA  length = 89
FEATURE                 Location/Qualifiers
REGION                  1..89
                        note = Description of Artificial Sequence: Synthetic
                         polypeptide
source                  1..89
                        mol_type = protein
                        organism = synthetic construct
SEQUENCE: 270
LPAPKNLVVS EVTEDSARLS WTAPDAAFDS FLIQYQESEK VGEAIVLTVP GSERSYDLTG  60
LKPGTEYTVS IYGVKGGHRS NPLSAIFTT                                    89

SEQ ID NO: 271          moltype = AA  length = 276
FEATURE                 Location/Qualifiers
source                  1..276
                        mol_type = protein
                        organism = Macaca fascicularis
SEQUENCE: 271
MRNQAPGRPK GATSPPPLPT GSRAPPVAPE LRAEPRPGER VMAPPVTALL LPLVLLLHAA  60
RPNQFRVSPL GRTWNLGETV ELKCQVLLSN PTSGCSWLFQ PRGTAARPTF LLYLSQNKPK  120
AAEGLDTQRF SGKRLGDTFV LTLRDFRQEN EGYYFCSALS NSIMYFSHFV PVFLPAKPTT  180
TPAPRPPTPA PTTASQPLSL RPEACRPAAG GSVNTRGLDF ACDIYIWAPL AGACGVLLLS  240
LVITLYCNHR NRRRVCKCPR PVVKSGGKPS LSDRYV                            276

SEQ ID NO: 272          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 272
GSGS                                                               4

SEQ ID NO: 273          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 273
GGGSGGGS                                                           8

SEQ ID NO: 274          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 274
GGGGSGGGGS GGGGSGGGGS GGGGS                                        25

SEQ ID NO: 275          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 275
APAP                                                               4

SEQ ID NO: 276          moltype = AA  length = 10
FEATURE                 Location/Qualifiers
REGION                  1..10
                        note = Description of Artificial Sequence: Synthetic peptide
source                  1..10
```

-continued

```
                          mol_type = protein
                          organism = synthetic construct
SEQUENCE: 276
APAPAPAPAP                                                          10

SEQ ID NO: 277            moltype = AA  length = 20
FEATURE                   Location/Qualifiers
REGION                    1..20
                          note = Description of Artificial Sequence: Synthetic peptide
source                    1..20
                          mol_type = protein
                          organism = synthetic construct
SEQUENCE: 277
APAPAPAPAP APAPAPAPAP                                               20

SEQ ID NO: 278            moltype = AA  length = 40
FEATURE                   Location/Qualifiers
REGION                    1..40
                          note = Description of Artificial Sequence: Synthetic
                           polypeptide
source                    1..40
                          mol_type = protein
                          organism = synthetic construct
SEQUENCE: 278
APAPAPAPAP APAPAPAPAP APAPAPAPAP APAPAPAPAP                         40

SEQ ID NO: 279            moltype = AA  length = 29
FEATURE                   Location/Qualifiers
REGION                    1..29
                          note = Description of Artificial Sequence: Synthetic peptide
source                    1..29
                          mol_type = protein
                          organism = synthetic construct
SEQUENCE: 279
AEAAAKEAAA KEAAAKEAAA KEAAAKAAA                                     29

SEQ ID NO: 280            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 280
TAPDAAFD                                                            8

SEQ ID NO: 281            moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 281
KGGHRSNP                                                            8
```

What is claimed:

1. A protein comprising an amino acid sequence, wherein the amino acid sequence has a sequence of any one of SEQ ID NOs:130-228 and 235-269.

2. The protein of claim 1, wherein the protein is conjugated to a second molecule.

3. The protein of claim 2, wherein the second molecule is a detectable label.

4. The protein of claim 3, wherein the detectable label is a radioactive isotope, magnetic beads, metallic beads, colloidal particles, a fluorescent dye, an electron-dense reagent, an enzyme, biotin, digoxigenin, or hapten.

5. The protein of claim 1, wherein the protein has a cysteine substitution at residue position 54 corresponding to an amino acid sequence of SEQ ID NOs:79, 81, 83, 89, 122, or 68.

6. The protein of claim 1, further comprising a methionine at the N-terminus of the protein.

7. The protein of claim 1, wherein the protein is coupled to a half-life extending moiety.

8. The protein of claim 7, wherein the half-life extending moiety is albumin, an albumin binding molecule, a polyethylene glycol (PEG), or an Fc region of an immunoglobulin.

9. A diagnostic kit comprising the protein of claim 1.

10. A capture agent comprising the protein of claim 1.

11. The capture agent of claim 10, wherein the protein has a cysteine substitution at residue position 54 corresponding to a sequence of SEQ ID NOs:79, 81, 83, 89, 122, or 68.

12. The capture agent of claim 11, wherein the substituted cysteine is conjugated to Zr-89 or I-124.

13. The protein of claim 1, wherein the amino acid sequence is selected from the group consisting of SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, and SEQ ID NO:149.

14. The protein of claim 1, wherein the amino acid sequence is selected from the group consisting of SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, and SEQ ID NO:169.

15. The protein of claim 1, wherein the amino acid sequence is selected from the group consisting of SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, and SEQ ID NO:189.

16. The protein of claim 1, wherein the amino acid sequence is selected from the group consisting of SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, and SEQ ID NO:209.

17. The protein of claim 1, wherein the amino acid sequence is selected from the group consisting of SEQ ID NO:210, SEQ ID NO:2011, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, and SEQ ID NO:228.

18. The protein of claim 1, wherein the amino acid sequence is selected from the group consisting of SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, and SEQ ID NO:249.

19. The protein of claim 1, wherein the amino acid sequence is selected from the group consisting of SEQ ID NO:250, SEQ ID NO:251, SEQ ID NO:252, SEQ ID NO:253, SEQ ID NO:254, SEQ ID NO:255, SEQ ID NO:256, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268, and SEQ ID NO:269.

* * * * *